United States Patent
Trabanco-Suárez et al.

(10) Patent No.: US 9,346,811 B2
(45) Date of Patent: *May 24, 2016

(54) 6,7-DIHYDRO-PYRAZOLO[1,5-A]PYRAZIN-4-YLAMINE DERIVATIVES USEFUL AS INHIBITORS OF BETA-SECRETASE (BACE)

(75) Inventors: Andrés Avelino Trabanco-Suárez, Toledo (ES); Henricus Jacobus Maria Gijsen, Beerse (BE); Michiel Luc Maria Van Gool, Toledo (ES); Juan Antonio Vega Ramiro, Toledo (ES); Francisca Delgado-Jiménez, Toledo (ES)

(73) Assignee: JANSSEN PHARMACEUTICA NV (BE)

(*) Notice: Subject to any disclaimer, the term of this patent is extended or adjusted under 35 U.S.C. 154(b) by 16 days.

This patent is subject to a terminal disclaimer.

(21) Appl. No.: 14/002,169

(22) PCT Filed: Feb. 29, 2012

(86) PCT No.: PCT/EP2012/053455
§ 371 (c)(1),
(2), (4) Date: Aug. 29, 2013

(87) PCT Pub. No.: WO2012/117027
PCT Pub. Date: Sep. 7, 2012

(65) Prior Publication Data
US 2014/0005200 A1  Jan. 2, 2014

(30) Foreign Application Priority Data
Mar. 1, 2011 (EP) ..................................... 11156463

(51) Int. Cl.
*A61K 31/4985* (2006.01)
*A61K 31/41* (2006.01)
*C07D 487/04* (2006.01)

(52) U.S. Cl.
CPC .................... *C07D 487/04* (2013.01)

(58) Field of Classification Search
CPC .... A61K 31/4985; A61K 31/41; C07D 487/04
See application file for complete search history.

(56) References Cited

U.S. PATENT DOCUMENTS

| 4,188,389 | A | 2/1980 | Jirkovsky |
| 5,292,732 | A | 3/1994 | Rover |
| 8,207,164 | B2 | 6/2012 | Holzer |
| 2005/0282825 | A1 | 12/2005 | Malamas |
| 2007/0005404 | A1 | 1/2007 | Raz |
| 2007/0225372 | A1 | 9/2007 | Bueno Melendo |
| 2008/0051420 | A1 | 2/2008 | Berg |
| 2009/0082560 | A1 | 3/2009 | Kobayashi |
| 2012/0238557 | A1 | 9/2012 | Masui et al. |
| 2012/0277244 | A1 | 11/2012 | Tintelnot-Blomley |
| 2014/0256715 | A1 | 9/2014 | Hurth et al. |

FOREIGN PATENT DOCUMENTS

| CA | 2825620 | 9/2012 |
| EP | 2147914 | 1/2010 |
| EP | 2 518 059 | 10/2012 |
| WO | WO03089434 | 10/2003 |
| WO | WO2004026877 | 4/2004 |
| WO | WO2004058176 | 7/2004 |
| WO | WO2005037832 | 4/2005 |
| WO | WO2006034093 A2 | 3/2006 |
| WO | WO2006076284 | 7/2006 |
| WO | WO2006/138265 | 12/2006 |
| WO | WO2007/005404 | 1/2007 |
| WO | WO2007058583 A2 | 5/2007 |
| WO | WO2007114771 A1 | 10/2007 |
| WO | WO2007138265 A2 | 12/2007 |
| WO | WO2009022961 A1 | 2/2009 |
| WO | WO2009058300 A1 | 5/2009 |
| WO | WO2009097278 A1 | 8/2009 |
| WO | WO2009102468 A1 | 8/2009 |
| WO | WO2009134617 A1 | 11/2009 |
| WO | WO 2011/002409 | 1/2011 |
| WO | WO 2011/009943 | 1/2011 |
| WO | WO2011020806 A1 | 2/2011 |

(Continued)

OTHER PUBLICATIONS

Sheridan, R.P. "The Most Common Chemical Replacements in Drug-Like Compounds" J. Chem. Inf. Comput. Sci., 2002, vol. 42, pp. 103-108.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Esterhazy et al_Cell Metabolism, "Bace2 is a β Cell-Enriched Protease that Regulates Pancreatic β Cell Function and Mass", 2011 14 365-377.
Fleck et al. 2012, Curr. Alzheimer Res., "Bace1Dependent Neuregulin Processing: review" 9, 178-183.
Hackam, et al. JAMA, "Translation of Research Evidence From animals to Humans", 296(14), 2006, 1731-1732.
Haniu et al., 2000, J. Biol. Chem., "Protein Structure and folding: Characterization of Alzheimer's β-secretase protein BACE: a Pepsin Family member with Unusual Properties", 275, 21099-21106.

(Continued)

*Primary Examiner* — Kendra D Carter
(74) *Attorney, Agent, or Firm* — Yuriy P. Stercho

(57) ABSTRACT

The present invention relates to novel 6,7-dihydro-pyrazolo[1,5-a]pyrazin-4-yl-amine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease or dementia associated with beta-amyloid.

12 Claims, No Drawings

(56) References Cited

FOREIGN PATENT DOCUMENTS

| WO | WO2011071135 A1 | 6/2011 |
|---|---|---|
| WO | WO2011080176 A1 | 7/2011 |
| WO | WO 2011/154431 | 12/2011 |
| WO | WO2012057247 A1 | 5/2012 |
| WO | WO2012085038 A1 | 6/2012 |
| WO | WO 2012/098064 | 7/2012 |
| WO | WO2012117027 A1 | 9/2012 |
| WO | WO2012120023 A1 | 9/2012 |

OTHER PUBLICATIONS

Hemming et al. 2009, PLS ONE, "Identification of β-Secretase (BACE1) Substrates using Quantitative Proteomics", 4, e8477.
Hong et al, 2000, Science, "Structure of the Protease domain of memapsin 2(β-Secretase) Complexed with Inhibitor" 290, 150-153.
Jonsson et al. 2012, Nature, "A mutation in APP protects against Alzheimer's disease and age-related cognitive decline", 488, 96-99.
Kim et al. 2011, J. Biol. Chem. "Molecular Bases of Disease: Reduced Sodium Channel Nav1.1 Levels in BACE1-null Mice", 286, 8106-8116.
Kondoh et al. Breast Cancer Res.Treat., "A novel aspartic protease gene, ALP56, is up-regulated in human breast cancer independently from the cathepsin D gene", 2003, vol. 78, pp. 37-44.
Kuhn et al. 2012, EMBO J. "Secretome protein enrichment identifies physiological BACElprotease substrates in neurons" 31, 3157-3168.
Kuhn et al. J. Biol. Chem."Protein Synthesis, Post-translation Modification, and Degradation: Regulated Intramembrane Proteolysis of the Interleukin-1 receptor II by α-,β-, and γ-Secretase", 2007, vol. 282, No. 16, pp. 11982-11995.
Luo et al., 2001, Nat. Neurosci, "Mice deficient in BACE!, the Alzheimer's β-secretase, have normal phenotype and abolished β-amyloid generation", 4, 231-261.
Naus et al. 2004, J. Biol. Chem.,"Enzyme Catalysis and Regulation: Extodomain Shedding of the Neural Recognition Molecule CHL1 by the Metalloprotease-disintegrin ADAM8 Promotes Neurite Outgrowth and Suppresses Neuronal Cell Death", 279, 16083-16090.
Ostermann et al, 2006, Journal of molecular biology, "Crystal Structure of Human BACE2 in Complex with a Hydroxyethylamine transition-state Inhibitor", 355, (2), 249-61.
Patani et al, Chem.Rev., "Bioisosterism: A Rational Approach in Drug Design", 1996, 96, 3147-3176.
Roberds et al., 2001, Hum. Mol. Genet, "BACE knockout mice are healthy despite lacking the primary β-secretase activity in the brain: implications for Alzheimer's disease therapeutics",10, 1317-1324.
Rochin et al. PNAS, "BACE2 processes PMEL to form the melanosome amyloid matrix in pigment cells", Jun. 25, 2013, vol. 110, No. 26, pp. 10658-10663.
Silvestri Medicinal Research Reviews, "Boom in the development of Non-Peptidic β-secretase (BACE1) Inhibitors for the Treatment of Alzheimer's Disease", 295-238_2009.
Stutzer et al. 2013, J. Biol. Chem., "Systematic Proteomic Analysis Identifies β-Site Amyloid Precursor Protein Cleaving Enzyme 2 and 1 (BACE2 and BACE1) Substrates in Pancreatic β-Cells" 288, 10536-10547.
Cheret et al. 2013 EMBO Journal, "Bace1 and Neuregulin-1 cooperate to control formation and maintenance of muscle spindles", (2013), 32(14), 2015-2028.
Jordan, V. C. Nature Reviews: Drug Discovery,"Tamoxifen: A Most Unlikely Pioneering Medicine", 2, 2003, 205.
Vassar et al., J. Neurochem., "Function, therapeutic potential and cell biology of BACE proteases: current status and future prospects", (2014) 10.1111/jnc.12715.
Vippagunta, et al. Advanced Drug Delivery Reviews, "Crystalline Solids", 48, 2001, 18.
Wang et al. Trends in Pharmacological Sciences, Apr, "β-Secretase: its biology as a therapeutic target in diseases", 2013, vol. 34, No. 4, pp. 215-225.
Willem et al. 2009, Semin. Cell Dev. Biol., Function, regulation and therapeutic properties of β-secretase (BACE1) 20, 175-182.
Yan and Vassar Lancet Neurol. "Targeting the β secretase BACE1 for Alzheimer's disease therapy", 2014, vol. 13, pp. 319-329.
Yan et al. J Alzheimers Dis. "Can BACE! Inhibition Mitigate Early Axonal Pathology in Neurological Diseases?", 2014, 30 vol. 38, No. 4, pp. 705-718.
Zhou et al. 2012, J. Biol. Chem. "The Neural Cell Adhesion Molecules L1 and CHL1 are Cleaved by BACE1 Protease in Vivo", 287, 25927-25940.
Koike H et al,. "Thimet Oligopeptidase Cleaves the Full-Lengh alzheimer Amyloid Precursor Protein at a β-Secretase Cleavage Site in COS Cells", J. Biochem. 1999, 126, 235-242.
Hilpert, et al., "β-Secretase (BACE1) Inhibitors with High in vivo efficacy Suitable for Clinical Evaluation in Alzheimer's Disease", Journal of Medicinal Chemistry, vol. 56, No. 10, pp. 3980-3995, 2013.
Purser, et al., "Flourine in Medicinal Chemistry", Chemical Society Reviews, 2008, vol. 37, pp. 320-330.
Park, et al., "Metabolism of Fluorine-Containing Drugs", Annual Ref. Pharmacol. Toxicol. 2001, vol. 41, pp. 443-470.
Park, et al., Effects of Flourine Substitution on Drug Metabolism: Pharmacological and Toxicological Implicatins*, Drug metabolism reviews, vol. 26(3), 1994, pp. 605-643.
Wang, et al., Fluroine in Pharmaceutical Industry: Flourine-Containing Drugs Introduced to the Market in the Last Decade (2001-2011).
Woltering, et al., "BACE Inhibitors: A head group scan on a series of amides:", Biorganic & Medicinal Chemistry Letters, vol. 23, pp. 4239-4243, 2013.
Ginman, et al., "Core refinement toward Permeable β-Secretase (BACE-1) Inhibitors with Low HERG Activity", Journal of Medicinal Chemistry, vol. 56, pp. 4181-4205, 2013.
Zhang, et al, "Application of Amybidbeta Protein in the Diagnosis of Alzheimer's Disease", vol. 29, No. 1, 2008.
International Search Report for PCT/EP2012/053455 dated Feb. 5, 2012.

* cited by examiner

6,7-DIHYDRO-PYRAZOLO[1,5-A]PYRAZIN-4-YLAMINE DERIVATIVES USEFUL AS INHIBITORS OF BETA-SECRETASE (BACE)

CROSS REFERENCE TO RELATED APPLICATIONS

This application is the national stage of PCT Application No. PCT/EP2012/053455, filed Feb. 29, 2012, which claims priority from European Patent Application No. 11156463.9, filed Mar. 1, 2011, the entire disclosures of which are hereby incorporated in their entirety.

FIELD OF THE INVENTION

The present invention relates to novel 6,7-dihydro-pyrazolo[1,5-a]pyrazin-4-yl-amine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease or dementia associated with beta-amyloid.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibrillary tangles which are generated by hyperphosphorylation of tau protein and amyloid plaques which form by aggregation of beta-amyloid 1-42 (Abeta 1-42) peptide. Abeta 1-42 forms oligomers and then fibrils, and ultimately amyloid plaques.

The oligomers and fibrils are believed to be especially neurotoxic and may cause most of the neurological damage associated with AD. Agents that prevent the formation of Abeta 1-42 have the potential to be disease-modifying agents for the treatment of AD. Abeta 1-42 is generated from the amyloid precursor protein (APP), comprised of 770 amino acids. The N-terminus of Abeta 1-42 is cleaved by beta-secretase (BACE), and then gamma-secretase cleaves the C-terminal end. In addition to Abeta 1-42, gamma-secretase also liberates Abeta 1-40 which is the predominant cleavage product as well as Abeta 1-38 and Abeta 1-43. These Abeta forms can also aggregate to form oligomers and fibrils. Thus, inhibitors of BACE would be expected to prevent the formation of Abeta 1-42 as well as Abeta 1-40, Abeta 1-38 and Abeta 1-43 and would be potential therapeutic agents in the treatment of AD.

SUMMARY OF THE INVENTION

The present invention is directed to a compound of Formula (I)

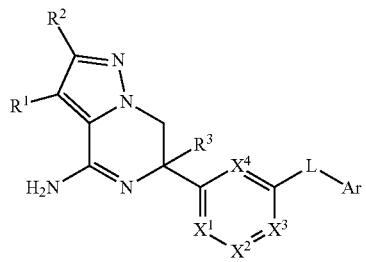

or a tautomer or a stereoisomeric form thereof, wherein
$R^1$ and $R^2$ are independently selected from the group consisting of hydrogen, halo, cyano, $C_{1-3}$alkyl, mono- and polyhalo-$C_{1-3}$alkyl or $C_{3-6}$cycloalkyl;
$R^3$ is selected from the group consisting of hydrogen, $C_{1-3}$alkyl, $C_{3-6}$cycloalkyl, mono- and polyhalo-$C_{1-3}$alkyl, homoaryl and heteroaryl;
$X^1, X^2, X^3, X^4$ are independently $C(R^4)$ or N, provided that no more than two thereof represent N; each $R^4$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^5$)CO—, wherein $R^5$ is hydrogen or $C_{1-3}$alkyl;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy;
heteroaryl is selected from the group consisting of pyridyl, pyrimidyl, pyrazyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy; or an addition salt or a solvate thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the beta-secretase enzyme, comprising administering to a subject in need thereof a therapeutically effective amount of any of the compounds or pharmaceutical compositions described above.

Further exemplifying the invention are methods of inhibiting the beta-secretase enzyme, comprising administering to a subject in need thereof a therapeutically effective amount of any of the compounds or pharmaceutical compositions described above.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is any of the compounds described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I) as defined hereinbefore and pharmaceutically acceptable salts and solvates thereof. The compounds of formula (I) are inhibitors of the beta-secretase enzyme (also known as beta-site cleaving enzyme, BACE, BACE1, Asp2 or memapsin 2), and are useful in the treatment of Alzheimer's disease, mild cognitive impairment, senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the present invention, $R^1$ and $R^2$ are independently selected from hydrogen and $C_{1-3}$alkyl;
$X^1$, $X^2$, $X^3$, $X^4$ are independently $C(R^4)$ wherein each $R^4$ is selected from hydrogen and halo;
L is a bond or —$N(R^5)CO$—, wherein $R^5$ is hydrogen;
Ar is homoaryl or heteroaryl;
wherein homoaryl is phenyl or phenyl substituted with one or two substituents selected from the group consisting of halo, cyano, $C_{1-3}$alkyl, $C_{1-3}$alkyloxy, and polyhalo-$C_{1-3}$alkyloxy;
heteroaryl is selected from the group consisting of pyridyl, pyrimidyl, and pyrazyl, each optionally substituted with one or two substituents selected from the group consisting of halo, cyano, $C_{1-3}$alkyl, $C_{1-3}$alkyloxy, and polyhalo-$C_{1-3}$alkyloxy; or
an addition salt or a solvate thereof.

In another embodiment of the present invention, $R^1$ and $R^2$ are hydrogen;
$X^1$, $X^2$, $X^3$, $X^4$ are CH;
L is a bond or —$N(R^5)CO$—, wherein $R^5$ is hydrogen;
Ar is homoaryl or heteroaryl;
wherein homoaryl is phenyl substituted with chloro;
heteroaryl is selected from the group consisting of pyridyl and pyrimidyl, each optionally substituted with one or two substituents selected from the group consisting of chloro, fluoro, cyano, methyl, and methoxy; or
an addition salt or a solvate thereof.

In another embodiment, the carbon atom substituted with $R^3$ has the R-configuration.

DEFINITIONS

"Halo" shall denote fluoro, chloro and bromo; "$C_{1-3}$alkyl" shall denote a straight or branched saturated alkyl group having 1, 2 or 3 carbon atoms, e.g. methyl, ethyl, 1-propyl and 2-propyl; "$C_{1-3}$alkyloxy" shall denote an ether radical wherein $C_{1-3}$alkyl is as defined before; "mono- and polyhalo$C_{1-3}$alkyl" shall denote $C_{1-3}$alkyl as defined before, substituted with 1, 2 3 or where possible with more halo atoms as defined before; "mono- and polyhalo$C_{1-3}$alkyloxy" shall denote an ether radical wherein mono- and polyhalo$C_{1-3}$alkyl is as defined before; "$C_{3-6}$cycloalkyl" shall denote cyclopropyl, cyclobutyl, cyclopentyl and cyclohexyl; "$C_{3-6}$cycloalkanediyl" shall denote a bivalent radical such as cyclopropanediyl, cyclobutanediyl, cyclopentanediyl and cyclohexanediyl.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. If a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

The compounds of Formula (I) co-exist in a dynamic equilibrium with the tautomers of Formula (I-1).

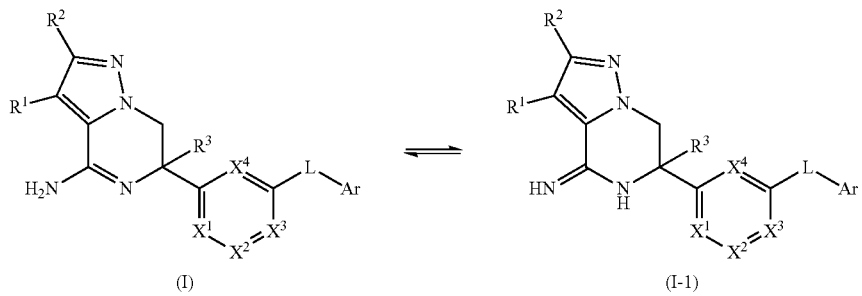

(I)    (I-1)

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The chemical names of the compounds of the present invention were generated according to the nomenclature rules agreed upon by the Chemical Abstracts Service. Some of the compounds according to formula (I) may also exist in their tautomeric form. Such forms although not explicitly indicated in the above formula are intended to be included within the scope of the present invention.

A. Preparation of the Final Compounds

Experimental Procedure 1

The final compounds according to Formula (I), can be prepared by reacting an intermediate compound of Formula (II) with an appropriate source of ammonia such as, for example, ammonium chloride or aqueous ammonia, according to reaction scheme (1), a reaction that is performed in a suitable reaction-inert solvent, such as, for example, water or methanol, under thermal conditions such as, for example, heating the reaction mixture at 60 to 90° C., for example for 4 to 100 hours. In reaction scheme (1), all variables are defined as in Formula (I).

Reaction Scheme 1

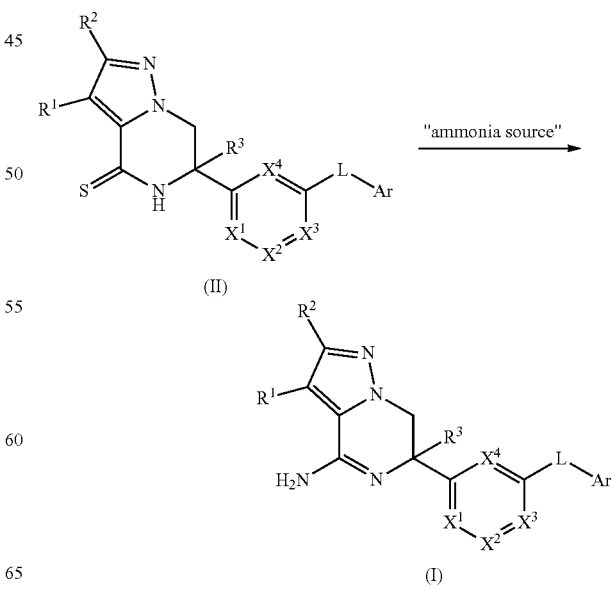

Experimental Procedure 2

The final compounds according to Formula (I-a) wherein L is —N(R⁵)CO—, can be prepared by reacting an intermediate compound of Formula (III-a) with an intermediate of Formula (IV) according to reaction scheme (2), a reaction that is performed in a suitable reaction-inert solvent, such as, for example, N,N-dimethyl-formamide, in the presence of a suitable base, such as, for example, K₃PO₄, a copper catalyst such as, for example, CuI and a diamine such as for example (1R,2R)-(−)-1,2-diaminocyclohexane, under thermal conditions such as, for example, heating the reaction mixture at 180° C., for example for 135 min under microwave irradiation. In reaction scheme (2), all variables are defined as in Formula (I) and W is halo.

Reaction Scheme 2

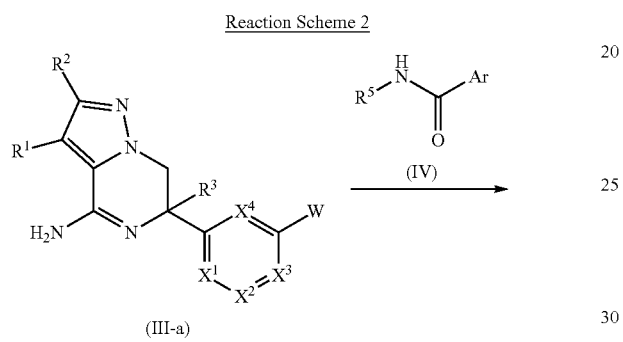

Experimental Procedure 3

Additionally, the final compounds according to Formula (I-a), can be prepared by reacting an intermediate compound of Formula (III-b) with an intermediate of Formula (V) according to reaction scheme (3), a reaction that is performed in a suitable reaction-inert solvent, such as, for example, dichloromethane or methanol, optionally in the presence of a suitable base, such as, for example, N,N-diisopropylethylamine, in the presence of a condensation agent such as for example O-(7-azabenzotriazol-1-yl)-N,N,N',N'-tetramethyluronium hexafluorophosphate or 4-(4,6-dimethoxy-1,3,5-triazin-2-yl)-4-methylmorpholinium chloride], under thermal conditions such as, for example, heating the reaction mixture at 25° C., for example for 2 hours. In reaction scheme (3), all variables are defined as in Formula (I).

Reaction Scheme 3

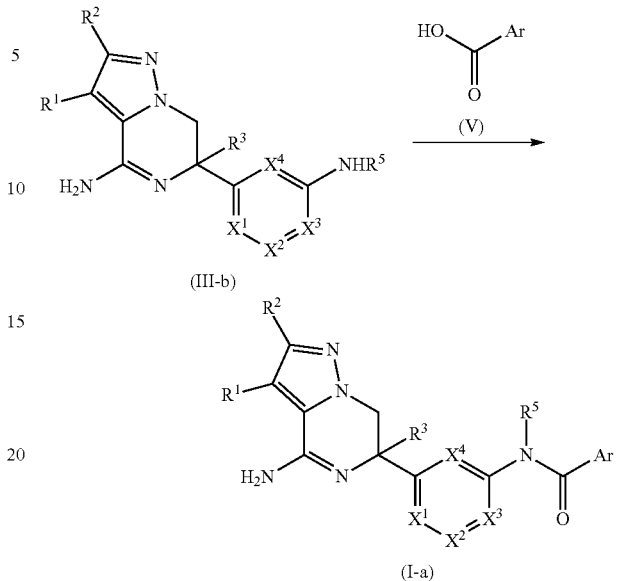

Experimental Procedure 4

Additionally, the final compounds according to Formula (I-a), can be prepared by reacting an intermediate compound of Formula (III-b) with an intermediate of Formula (VI) according to reaction scheme (4), a reaction that is performed in a suitable reaction-inert solvent, such as, for example, dichloromethane, in the presence of a suitable base, such as, for example, pyridine, under thermal conditions such as, for example, heating the reaction mixture at 25° C., for example for 2 hours. In reaction scheme (4), all variables are defined as in Formula (I) and Y is halo.

Reaction Scheme 4

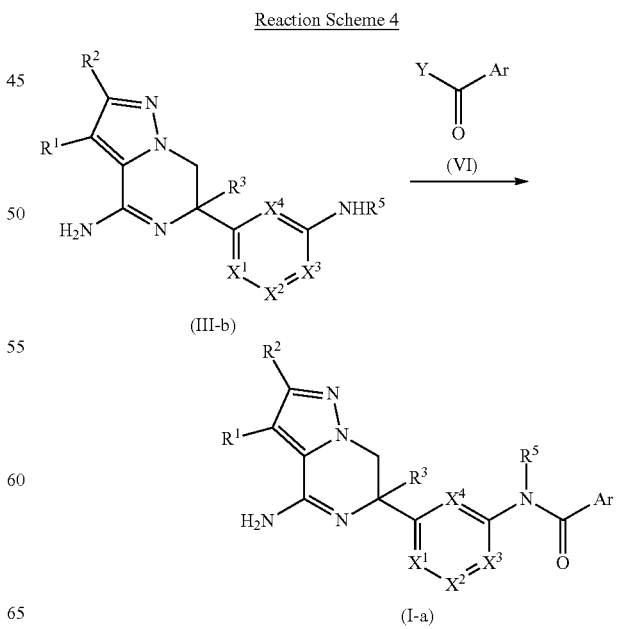

Experimental Procedure 5

The final compounds according to Formula (I-b) wherein L is a bond, can be prepared by reacting an intermediate compound of Formula (III-a) with an intermediate of Formula (VII) according to reaction scheme (5), a reaction that is performed in a suitable reaction-inert solvent, such as, for example, mixtures of inert solvents such as, for example, 1,4-dioxane/ethanol, in the presence of a suitable base, such as, for example, K$_2$CO$_3$, a Pd-complex catalyst such as, for example, tetrakis (triphenylphosphine)palladium (0) under thermal conditions such as, for example, heating the reaction mixture at 80° C., for example for 20 hours or for example, heating the reaction mixture at 150° C., for 10 min to 30 min under microwave irradiation. In reaction scheme (5), all variables are defined as in Formula (I) and W is halo. R$^6$ and R$^7$ may be hydrogen or alkyl, or may be taken together to form for example a bivalent radical of formula —CH$_2$CH$_2$—, —CH$_2$CH$_2$CH$_2$—, or —C(CH$_3$)$_2$C(CH$_3$)$_2$—.

Reaction Scheme 5

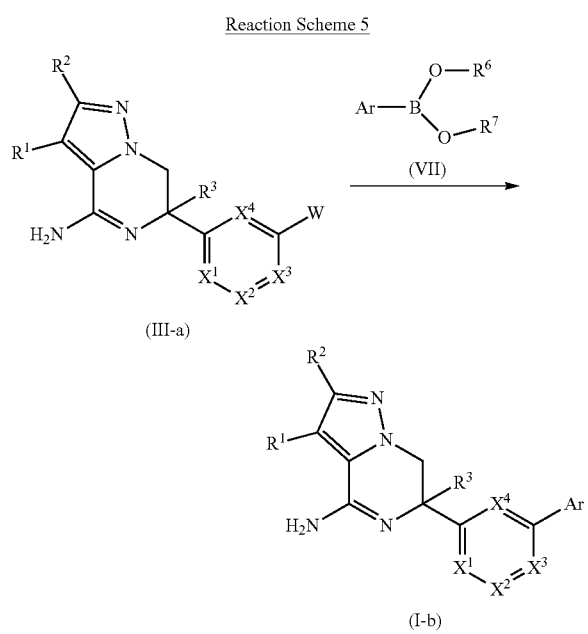

Experimental Procedure 6

The final compounds according to Formula (I-c) wherein R$^1$ is hydrogen, can be prepared from the corresponding final compounds of Formula (I-d) wherein R$^1$ is selected from the group consisting of chlorine, bromine and iodine, following art-known reduction procedures according to reaction scheme (6). For example, said reduction may be carried out by stirring the reactants under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture. In reaction scheme (6), all variables are defined as in Formula (I).

Reaction Scheme 6

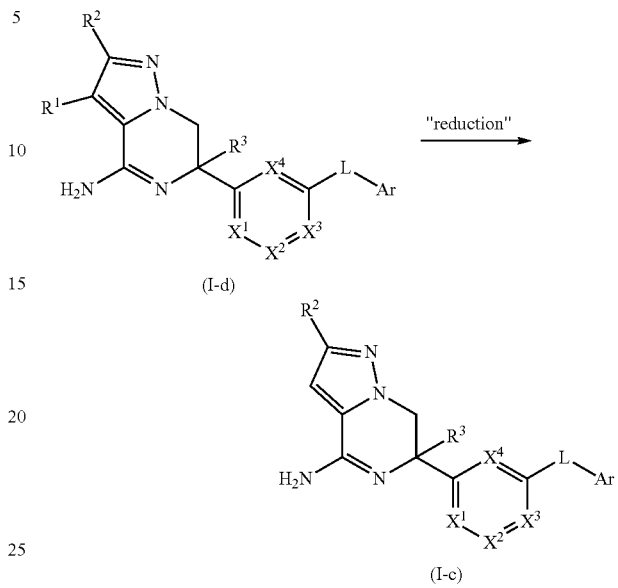

A number of intermediates and starting materials in the foregoing preparations are known compounds which may be prepared according to art-known methodologies of preparing said or similar compounds and some intermediates are new. A number of such preparation methods will be described hereinafter in more detail.

B. Preparation of the Intermediate Compounds

Experimental Procedure 7

The intermediates according to Formula (II) can be prepared by reacting an intermediate compound of Formula (VIII) with a suitable sulphur donating reagent for the synthesis of thioamides such as, for example, phosphorous pentasulfide or 2,4-bis-(4-methoxyphenyl)-1,3-dithia-2,4-diphosphetane 2,4-disulfide [Lawesson's reagent] according to reaction scheme (7), a reaction that is performed in a reaction inert solvent, such as for example, tetrahydrofuran or toluene, in the presence of a suitable base such as, for example, pyridine, under thermal conditions such as, for example, heating the reaction mixture at 100° C., for example for 5 hours. In reaction scheme (7), all variables are defined as in Formula (I).

Reaction Scheme 7

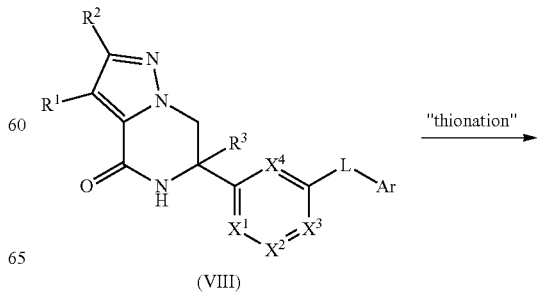

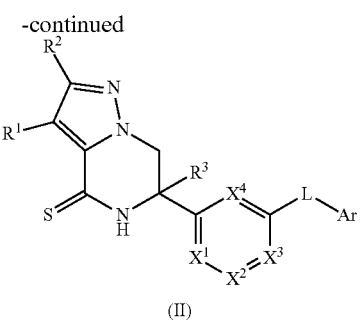

(II)

Experimental Procedure 8

The intermediates according to Formula (VIII-a) wherein L is a bond, can be prepared by reacting an intermediate compound of Formula (IX-a) with an intermediate of Formula (VII) according to reaction scheme (8), a reaction that is performed in a suitable mixture of inert solvents such as, for example, 1,4-dioxane/water, in the presence of a suitable base, such as, for example, aqueous $Na_2CO_3$, a Pd-complex catalyst such as, for example, tetrakis(triphenylphosphine) palladium (0) under thermal conditions such as, for example, heating the reaction mixture at 80° C., for example for 20 hours or for example, heating the reaction mixture at 150° C., for example for 15 to 30 min under microwave irradiation. In reaction scheme (8), all variables are defined as in Formula (I) and W is halo. $R^6$ and $R^7$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

Reaction Scheme 8

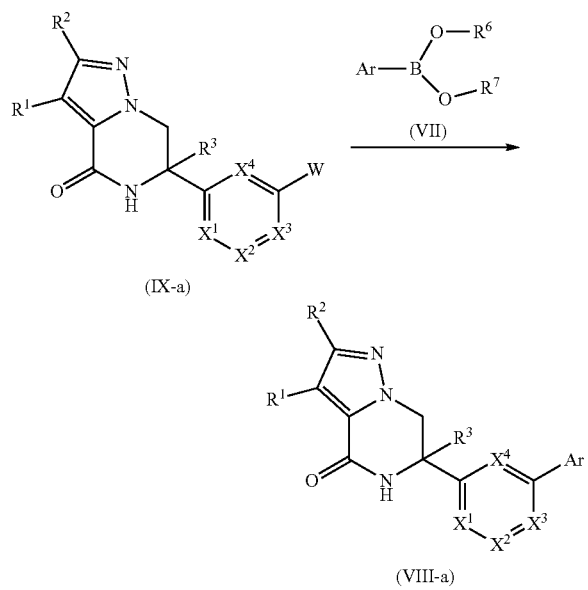

Experimental Procedure 9

The intermediates according to Formula (III-b) can be prepared from the corresponding intermediate compounds of Formula (III-a) following art-known Buchwald-Hartwig type coupling procedures according to reaction scheme (9). Said coupling may be conducted by treatment of intermediate compounds of Formula (III-a) with an intermediate of Formula (X) in a suitable reaction-inert solvent, such as, for example, ethanol or mixtures of inert solvents such as, 1,2-dimethoxyethane/water/ethanol, in the presence of a suitable base, such as, for example, aqueous $K_3PO_4$ or $Cs_2CO_3$, a Pd-complex catalyst such as, for example, [1,1'-bis(diphenylphosphino) ferrocene]-dichloropalladium(II) or trans-bis (dicyclohexylamine) palladium diacetate [DAPCy] under thermal conditions such as, for example, heating the reaction mixture at 80° C., for example for 20 hours or for example, heating the reaction mixture at 130° C., for example for 10 min under microwave irradiation. In reaction scheme (9), all variables are defined as in Formula (I) and W is halo. $R^5$ is hydrogen or $C_{1-3}$alkyl. Alternatively, when $R^5$ is hydrogen, intermediates of Formula (III-b) can be obtained as well following a two-step synthesis. First, a Buchwald-Hartwig type coupling can be performed, under the conditions known to the person skilled in the art, between intermediate (III-a) and a stable imine such as benzophenone imine. In the second step, intermediate (III-b) can be obtained as a primary amine by treating the coupled product, dissolved in a suitable solvent, such as isopropanol, with an acid, such as for example hydrochloric acid, under thermal conditions such as, for example, heating the reaction mixture at 25° C., for example for 2 hours Reaction Scheme 9

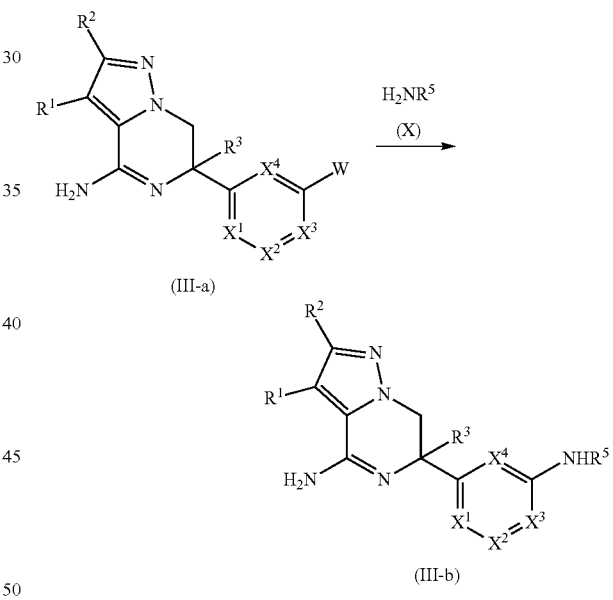

Experimental Procedure 10

Additionally, the intermediates according to Formula (III-b) wherein $R^5$ is hydrogen can be prepared from the corresponding intermediates of Formula (III-c) following art-known nitro-to-amino reduction procedures according to reaction scheme (10). For example, said reduction may conveniently be conducted in presence of an appropriate reducing agent such as tin chloride, zinc or iron, in a suitable inert solvent such as ethanol or mixtures ethanol/acetic acid or methanol/ammonium chloride aqueous solution, under suitable reaction conditions, such as at a convenient temperature, typically ranging between 70° C. and 110° C., for a period of time to ensure the completion of the reaction. The person skilled in the art would appreciate that in the case of $R^1$ and/or $R^2$ in intermediate (III-c) being a halogen selected from the group of chlorine, bromine and iodine, and undesired in the final compound, under the above described conditions also an oxidative addition-protonation process may occur, to afford intermediate (III-b), where R¹ and/or R² is hydrogen. Alternatively, said reduction may be carried out by stirring the reactants under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture. In reaction scheme (10), all variables are defined as in Formula (I).

Reaction Scheme 10

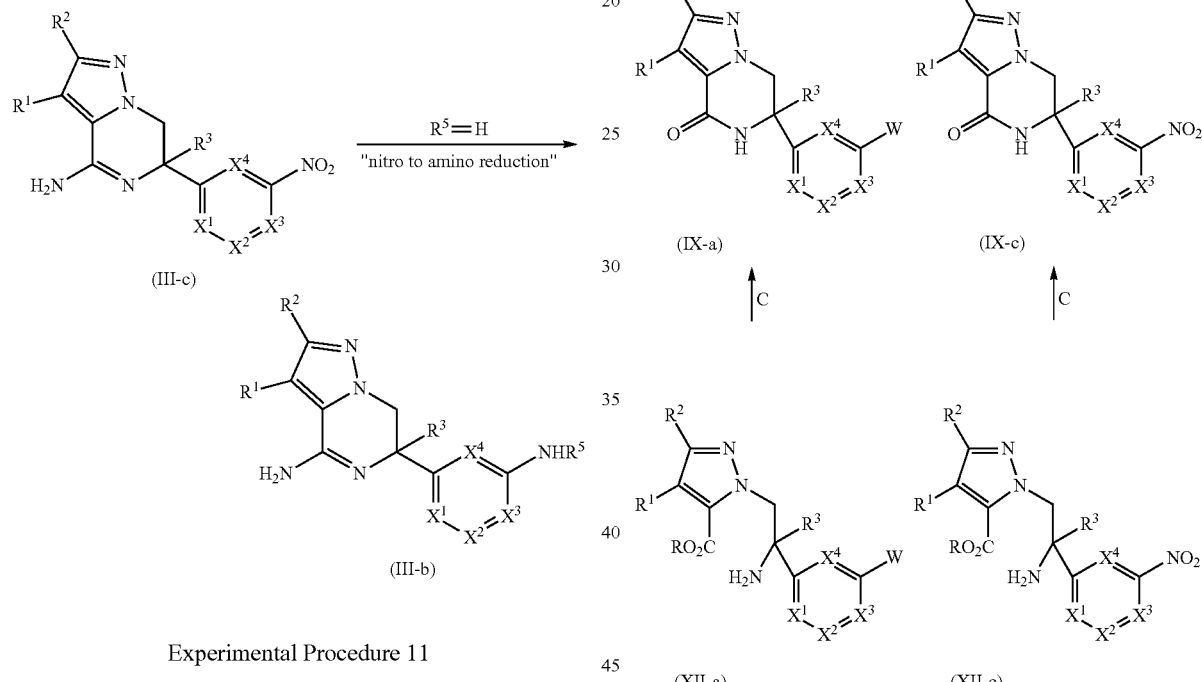

Experimental Procedure 11

The compounds of Formula (III-a) and (III-c) can generally be prepared following the reaction steps shown in the reaction schemes (11) and (12) below.

Reaction Scheme 11

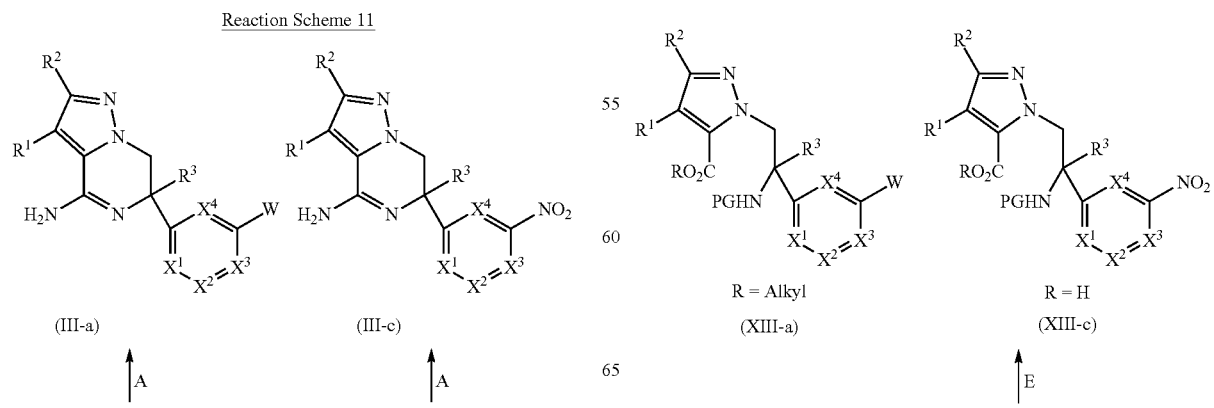

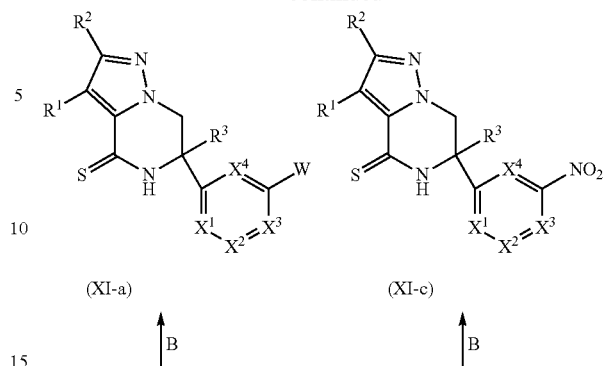

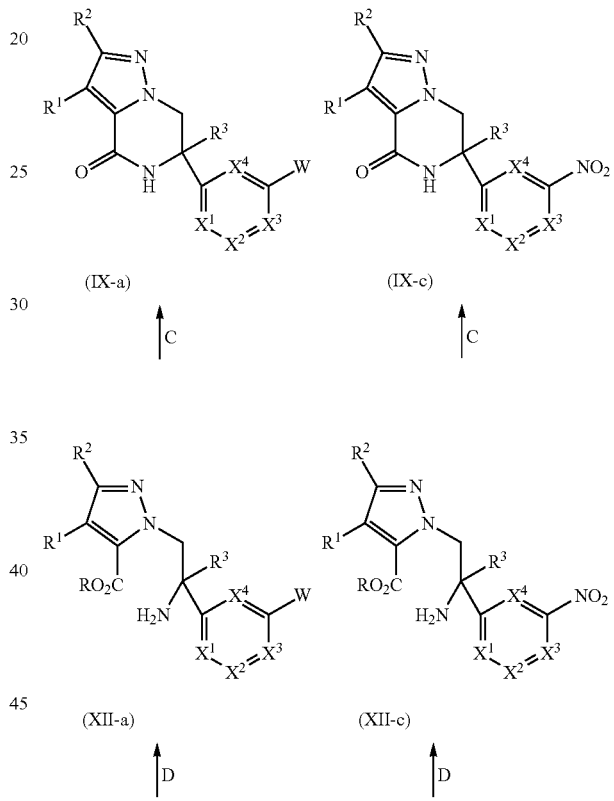

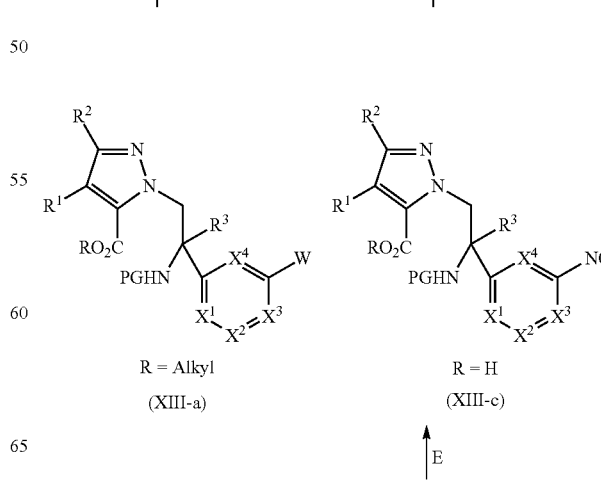

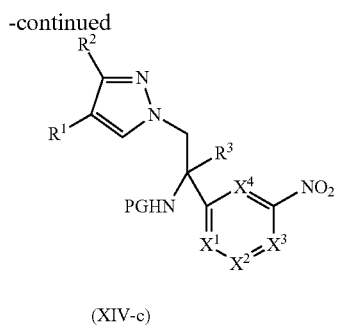

(XIV-c)

A: Thioamide-to-amidine conversion
B: Amide-to-thioamide conversion (thionation)
C: Cyclization
D: Removing any N-protecting groups
E: Metalation The amidine derivatives in the above reaction scheme (11) may be conveniently prepared from the corresponding thioamide derivatives following art-known thioamide-to-amidine conversion procedures (reaction step A). Said conversion may conveniently be conducted by treatment of the said thioamides with an ammonia source such as, for example, ammonium chloride or aqueous ammonia, in a suitable reaction-inert solvent such as, for example, water or methanol and the like, under thermal conditions such as, for example, heating the reaction mixture at 60 to 90° C., for example for 6 to 100 hours.

The thioamide derivatives in the above reaction scheme (11) can be prepared from amide derivatives following art-known thionation procedures (reaction step B). Said conversion may conveniently be conducted by treatment of the said amides with a thionation agent such as, for example, phosphorous pentasulfide or 2,4-bis-(4-methoxy-phenyl)-1,3-dithia-2,4-diphosphetane 2,4-disulfide [Lawesson's reagent], under neat conditions or in a reaction inert solvent such as, for example, tetrahydrofuran or 1,4-dioxane and the like, optionally in the presence of a suitable base like pyridine under thermal conditions such as, for example, heating the reaction mixture at 50 to 100° C., for example for 24 hours.

The amide derivatives of Formula (IX-a) and (IX-c) in the above reaction scheme (11) can be prepared from the corresponding intermediate compounds of Formula (XII-a) and (XII-c) following art-known cyclization procedures (reaction step C). Said cyclization may conveniently be conducted by treatment of intermediate compounds of Formula (XII-a) and (XII-c) with a suitable base, such as potassium acetate, in a suitable reaction solvent, such as for example ethanol and the like, at 70° C. to 100° C., for a period of time to ensure the completion of the reaction.

The intermediates of Formula (IX-a), wherein $R^2$ is hydrogen, can be prepared from an intermediate of Formula (IX-a-1), wherein $R^2$ is nitro, by reduction of the nitro to the amino group, followed by a diazotization-deamination reaction.

The intermediates of Formula (IX-a), wherein $R^2$ is difluoromethyl, can be prepared from an intermediate of Formula (IX-a-2), wherein $R^2$ is alkoxycarbonyl, by conversion of the ester group into an aldehyde by one of the several methods known to the person skilled in the art, followed by reaction of the aldehyde group with DAST.

The intermediate compounds of Formula (XII-a) and (XII-c) in the above reaction scheme (II) can be prepared from the corresponding intermediate compounds of Formula (XIII-a) and (XIII-c) by removal of the protecting group being carried out according to processes known to the person skilled in the art (reaction step D).

The intermediate compound of Formula (XIII-c) in the above reaction scheme (II) can be prepared from the corresponding intermediate compounds of Formula (XIV-c) following art-known metalation procedures (reaction step E). Said metalation may conveniently be conducted by treatment of intermediate compounds of Formula (XIV-c) with a suitable base, such as lithium diisopropylamide, and a suitable electrophile such as dry ice or ethyl chloroformate, in a suitable reaction solvent, such as for example tetrahydrofuran, at −80° C. to 0° C., for a period of time to ensure the completion of the reaction.

Reaction Scheme 12

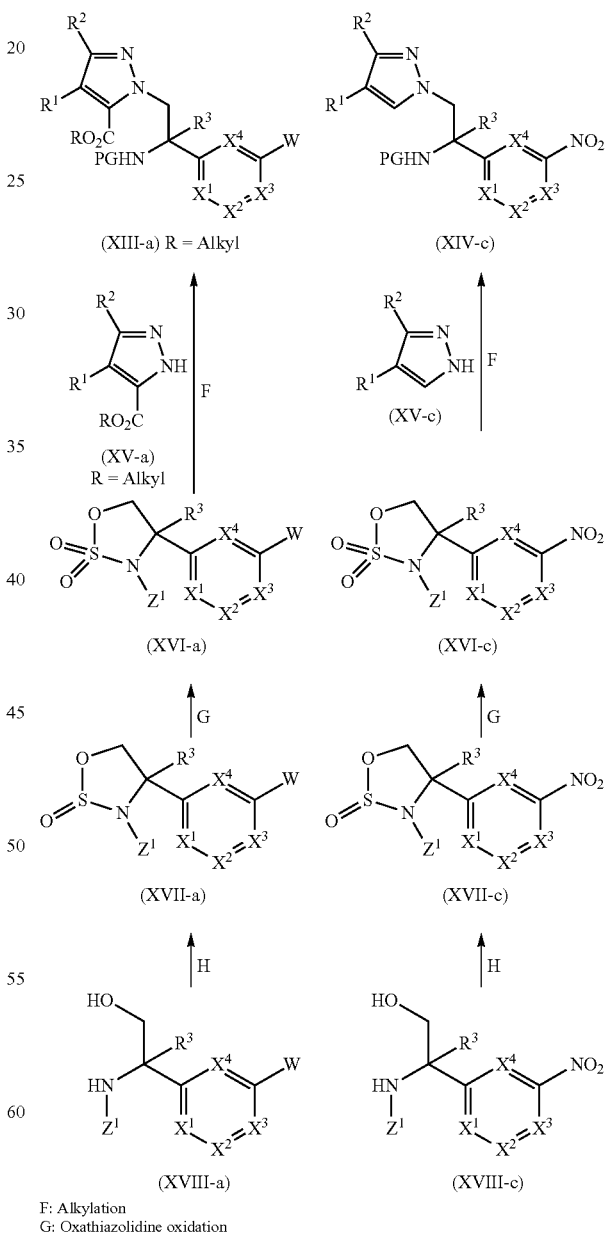

F: Alkylation
G: Oxathiazolidine oxidation
H: Oxathiazolidine formation

The intermediates according to Formula (XIII-a) and (XIV-c) in the above reaction scheme (12) can be prepared from the corresponding intermediate compounds of Formula (XVI-a) and (XVI-c), wherein $Z^1$ is a protecting group of amines such as, for example, the tert-butoxycarbonyl group, following art-known alkylation procedures (reaction step F). Said alkylation may conveniently be conducted by treatment of (XV-a) and (XV-c) respectively with the corresponding intermediate compounds of Formula (XVI-a) and (XVI-c) with a suitable base such as, for example, sodium carbonate or cesium carbonate, in a suitable inert solvent such as, for example, N,N-dimethyl formamide or dimethoxysulfoxide, at low temperature such as, for example, 0° C. for 30 min and then at a moderately high temperature such as, for example, 100° C. for 24 hours to 100 hours or for example, heating the reaction mixture at 130° C., for example for 30 min to 45 min under microwave irradiation.

The intermediates according to Formula (XVI-a) and (XVI-c) in the above reaction scheme (12) can be prepared by reacting the intermediate compounds of Formula (XVII-a) and (XVII-c) following art-known oxidation procedures (reaction step G). Said oxidation may conveniently be conducted by treatment of the corresponding intermediate compounds of Formula (XVII-a) and (XVII-c) with an oxidant agent such as, for example, sodium periodate in a suitable inert solvent such as, for example, acetonitrile/water, in the presence of ruthenium (III) chloride at a moderately high temperature such as, for example, 25° C., for example for 2 hours.

The intermediates according to Formula (XVII-a) and (XVII-c) in the above reaction scheme (12) can be prepared by reacting the intermediate compounds of Formula (XVIII-a) and (XVIII-c) following art-known sulfamidate formation procedures (reaction step H). Said transformation may conveniently be conducted by treatment of the corresponding intermediate compounds of Formula (XVIII-a) and (XVIII-c) with thionyl chloride, in the presence of a base such as, for example, pyridine, in a suitable reaction-inert solvent, such as, for example, acetonitrile, at low temperature such as, for example, −40° C., for example for 30 min and then at a moderately high temperature such as, for example, 25° C., for example for 24 to 72 hours.

The intermediates compounds of Formula (XVIII-a) and (XVIII-c), wherein $Z^1$ is a protecting group of amines such as, for example, the tert-butoxycarbonyl group, can generally be prepared following art-known Strecker type procedures described in literature.

Pharmacology

The compounds of the present invention and the pharmaceutically acceptable compositions thereof inhibit BACE and therefore may be useful in the treatment or prevention of Alzheimer's Disease (AD), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid.

The invention relates to a compound according to the general Formula (I), a stereoisomeric form thereof or a pharmaceutically acceptable acid or base addition salt or a solvate thereof, for use as a medicament.

The invention also relates to a compound according to the general Formula (I), a stereoisomeric form thereof or a the pharmaceutically acceptable acid or base addition salt or a solvate thereof, for use in the treatment or prevention of diseases or conditions selected from the group consisting of AD, MCI, senility, dementia, dementia with Lewy bodies, cerebral amyloid angiopathy, multi-infarct dementia, Down's syndrome, dementia associated with Parkinson's disease and dementia associated with beta-amyloid.

The invention also relates to the use of a compound according to the general Formula (I), a stereoisomeric form thereof or a pharmaceutically acceptable acid or base addition salt or a solvate thereof, for the manufacture of a medicament for the treatment or prevention of any one of the disease conditions mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof, a pharmaceutically acceptable addition salt or solvate thereof, to a warm-blooded animal, including a human.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

Pharmaceutical Compositions

The present invention also provides compositions for preventing or treating diseases in which inhibition of beta-secretase is beneficial, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The following examples are intended to illustrate but not to limit the scope of the present invention.

Experimental Part

Hereinafter, the term "AcOH" means acetic acid, "HCl" means hydrochloric acid, "AcOEt" means ethylacetate, "DCM" means dichloromethane, "DIPE" means diisopropylether, "DMF" means N,N-dimethylformamide, "$CO_2$" means carbon dioxide, "DMSO" means dimethylsulfoxide, "$Et_2O$" means diethylether, "$Et_3N$" means triethylamine, "EtOH" means ethanol, "iPrOH" means isopropanol, "$iPrNH_2$" means isopropylamine, "MeCN" means acetonitrile, "MeOH" means methanol, "NaOH" means sodium hydroxide, "$NH_4Cl$" means ammonium chloride, "$NH_3$" means ammonia, "$NaHCO_3$" means sodium bicarbonate, "$NaHSO_4$" means sodium hydrogenosulfate, "$Na_2CO_3$" means sodium carbonate, "$Na_2SO_4$" means sodium sulphate, "$H_2SO_4$" means sulphuric acid, "$MgSO_4$" means magnesium sulphate, "CuI" means copper iodide, "TFA" means trifluoromethansulfonic acid, "$RuO_2$" means ruthenium oxide, "DAST" means diethylaminosulfur trifluoride, "DBU" means 1,8-diazabicyclo[5.4.0]undec-7-ene, "$N_2$" means nitrogen, "$CO_2$" means carbon dioxide, "aq." means aqueous, "min" means minutes, "m.p." means melting point, "rac" means racemic, "$R_t$" means retention times, "THF" means tetrahydrofuran, "SFC" means supercritical fluid chromatography.

Microwave assisted reactions were performed in a single-mode reactor: Emrys™ Optimizer microwave reactor (Personal Chemistry A.B., currently Biotage).

Hydrogenation reactions were performed in a continuous flow hydrogenator H-CUBE® from ThalesNano Nanotechnology Inc.

Thin layer chromatography (TLC) was carried out on silica gel 60 F254 plates (Merck) using reagent grade solvents. Open column chromatography was performed on silica gel, particle size 60 Å, mesh=230-400 (Merck) under standard techniques. Flash column chromatography was performed using ready-to-connect cartridges from Merck, on irregular silica gel, particle size 15-40 μm (normal layer disposable flash columns) on an SPOT or LAFLASH system from Armen Instrument.

Optical rotations were measured on a Perkin-Elmer 341 polarimeter with a sodium lamp and reported as follows: [α]° (λ, c g/100 ml, solvent, T° C.).

Flow reactions were performed in a commercially available Vapourtec R2+R4 modular device.

For key intermediates, as well as some final compounds, the absolute configuration of chiral centers (indicated as R and/or S) were established via comparison with samples of known configuration, or the use of analytical techniques suitable for the determination of absolute configuration, such as VCD (vibrational cicular dichroism) or X-ray crystallography. When the absolute configuration at a chiral center is unknown, it is arbitrarily designated R*.

A. Preparation of the Intermediates

Example A1

Preparation of Intermediate A1:
rac-2-amino-2-(3-bromo-phenyl)-propionitrile

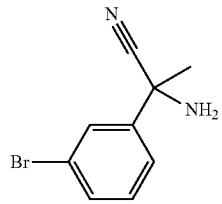

Trimethylsilylcyanide (20 g, 200 mmol) was added to a stirred solution of 3-bromo-acetophenone (20 g, 100 mmol) and NH$_4$Cl (11 g, 200 mmol) in NH$_3$/MeOH (400 mL). The mixture was stirred at room temperature for 4 days. The solvent was evaporated in vacuo and the residue was taken up in AcOEt (100 mL). The solid was filtered off and the filtrate was evaporated in vacuo to yield intermediate A1 (20 g, 86% yield), that was used in the next step without further purification.

Example A2

Preparation of Intermediate A2:
rac-2-amino-2-(3-bromo-phenyl)-propionic acid methyl ester

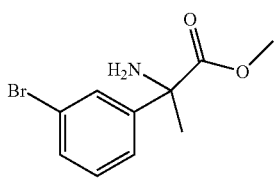

Intermediate A1 (20 g, 88.9 mmol) was dissolved in HCl/MeOH (500 mL). The mixture was refluxed for 4 days. After cooling to room temperature, AcOEt (100 mL) and H$_2$O (100 mL) were added and the mixture was extracted with AcOEt (2×100 mL). The combined aqueous layers were basified with an NH$_3$ solution to pH=8 and extracted with AcOEt (5×100 mL). The combined organic layers were dried (Na$_2$SO$_4$), filtered and the solvents evaporated in vacuo to yield intermediate A2 (10.6 g, 46% yield) as an oil. LCMS: 258 [M+H]$^+$; R$_t$: 3.77 min (method 7).

The following intermediate was prepared according to the synthetic procedures described in examples A1-A2:

Example A3

Preparation of Intermediate A3:
rac-2-amino-2-(3-nitro-phenyl)-propionic acid methyl ester

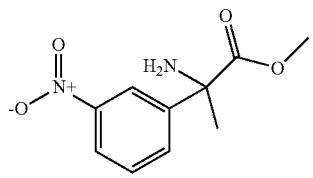

From rac-2-amino-2-(3-nitro-phenyl)-propionitrile. Flash column chromatography (silica gel; AcOEt/petroleum ether) to yield intermediate 3 (63%). LCMS: 225 [M+H]$^+$; R$_t$: 0.98 min (method 9).

Example A4

Preparation of Intermediate A4: rac-2-amino-2-(3-bromo-phenyl)-propan-1-ol

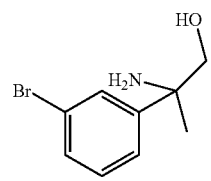

Lithium aluminium hydride (1 M in THF; 22 mL, 22 mmol) was added dropwise to a stirred solution of intermediate A2 (7.5 g, 29.1 mmol) in THF (200 mL) at −15° C. The mixture was left warming up slowly to 0° C. during 1 hour. More THF (150 mL) was added and a saturated solution of Na$_2$SO$_4$ was added dropwise until no more hydrogen was formed. Anhydrous Na$_2$SO$_4$ was added and left stirring overnight at room temperature. The mixture was filtered over diatomaceous earth, washed with THF and the solvent evaporated in vacuo. The crude product was purified by flash column chromatography (silica gel; 7 M solution of NH$_3$ in MeOH/DCM). The desired fractions were collected and the solvents evaporated in vacuo to yield intermediate A4 (5.70 g, 85% yield) as an oil. LCMS: 230 [M+H]$^+$; R$_t$: 0.69 min (method 1).

Example A5

Preparation of Intermediate A5: rac-2-amino-2-(3-nitro-phenyl)-propan-1-ol

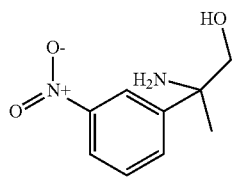

Sodium borohydride (16.3 g, 429.4 mmol) was added portionwise to a stirred solution of intermediate A3 (48.3 g, 214.7 mmol) in MeOH (500 mL). The mixture was stirred at room temperature for 10 hours. The solvent was evaporated in vacuo. The residue was basified with a saturated aqueous solution of $NaHCO_3$ to pH=9 and extracted with AcOEt (3×200 mL). The organic layers were dried ($Na_2SO_4$), filtered and the solvents evaporated in vacuo to yield intermediate A5 (30.26 g, 72% yield). LCMS: 197 $[M+H]^+$; $R_t$: 3.16 min (method 8); m.p. 238.7-241.6° C. (WRS-2A).

Example A6

Preparation of Intermediate A6: (R)-2-amino-2-(3-bromo-phenyl)-propan-1-ol

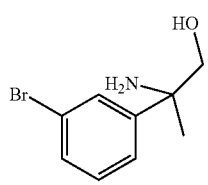

A sample of intermediate A4 (15.4 g) was separated into the corresponding enantiomers by preparative SFC on (Chiralpak® Daicel AD×250 mm). Mobile phase ($CO_2$, MeOH with 0.2% $iPrNH_2$) to yield intermediate A6 (7.21 g, 40% yield). LCMS: 230 $[M+H]^+$; $R_t$: 0.71 min (method 1); $\alpha_D$: −14.9° (589 nm, c 0.2946 w/v %, MeOH, 20° C.).

Example A7

Preparation of Intermediate A7: (R)-[1-(3-bromo-phenyl)-2-hydroxy-1-methyl-ethyl]-carbamic acid tert butyl ester

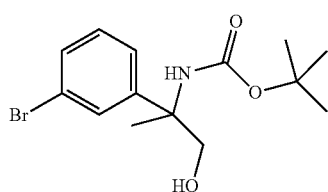 [SMILES: CC(C)(C)OC(=O)NC(C)(CO)c1cccc(Br)c1]

Di-tert-butyldicarbonate (19.8 g, 90.7 mmol) was added portionwise to a stirred solution of intermediate A6 (11.6 g, 50.4 mmol) in a mixture of saturated solution of $NaHCO_3$ (100 mL) and THF (100 mL) at 0° C. The mixture was stirred at 0° C. for 10 min and at room temperature for 15 hours. The mixture was cooled in an ice/$H_2O$ bath and acidified with stirring to pH=1-2 with $NaHSO_4$. The organic layer was separated and the aq. layer was further extracted with AcOEt. The combined organic layers were separated, dried ($MgSO_4$), filtered and the solvents evaporated in vacuo. The crude product was purified by short column chromatography (silica gel; AcOEt/DCM). The desired fractions were collected and concentrated in vacuo to yield intermediate A7 (16.47 g, 99% yield) as a colorless oil that solidified upon standing. LCMS: 330 $[M+H]^+$; $R_t$: 2.58 min (method 1).

Example A8

Preparation of Intermediate A8: (R)-[3-(tert-butyloxycarbonyl)-4-(3-bromo-phenyl)-4-methyl-[1,1,3] oxathiazolidine-2-oxide

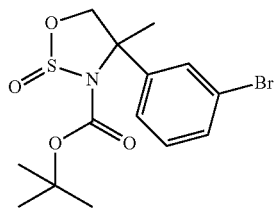 [SMILES: CC(C)(C)OC(=O)N1S(=O)OCC1(C)c1cccc(Br)c1]

A solution of intermediate A7 (14.3 g, 43.3 mmol) in dry MeCN (80 mL) was added dropwise to a stirred solution of thionyl chloride (7.9 mL, 108.3 mmol) in dry MeCN (226 mL) cooled to −40° C. and under a $N_2$ atmosphere. The reaction mixture was stirred for 30 min at −40° C. before pyridine (17.4 mL, 216.5 mmol) was added. The reaction was allowed to warm to room temperature and stirred for 64 hours. The solvents were evaporated in vacuo. The residue was treated with $Et_2O$. The solids were filtered and the filtrate concentrated in vacuo to yield intermediate A8 (15.5 g, 95% yield) as a red oil. The product was used in the next reaction without further purification. LCMS: 393 $[M+NH_4]^+$; $R_t$: 3.4 min (method 1).

Example A9

Preparation of Intermediate A9: (R)-[3-(tert-butyloxycarbonyl)-4-(3-bromo-phenyl)-4-methyl-[1,1,3] oxathiazolidine-2,2-dioxide

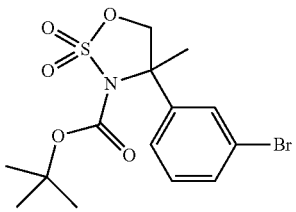 [SMILES: CC(C)(C)OC(=O)N1C(C)(c2cccc(Br)c2)COS1(=O)=O]

Ruthenium (III) chloride (85 mg, 0.41 mmol) was added to solution of intermediate A8 (15.3 g, 40.8 mmol) in a mixture of MeCN and $H_2O$ (1:1) (438 mL) at 0° C., followed by the addition of sodium periodate (13.1 g, 61.2 mmol). The reaction was allowed to warm to room temperature and stirred for 2 hours. The mixture was filtered through diatomaceous earth and washed with AcOEt (125 mL). H₂O (125 mL) and AcOEt (250 mL) were added to the filtrate. The organic layer was separated, dried (MgSO₄), filtered and the solvents evaporated in vacuo. The product was purified by flash column chromatography (silica gel; DCM). The desired fractions were collected and the solvents evaporated in vacuo to yield intermediate A9 (14.4 g, 90% yield) as a white solid. LCMS: 409 [M+NH₄]⁺; R$_t$: 3.3 min (method 1); m.p. 133.1° C. (FP90); α$_D$: −35.6° (589 nm, c 0.55 w/v %, DMF, 20° C.).

The following intermediate was prepared according to the synthetic procedures described in examples A7-A9:

Example A10

Preparation of Intermediate A10: rac-[3-(tert-butyloxycarbonyl)-4-(3-nitro-phenyl)-4-methyl-[1,1,3]oxathiazolidine-2,2-dioxide

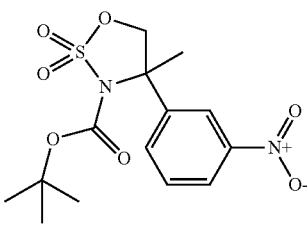 [SMILES: CC(C)(C)OC(=O)N1C(C)(c2cccc([N+](=O)[O-])c2)COS1(=O)=O]

Prepared from rac-[3-(tert-butyloxycarbonyl)-4-(3-nitrophenyl)-4-methyl-[1,1,3]oxathiazolidine-2-oxide. Flash column chromatography (silica gel; DCM) to yield intermediate A10 as a yellow solid (95%). LCMS: 376 [M+NH₄]⁺; R$_t$: 1.35 min (method 2).

Example A1

Preparation of Intermediate A11: 2-[2-(3-bromo-phenyl)-2R-tert-butoxycarbonyl-amino-propyl]-2H-pyrazole-3-carboxylic acid ethyl ester

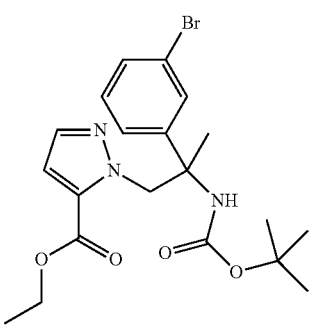 [SMILES: CCOC(=O)c1ccnn1CC(C)(NC(=O)OC(C)(C)C)c1cccc(Br)c1]

Cesium carbonate (824 mg, 2.53 mmol) was added to a mixture of intermediate A9 (0.661 g, 1.69 mmol) and 2H-pyrazole-3-carboxylic acid ethyl ester (260 mg, 1.86 mmol) in DMSO (8 mL) at room temperature. The mixture was stirred at room temperature for 30 min and at 110° C. for 3 hours. The mixture was treated with a saturated solution of citric acid and DCM (20 mL) and stirred for 2 hours. The organic phase was separated and treated with H₂O (10 mL) and extracted with DCM (2×10 mL). The organic layer was separated, dried (MgSO₄), filtered and the solvents evaporated in vacuo. The crude product was purified by flash column chromatography (silica gel; DCM). The desired fractions were collected and the solvents evaporated in vacuo to yield intermediate A11 (186 mg, 24% yield) as a colorless oil. LCMS: 452 [M+H]⁺; R$_t$: 4.23 min (method 3).

Example A12

Preparation of Intermediate A12: rac-[2-(4-bromo-pyrazol-1-yl)-1-methyl-1-(3-nitro-phenyl)-ethyl]-carbamic acid tert-butyl ester

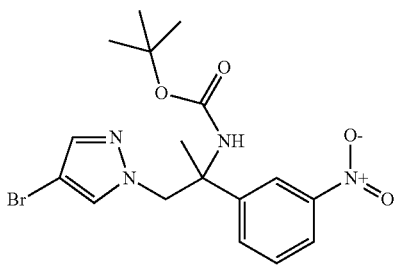 [SMILES: CC(C)(C)OC(=O)NC(C)(Cn1cc(Br)cn1)c1cccc([N+](=O)[O-])c1]

Sodium carbonate (59 mg, 0.56 mmol) was added to a mixture of intermediate A10 (100 mg, 0.28 mmol) and 4-bromo-1H-pyrazole (53 mg, 0.36 mmol) in DMF (3 mL). The mixture was stirred at 130° C. for 2 hours. The solvent was evaporated in vacuo. The residue was treated with H₂O (2 mL) and extracted with DCM (2×10 mL). The organic layer was separated, dried (MgSO₄), filtered and the solvents evaporated in vacuo. The crude product was purified by flash column chromatography (silica gel; DCM). The desired fractions were collected and the solvents evaporated in vacuo to yield intermediate A12 (100 mg, 84% yield) as a white solid after treatment with cold Et₂O. LCMS: 425 [M+H]⁺; R$_t$: 3.57 min (method 3); m.p. 159.3° C. (FP 90).

Example A13

Preparation of Intermediate A13: (R)-2-[2-amino-2-(3-bromo-phenyl)-propyl]-2H-pyrazole-3-carboxylic acid ethyl ester

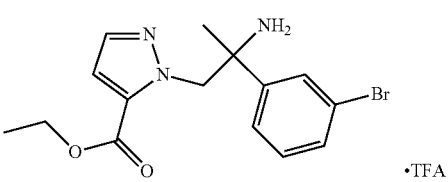 [SMILES: CCOC(=O)c1ccnn1CC(C)(N)c1cccc(Br)c1]

Trifluoroacetic acid (1 mL) was added to a stirred solution of intermediate A11 (186 mg, 0.41 mmol) in DCM (5 mL) at 0° C. The mixture was stirred at room temperature for 2 hours. The solvents were evaporated in vacuo to yield intermediate A13 (180 mg, 94% yield) as a colorless oil that was used in the next step without further purification. LCMS: 352 [M+H]⁺; R$_t$: 2.69 min (method 3).

Example A14

Preparation of Intermediate A14: rac-4-bromo-2-[2-tert-butoxycarbonylamino-2-(3-nitro-phenyl)-propyl-2H-pyrazole-3-carboxylic acid

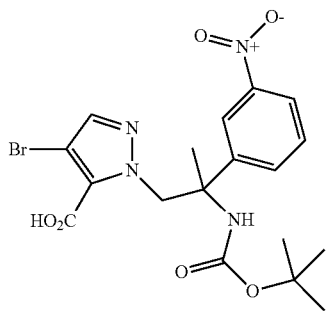 [SMILES: CC(C)(C)OC(=O)NC(C)(Cn1ncc(Br)c1C(=O)O)c1cccc([N+](=O)[O-])c1]

A 2 M solution of lithium diisopropylamide in THF and heptane (0.25 mL, 0.49 mmol) was added to a solution of intermediate A12 (100 mg, 0.24 mmol) in THF (3 mL) at −78° C. The reaction mixture was stirred at −78° C. for 1 hour. Dry ice was then added and the mixture was warm to room temperature over 2 hours. The mixture was treated with a saturated solution of NH₄Cl and extracted with DCM (3×10 mL). The organic layer was separated, dried, filtered and the solvents evaporated in vacuo. The crude product was purified by flash column chromatography (silica gel; MeOH/DCM). The desired fractions were collected and the solvents evaporated in vacuo to yield intermediate A14 (60 mg, 54% yield) as colourless oil. LCMS: 469 [M+H]⁺; R$_t$: 1.74 min (method 3).

Example A15

Preparation of Intermediate A15: (R)-6-(3-bromo-phenyl)-6-methyl-6,7-dihydro-5H-pyrazolo[1,5-a]pyrazin-4-one

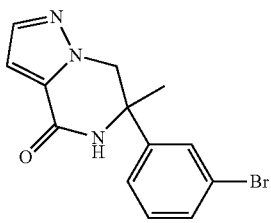 [SMILES: CC1(c2cccc(Br)c2)Cn2nccc2C(=O)N1]

Potassium acetate (83 mg, 0.85 mmol) was added to a solution of intermediate A13 (180 mg, 0.39 mmol) in EtOH (5 mL) at room temperature. The mixture was stirred at 90° C. for 5 hours. The solvent was evaporated in vacuo. The residue was treated with a 0.5 M aq. solution of HCl and extracted with DCM. The organic layer was separated, dried (MgSO₄), filtered and the solvents evaporated in vacuo. The crude product was purified by flash column chromatography (silica gel; MeOH/DCM). The desired fractions were collected and the solvents evaporated in vacuo to yield intermediate A15 (100 mg, 84% yield) as a colorless oil. LCMS: 306 [M+H]⁺; R$_t$: 2.01 min (method 4).

Example A16

Preparation of Intermediate A16: rac-3-bromo-6-methyl-6-(3-nitro-phenyl)-6,7-dihydro-5H-pyrazolo[1,5-a]pyrazin-4-one

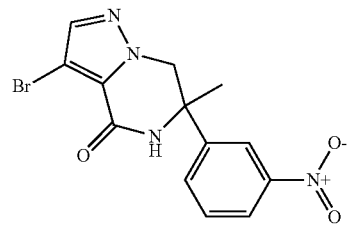 [SMILES: CC1(c2cccc([N+](=O)[O-])c2)Cn2ncc(Br)c2C(=O)N1]

Method A

Trifluoroacetic acid (3 mL) was added to a solution of intermediate A14 (200 mg, 0.4 mmol) in DCM (20 mL). The mixture was stirred at room temperature for 2 hours. Potassium acetate (59 mg, 0.06 mmol) in EtOH (3 mL) was then added. The mixture was stirred at 90° C. for 3 hours. The solvents were evaporated in vacuo. The crude was treated with a 1 M aq. solution of HCl (10 mL) and the product extracted with AcOEt (4×20 mL). The organic layer was separated, dried (MgSO₄), filtered and the solvents evaporated in vacuo. The crude product was purified by flash column chromatography (silica gel; MeOH/DCM). The desired fractions were collected and the solvents evaporated in vacuo to yield intermediate A16 (120 mg, 19% yield) as a white solid. LCMS: 351 [M+H]⁺; R$_t$: 2.45 min (method 5); m.p. 285.3° C. (FP 90).

Method B

Trifluoroacetic acid (100 mL) was added to a stirred solution of intermediate A23 (6.5 g, 13.07 mmol) in DCM (200 mL) at room temperature. The mixture was stirred at room temperature for 3 hours. The solvent was evaporated in vacuo, then potassium acetate (1.924 g, 19.60 mmol.) and EtOH (100 mL) were added, and the reaction stirred at reflux for 4 hours. The crude was evaporated in vacuo and the residual treated with a 1 M aq. solution of HCl to pH=3. The crude was extracted with AcOEt (3×50 ml), the organic phase was evaporated to dryness and the crude treated with cold EtOH and Et₂O to afford intermediate A16 as a beige solid. The combined solvents were evaporated in vacuo and purified by column chromatography (silica gel; MeOH/DCM). The desired fractions were collected and the solvents evaporated in vacuo to afford an additional batch of intermediate A16 as a white solid (combined amount 4 g, 87%). LCMS: 351 [M+H]⁺; R$_t$: 1.65 min (method 3).

Example A17

Preparation of Intermediate A17: (R)-6-[3-(5-chloro-pyridin-3-yl)-phenyl]-6-methyl-6,7-dihydro-5H-pyrazolo[1,5-a]pyrazin-4-one

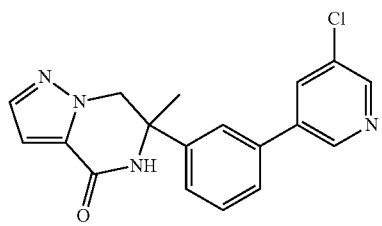

Tetrakis(triphenylphosphine)palladium(0) (34 mg, 0.029 mmol) was added to a stirred suspension of intermediate A15 (90 mg, 0.29 mmol) and 5-chloropyridine-3-boronic acid (55 mg, 0.35 mmol) in a mixture of 1,4-dioxane (5 mL) and a saturated solution of $Na_2CO_3$ (3 mL) at room temperature under $N_2$. The mixture was stirred at 150° C. for 15 min under microwave irradiation. After cooling to room temperature, the mixture was diluted with $H_2O$ and extracted with DCM. The organic layer was separated, dried ($MgSO_4$), filtered and the solvents evaporated in vacuo. The crude product was purified by flash column chromatography (silica gel; MeOH/DCM). The desired fractions were collected and the solvents evaporated in vacuo and washed with cold EtOH and $Et_2O$ to yield intermediate A17 (81 mg, 81% yield) as a white solid. LCMS: 339 [M+H]$^+$; $R_t$: 0.89 min (method 2).

Example A18

Preparation of Intermediate A18: (R)-6-[3-(5-chloro-pyridin-3-yl)-phenyl]-6-methyl-6,7-dihydro-5H-pyrazolo[1,5-a]pyrazine-4-thione

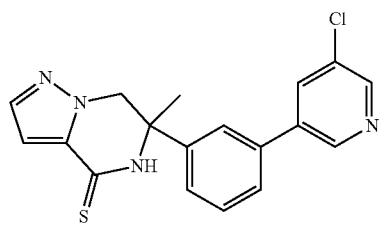 [SMILES: CC1(c2cccc(-c3cncc(Cl)c3)c2)Cn2nccc2C(=O)N1]

Phosphoruspentasulfide (71 mg, 0.32 mmol) was added to a solution of intermediate A17 (90 mg, 0.27 mmol) in pyridine (4 mL) and the mixture was heated at 100° C. for 5 hours. The solvent was evaporated in vacuo and the crude product was purified by short column chromatography (silica gel; MeOH/DCM). The desired fractions were collected and the solvents evaporated in vacuo to yield intermediate A18 (60 mg, 63% yield) as a yellow oil. LCMS: 355 [M+H]$^+$; $R_t$: 2.4 min (method 3).

The following intermediates were prepared according to the synthetic procedure described in example A18:

Example A19

Preparation of Intermediate A19: rac-3-bromo-6-methyl-6-(3-nitro-phenyl)-6,7-dihydro-5H-pyrazolo[1,5-a]pyrazine-4-thione

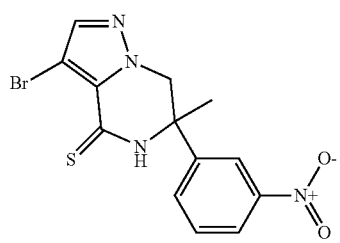 [SMILES: CC1(c2cccc([N+](=O)[O-])c2)Cn2ncc(Br)c2C(=S)N1]

Prepared from intermediate A16. Flash column chromatography (silica gel; MeOH/DCM) to yield intermediate A19 as a yellow solid (87%). LCMS: 366 [M+H]$^+$; $R_t$: 2.37 min (method 3).

Example A20

Preparation of Intermediate A20: rac-6-(3-aminophenyl)-3-bromo-6-methyl-6,7-dihydro-pyrazolo[1,5-a]pyrazin-4-ylamine

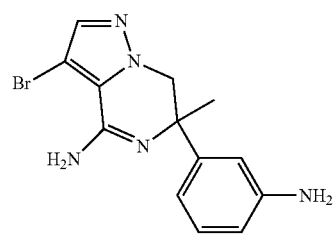

32% Aq. $NH_3$ solution (3 mL) was added to a stirred mixture of intermediate A19 (600 mg, 1.63 mmol) in a 7 M solution of $NH_3$ in MeOH (5 mL) in a sealed tube. The mixture was stirred at 60° C. for 4 hours. After cooling to room temperature the solvents were evaporated in vacuo. The crude product was dissolved in EtOH (20 mL) and tin(II) chloride (372 mg, 1.96 mmol) was added. The mixture was stirred at 90° C. for 24 hours. After cooling to room temperature, the mixture was filtered through celite and the solvent evaporated in vacuo. The residue was treated with an 8% aq. solution of NaOH (10 mL) and extracted with DCM (30 mL). The mixture was stirred at room temperature for 1 hour. The organic layer was separated, dried ($Na_2SO_4$), filtered and the solvents evaporated in vacuo. The crude product was purified by flash column chromatography (silica gel; 7 M solution of $NH_3$ in MeOH/DCM). The desired fractions were collected and the solvents evaporated in vacuo to yield intermediate A20 (200 mg, 38% yield) as a yellow oil. LCMS: 320 [M+H]$^+$; $R_t$: 1.5 min (method 6).

Example A21

Preparation of Intermediate A20: rac-6-(3-aminophenyl)-3-bromo-6-methyl-6,7-dihydro-pyrazolo[1,5-a]pyrazin-4-ylamine and Intermediate A21: rac-3-bromo-6-methyl-6-(3-nitro-phenyl)-6,7-dihydro-pyrazolo[1,5-a]pyrazin-4-ylamine

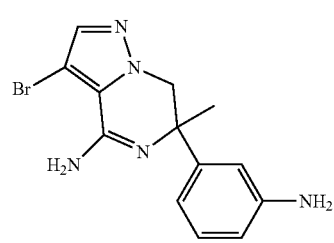 [SMILES: CC1(c2cccc(N)c2)Cn2ncc(Br)c2C(N)=N1]

-continued

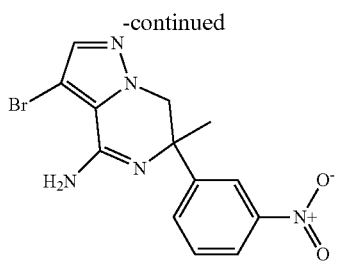

32% Aq. NH₃ solution (4 mL) was added to a stirred mixture of intermediate A19 (3.8 g, 10.35 mmol) in a 7 M solution of NH₃ in MeOH (6 mL) in a sealed tube. The mixture was stirred at 100° C. for 6 hours. After cooling to room temperature the solvents were evaporated in vacuo. The crude product was purified by flash column chromatography (silica gel; MeOH/DCM). The desired fractions were collected and the solvents evaporated in vacuo and the crude product was purified by flash column chromatography (silica gel; 7 M solution of NH₃ in MeOH/DCM). The desired fractions were collected and the solvents evaporated in vacuo to yield intermediate 20 (100 mg, 3% yield), intermediate 21 (200 mg, 6% yield) and a fraction containing a mixture of intermediate 20 and 21 (2.5 g). LCMS: A20: 322 [M+H]⁺, $R_t$: 0.87 min (method 3); A21: 350 [M+H]⁺; $R_t$: 0.95 min (method 2)

Example A22

Preparation of Intermediate A22: rac-6-(3-aminophenyl)-6-methyl-6,7-dihydro-pyrazolo[1,5-a]pyrazin-4-ylamine

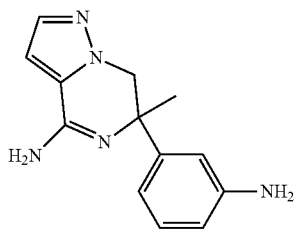 [SMILES: CC1(c2cccc(N)c2)Cn2nccc2C(N)=N1]

Method A

A solution of intermediate A20 (200 mg, 0.62 mmol) in MeOH (30 mL) and Et₃N (5 mL) was hydrogenated in a H-Cube reactor (1.2 mL/min, 30 mm palladium on carbon 10% cartridge, full hydrogen mode, 50° C., 3 cycles). The solvents were concentrated in vacuo. The crude product was purified by flash column chromatography (silica gel; 7 M solution of NH₃ in MeOH/DCM). The desired fractions were collected and the solvents evaporated in vacuo to yield intermediate 22 (100 mg, 66% yield) as a white solid. LCMS: 415 [M+H]⁺; $R_t$: 1.58 min (method 3).

Method B

Zinc (1.33 g, 20.40 mmol) was added to the fraction containing a mixture of intermediates 20 and 21 described in Example A21 (2.5 g, 7.46 mmol) in EtOH (100 mL) and AcOH (20 mL). The mixture was stirred at reflux for 24 hours. After cooling to room temperature the mixture was filtered through celite and the solvents evaporated in vacuo. The crude product was purified by flash column chromatography (silica gel; 7 M solution of NH₃ in MeOH/DCM). The desired fractions were collected and the solvents evaporated in vacuo to yield intermediate 22 (0.93 g, 52% yield) as a yellow oil that precipitates upon standing.

The following intermediates were prepared according to the synthetic procedure described in example A14, using ethyl chloroformate instead of dry ice:

Example A23

Preparation of Intermediate A23: rac-4-bromo-2-[2-tert-butoxycarbonylamino-2-(3-nitrophenyl)-propyl]-2H-pyrazole-3-carboxylic acid ethyl ester

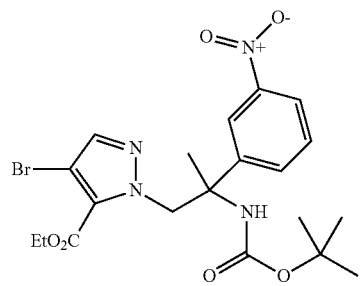 [SMILES: CCOC(=O)c1c(Br)cnn1CC(C)(NC(=O)OC(C)(C)C)c1cccc([N+](=O)[O-])c1]

Prepared from intermediate A12. Flash column chromatography (silica gel; AcOEt/heptane) to yield intermediate A23 (65%). LCMS: 499 [M+H]⁺; $R_t$: 4.09 min (method 3).

Example A24

Preparation of Intermediate A24: rac-[1-methyl-1-(3-nitro-phenyl)-2-(3-trifluoro-methylpyrazol-1-yl)-ethyl]-carbamic acid tert-butyl ester

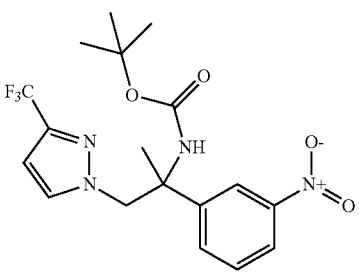 [SMILES: CC(C)(C)OC(=O)NC(C)(Cn1ccc(C(F)(F)F)n1)c1cccc([N+](=O)[O-])c1]

Intermediate A10 (2.5 g, 6.976 mmol) was added to a stirred solution of 3-(trifluoro-methyl)pyrazole (1.234 g, 9.069 mmol) and potassium carbonate (1.928 g, 13.952 mmol) in DMF (175 mL) at room temperature. The mixture was then heated at 110° C. for 2 hours. The solvent was evaporated and the residual treated with a saturated solution of citric acid (80 mL) and AcOEt (160 mL). The mixture was stirred for 1 hour at room temperature. The organic layer was separated, dried and evaporated in vacuo. The crude was purified by flash column chromatography (silica gel; DCM). The desired fractions were collected and evaporated in vacuo to yield a transparent oil, which, after treatment with cold Et₂O and standing, precipitated as a white solid (2 g, 69%).

Example A25

Preparation of Intermediate A25: rac-2-[2-tert-butoxycarbonylamino-2-(3-nitro-phenyl)-propyl]-5-trifluoromethyl-2H-pyrazole-3-carboxylic acid ethyl ester

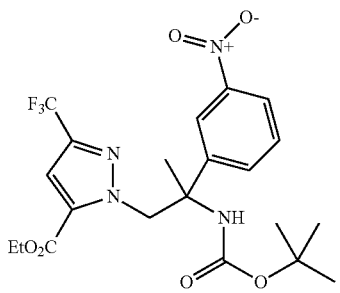 [SMILES: CCOC(=O)c1cc(C(F)(F)F)nn1CC(C)(NC(=O)OC(C)(C)C)c1cccc([N+](=O)[O-])c1]

Prepared from intermediate A24. Flash column chromatography (silica gel; AcOEt/heptane) to yield intermediate A25 (51%). LCMS: 487 [M+H]$^+$; R$_t$: 4.22 min (method 3).

The following intermediate was prepared according to the synthetic procedure described in example A16-Method B:

Example A26

Preparation of Intermediate A26: rac-6-methyl-6-(3-nitro-phenyl)-2-trifluoromethyl-6,7-dihydro-5H-pyrazolo[1,5-a]pyrazin-4-one

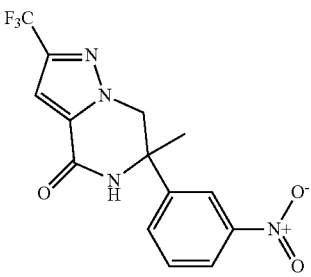 [SMILES: CC1(c2cccc([N+](=O)[O-])c2)Cn2nc(C(F)(F)F)cc2C(=O)N1]

Prepared from intermediate A25. Flash column chromatography (silica gel; MeOH/DCM) to yield intermediate A26 as a white solid (93%). LCMS: 339 [M–H]$^-$; R$_t$: 2.21 min (method 3). The following intermediate was prepared according to the synthetic procedure described in example A18-A21:

Example A27

Preparation of Intermediate A27: rac-6-methyl-6-(3-nitro-phenyl)-2-trifluoromethyl-6,7-dihydro-5H-pyrazolo[1,5-a]pyrazine-4-thione

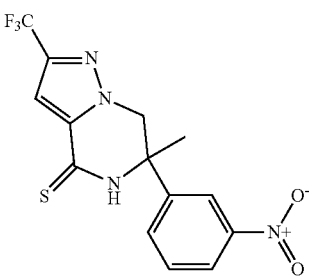 [SMILES: CC1(c2cccc([N+](=O)[O-])c2)Cn2nc(C(F)(F)F)cc2C(=S)N1]

Prepared from intermediate A26. Flash column chromatography (silica gel; MeOH/DCM) to yield intermediate A27 as a yellow solid (95%). LCMS: 355 [M–H]$^-$; R$_t$: 1.29 min (method 2).

Example A28

Preparation of Intermediate A28: rac-6-(3-aminophenyl)-6-methyl-2-trifluoromethyl-6,7-dihydro-pyrazolo[1,5-a]pyrazin-4-ylamine and Intermediate A29: 6-methyl-6-(3-nitro-phenyl)-2-t-rifluoromethyl-6,7-dihydro-pyrazolo[1,5-a]pyrazin-4-ylamine

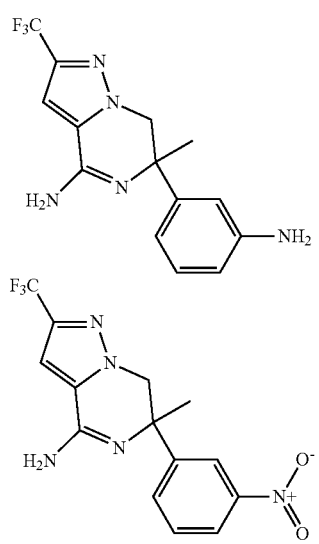

Prepared from intermediate A27. Flash column chromatography (silica gel; MeOH/DCM) to yield intermediate A28 (16%) and intermediate A29 (59%). LCMS: A28: 308 [M–H]$^-$; R$_t$: 0.77 min (method 2); A29: 338 [M–H]$^-$; R$_t$: 2.28 min (method 3),

Example A29

Preparation of Intermediate A28: rac-6-(3-aminophenyl)-6-methyl-2-trifluoromethyl-6,7-dihydro-pyrazolo[1,5-a]pyrazin-4-ylamine

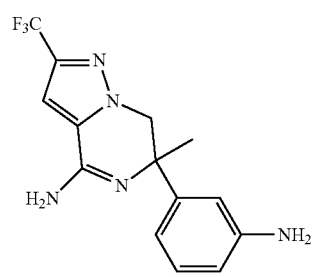 [SMILES: CC1(c2cccc(N)c2)Cn2nc(C(F)(F)F)cc2C(N)=N1]

Iron (272 mg, 4.87 mmol) was added to a mixture of intermediate 29 (340 mg, 1 mmol) and NH$_4$Cl (100 mg) in MeOH (20.4 mL) and H$_2$O (6.8 mL). The reaction was stirred at 80° C. for 5 hours. The crude was cooled and filtered over celite and the solvent was evaporated in vacuo. The residue was purified by flash column chromatography (silica gel; 7 M solution of NH$_3$ in MeOH/DCM). The desired fractions were collected and the solvents evaporated in vacuo to afford intermediate 28 as a transparent oil (260 mg, 84% yield). LCMS: 310 [M+H]$^+$; R$_t$: 2.50 min (method 5).

Following intermediate A30 was prepared according to the synthetic procedures described in examples A1-A4:

Example A30

Preparation of Intermediate A30: rac-2-amino-2-(5-bromo-2-fluoro-phenyl)-propan-1-ol, Intermediate A31: (R)-2-amino-2-(5-bromo-2-fluoro-phenyl)-propan-1-ol and Intermediate A32 (S) (S)-2-amino-2-(5-bromo-2-fluoro-phenyl)-propan-1-ol

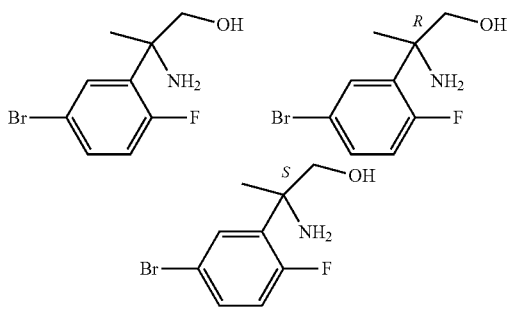

Prepared from 1-(5-bromo-2-fluoro-phenyl)-ethanone.

This racemic material was then further purified by preparative SFC on Chiralpak Diacel AD 20 μm (2000 g), mobile phase (70% heptane, 30% EtOH with 0.1% Et$_3$N). The desired fractions for each enantiomer were collected and concentrated in vacuo to yield intermediate A31 (44%) and intermediate A32 (44%).

The following intermediate was prepared according to the synthetic procedures described in example A7-A12:

Example A31

Preparation of Intermediate A33: (R)-[1-(5-bromo-2-fluoro-phenyl)-2-(4-fluoro-pyrazol-1-yl)-1-methyl-ethyl]-carbamic acid tert-butyl ester

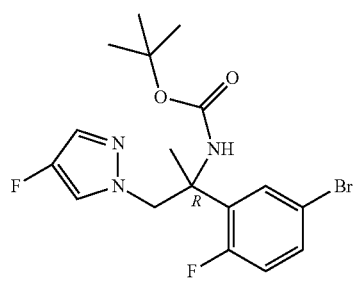

Prepared from intermediate A31. Flash column chromatography (silica gel; AcOEt/heptane) to yield intermediate A33 as a transparent oil (55%). LCMS: 418 [M+H]$^+$; R$_t$: 1.57 min (method 2).

The following intermediate was prepared according to the synthetic procedure described in example A25:

Example A32

Preparation of Intermediate A34: (R)-2-[2-(5-bromo-2-fluoro-phenyl)-2-tertbutoxycarbonylamino-propyl]-4-fluoro-2H-pyrazole-3-carboxylic acid ethyl ester

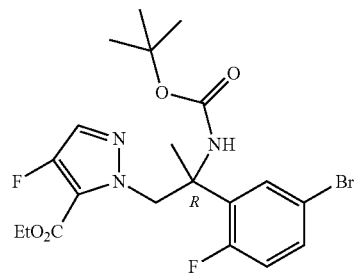

Prepared from intermediate A33. Flash column chromatography (silica gel; AcOEt//heptane) to yield intermediate A34 as a transparent oil (67%). LCMS: 490 [M+H]$^+$; R$_t$: 1.71 min (method 2).

The following intermediate was prepared according to the synthetic procedure described in example A16-Method B:

Example A33

Preparation of Intermediate A35: (R)-6-(5-bromo-2-fluoro-phenyl)-3-fluoro-6-methyl-6,7-dihydro-5H-pyrazolo[1,5-a]pyrazin-4-one

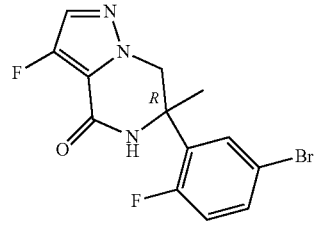

Prepared from intermediate A34. Flash column chromatography (silica gel; MeOH/DCM) to yield intermediate A35 as an oil (90%). LCMS: 343 [M+H]$^+$; R$_t$: 0.96 min (method 2).

The following intermediate was prepared according to the synthetic procedure described in example A18:

Example A34

Preparation of Intermediate A36: (R)-6-(5-bromo-2-fluoro-phenyl)-3-fluoro-6-methyl-6,7-dihydro-5H-pyrazolo[1,5-a]pyrazine-4-thione

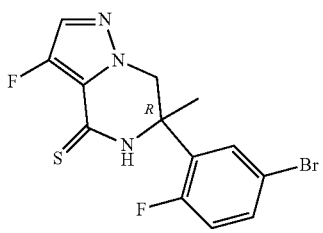

Prepared from intermediate A35. Flash column chromatography (silica gel; MeOH/DCM) to yield intermediate A36 as a yellow solid (85%). LCMS: 360 [M+H]⁺; $R_t$: 1.19 min (method 2).

Example A35

Preparation of Intermediate A37: (R)-6-(5-bromo-2-fluoro-phenyl)-3-fluoro-6-methyl-6,7-dihydro-pyrazolo[1,5-a]pyrazin-4-ylamine

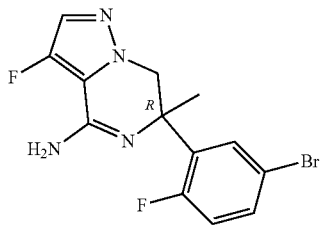

32% Aq. NH₃ solution (1.5 mL) and a 7 M solution of NH₃ in MeOH (3 mL) were added to intermediate A36 (330 mg, 0.921 mmol) at room temperature. The mixture was stirred at 100° C. in a sealed tube for 6 hours, then, after cooling, the solvent was removed in vacuo. The crude material was purified by column chromatography (silica gel; MeOH/DCM). The desired fractions were collected to afford intermediate A37 as a transparent oil (260 mg, 83%). LCMS: 343 [M+H]⁺; $R_t$: 1.03 min (method 2).

Example A36

Preparation of Intermediate A38: (R)-6-[5-(benzhydrylidene-amino)-2-fluoro-phenyl]-3-fluoro-6-methyl-6,7-dihydro-pyrazolo[1,5-a]pyrazin-4-ylamine

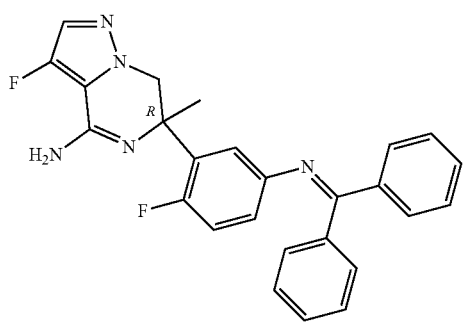

Toluene (58 mL) was added to a mixture of intermediate A37 (3 g, 8.178 mmol), tris(dibenzylideneacetone)dipalladium (749 mg, 0.818 mmol), 2,2'-bis(diphenylphosphino)-1,1'-binaphtyl (1.528 g, 2.453 mmol) and sodium tert-butoxide (1.415 g, 14.72 mmol) in a sealed tube under N₂ at room temperature. The mixture was flushed with N₂ for a few min and then benzophenoneimine (2.745 mL, 16.356 mmol) was added and the mixture was stirred at 90° C. for 18 hours. The mixture was concentrated in vacuo and then the mixture was diluted with H₂O and extracted with DCM. The organic layer was separated, dried (MgSO4), filtered and the solvent concentrated in vacuo. The crude product was purified by flash column chromatography (silica gel; MeOH/DCM). The desired fractions were collected and concentrated in vacuo to yield intermediate A38 as a pale yellow solid (3 g, 83%). LCMS: 442 [M+H]⁺; $R_t$: 1.39 min (method 2).

Example A37

Preparation of Intermediate A39: (R)-6-(5-amino-2-fluoro-phenyl)-3-fluoro-6-methyl-6,7-dihydro-pyrazolo[1,5-a]pyrazin-4-ylamine

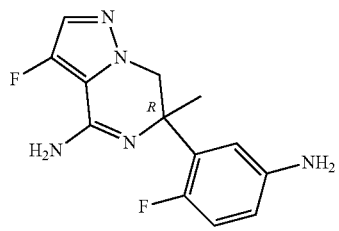

HCl 37% (1.05 mL) was added to a solution of intermediate A38 (3 g, 6.795 mmol) in iPrOH (78 mL). The mixture was stirred at room temperature for 2 hours. The mixture was concentrated, and then triturated with Et₂O. The solid was filtered off and taken on iPrOH. NaHCO₃ (5.709 g) was added to it and the mixture stirred for 1 hour, then filtered and the filtrate was concentrated in vacuo. The product was purified by flash column chromatography (silica gel; MeOH/DCM). The desired fractions were collected and concentrated in vacuo to yield pale a yellow oil. The material was treated with a mixture of DIPE/Et₂O 3:1 to afford intermediate A39 as a yellow solid (1.1 g, 58%). LCMS: 278 [M+H]⁺; $R_t$: 0.56 min (method 2).

Example A38

Preparation of Intermediate A40: (3-acetyl-4-fluoro-phenyl)-carbamic acid benzyl ester

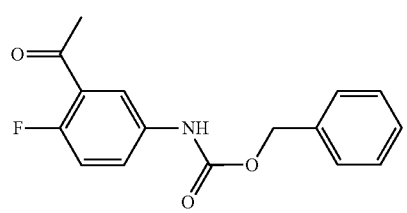 [SMILES: CC(=O)c1cc(NC(=O)OCc2ccccc2)ccc1F]

Benzyl chloroformate (3 mL, 21.5 mmol) was added to a mixture of 1-(5-amino-2-fluorophenyl)ethanone (3 g, 19.6 mmol) and tetrabutylammonium bromide at room temperature. The reaction was stirred at room temperature for 24 hours, the crude was treated with AcOEt (50 mL) and H₂O (50 mL), the organic phase was separated and evaporated in vacuo. The crude was purified by column chromatography (silica gel; MeOH/DCM). The desired fractions were collected and the solvents evaporated in vacuo to afford intermediate A40 as a cream solid (4.7 g, 84%). LCMS: 286 [M−H]⁻; $R_t$: 2.81 min (method 3).

The following intermediate was prepared according to the synthetic procedure described for the synthesis of intermediate A11:

Example A39

Preparation of Intermediate A41: rac-{3-[2-(4-bromo-pyrazol-1-yl)-1-tert-butoxycarbonylamino-1-methyl-ethyl]-4-fluoro-phenyl}-carbamic acid ethyl ester

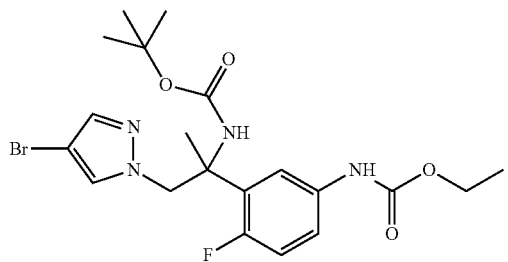 [SMILES: CCOC(=O)Nc1ccc(F)c(C(C)(Cn2cc(Br)cn2)NC(=O)OC(C)(C)C)c1]

Prepared from intermediate A40. Flash column chromatography (silica gel; AcOEt/heptane) followed by washing with DIPE to yield intermediate A41 as a white solid (72%). LCMS: 487 [M+H]$^+$; R$_t$: 3.56 min (method 3).

Example A40

Preparation of Intermediate A42: rac-ethyl 2-[2-[5-[bis(ethoxycarbonyl)amino]-2-fluoro-phenyl]-2-(tert-butoxycarbonylamino propyl]-4-bromo-pyrazole-3-carboxylate

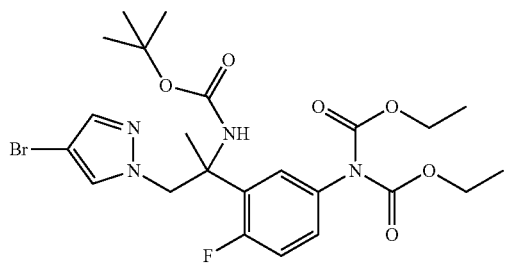 [SMILES: CCOC(=O)N(C(=O)OCC)c1ccc(F)c(C(C)(Cn2cc(Br)cn2)NC(=O)OC(C)(C)C)c1]

Lithium diisopropylamide (2 M in cyclohexane/ethylbenzene/THF, 7.36 mL, 14.721 mmol) was added to a stirred solution of intermediate A41 (2.1 g, 4.327 mmol) in dry THF (66 mL) at −70° C. under N$_2$ atmosphere. The mixture was stirred at −70° C. for 1 hour, then ethyl chloroformate (0.91 mL, 9.519 mmol) was added at −70° C. and the reaction was warmed at −30° C. for 2 hours. The crude was quenched with a saturated solution of NH$_4$Cl (30 mL) at −50° C. and warmed to room temperature, the crude was extracted with AcOEt (3×20 mL), the organic phase was evaporated in vacuo, dried, the resulting crude was purified by flash column chromatography (silica gel; AcOEt/heptane). The desired fractions were collected and evaporated in vacuo to yield intermediate A42 (1.6 g, 59%). LCMS: 631 [M+H]$^+$; R$_t$: 4.22 min (method 3).

The following intermediate was prepared according to the synthetic procedure described in example A16-Method B:

Example A41

Preparation of Intermediate A43: rac-ethyl N-[3-(3-bromo-6-methyl-4-oxo-5,7-dihydropyrazolo[1,5-a]pyrazin-6-yl)-4-fluoro-phenyl]-N-ethoxycarbonyl-carbamate and Intermediate A44: rac-ethyl N-[3-(3-bromo-6-methyl-4-oxo-5,7-dihydropyrazolo[1,5-a]pyrazin-6-yl)-4-fluoro-phenyl]carbamate

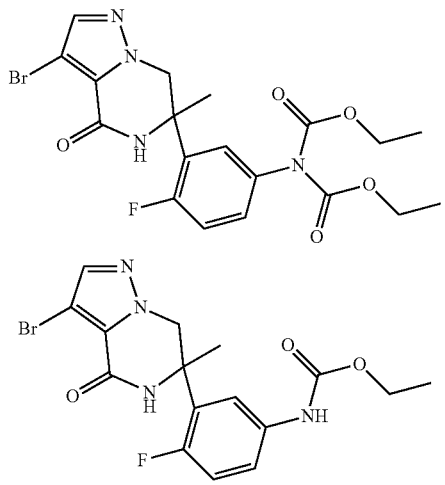

Prepared from intermediate A42. Flash column chromatography (silica gel; AcOEt/heptane) to yield intermediate A43 as a white solid (52%) and intermediate A44 as a cream solid (20%). LCMS: A43: 485 [M+H]$^+$; R$_t$: 2.15 min (method 3); A44: 413 [M+H]$^+$; R$_t$: 0.98 min (method 2)

The following intermediate was prepared according to the synthetic procedure described in examples A18:

Example A42

Preparation of Intermediate A45: rac-ethyl N-[3-(3-bromo-6-methyl-4-thioxo-5,7-dihydropyrazolo[1,5-a]pyrazin-6-yl)-4-fluoro-phenyl]-N-ethoxycarbonyl-carbamate and Intermediate A46: rac-ethyl N-[3-(3-bromo-6-methyl-4-thioxo-5,7-dihydropyrazolo[1,5-a]pyrazin-6-yl)-4-fluoro-phenyl]carbamate

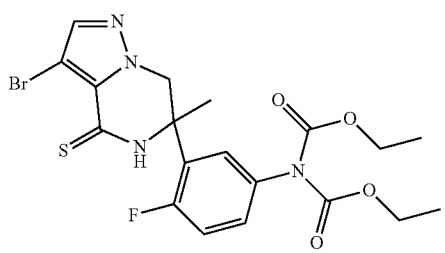

-continued

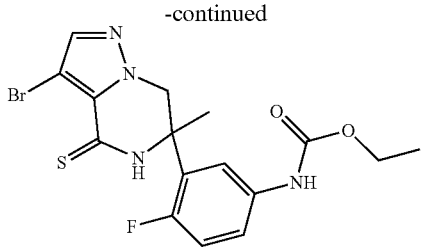

Prepared from intermediate A43 and A44. Flash column chromatography (silica gel; MeOH/DCM) to yield intermediate A45 as a yellow solid (65%) and intermediate A46 as a yellow solid (28%). LCMS: A45: 501 [M+H]$^+$; R$_t$: 2.70 min (method 3); A46: 429 [M+H]$^+$; R$_t$: 2.53 min (method 3) The following intermediate was prepared according to the synthetic procedure described in example A35:

Example A43

Preparation of Intermediate A47: rac-[3-(4-amino-3-bromo-6-methyl-6,7-dihydro-pyrazolo[1,5-a]pyrazin-6-yl)-4-fluoro-phenyl]-carbamic acid ethyl ester

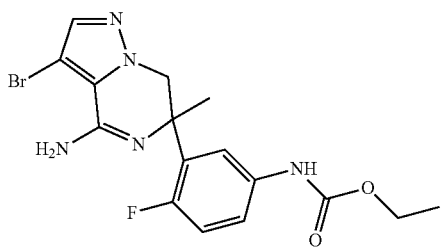 [SMILES: CCOC(=O)Nc1ccc(F)c(C2(C)Cn3ncc(Br)c3C(N)=N2)c1]

Prepared from intermediates A45 and A46. Flash column chromatography (silica gel; MeOH/DCM) to yield intermediate A47 as a cream solid which was used as such in the next step. The following intermediate was prepared according to the synthetic procedure described in example A22-Method B:

Example A44

Preparation of Intermediate A48: rac-[3-(4-amino-6-methyl-6,7-dihydro-pyrazolo[1,5-a]pyrazin-6-yl)-4-fluoro-phenyl]-carbamic acid ethyl ester

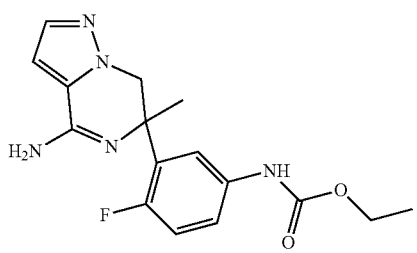 [SMILES: CCOC(=O)Nc1ccc(F)c(C2(C)Cn3nccc3C(N)=N2)c1]

Prepared from intermediate A47. Flash column chromatography (silica gel; 7 M solution of NH$_3$ in MeOH/DCM) to yield intermediate A48 as an oil (71%). LCMS: 322 [M+H]$^+$; R$_t$: 0.63 min (method 2).

Example A45

Preparation of Intermediate A49: 6-(5-amino-2-fluoro-phenyl)-6-methyl-6,7-dihydro-pyrazolo[1,5-a]pyrazin-4-ylamine

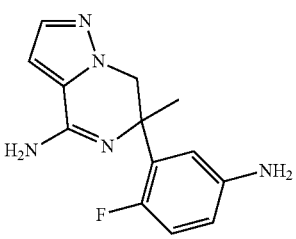 [SMILES: CC1(c2cc(N)ccc2F)Cn2nccc2C(N)=N1]

Intermediate A48 (300 mg, 0.905 mmol) was added to a solution of HCl (6 M in H$_2$O, 17.1 mL) at room temperature. The mixture was stirred at 110° C. for 35 hours, then the solvent was removed in vacuo and treated with a saturated solution of NaHCO$_3$ and extracted with AcOEt (3×10 mL). The organic layer was separated and evaporated in vacuo. The crude material was purified by column chromatography (silica gel; MeOH/DCM). The desired fractions were collected to intermediate A49 as a transparent oil (160 mg, 68%). LCMS: 260 [M+H]$^+$; R$_t$: 0.51 min (method 3).

The following intermediate was prepared according to the synthetic procedure described in example A8:

Example A46

Preparation of Intermediate A50: rac-4-(5-bromo-2-fluoro-phenyl)-4-difluoromethyl-2-oxo-2lambda*4*-[1,2,3]oxathiazolidine-3-carboxylic acid tert-butyl ester

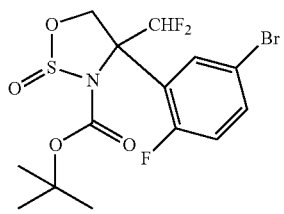 [SMILES: CC(C)(C)OC(=O)N1S(=O)OCC1(c1cc(Br)ccc1F)C(F)F]

Prepared from carbamic acid, N-[1-(5-bromo-2-fluorophenyl)-2,2-difluoro-1-(hydroxymethyl)ethyl]-, 1,1-dimethylethyl ester. Intermediate A50 obtained as a yellow oil (crude material, mixture of diastereoisomers, 100%).

The following intermediate was prepared according to the synthetic procedure described in example A9:

Example A47

Preparation of Intermediate A51: rac-4-(5-bromo-2-fluoro-phenyl)-4-difluoromethyl-2,2-dioxo-2lambda*6*-[1,2,3]oxathiazolidine-3-carboxylic acid tert-butyl ester

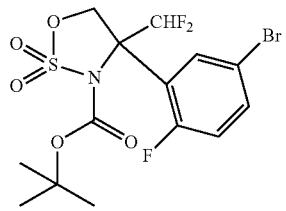 [SMILES: CC(C)(C)OC(=O)N1C(c2cc(Br)ccc2F)(C(F)F)COS1(=O)=O]

Prepared from intermediate A50. Trituration in heptane followed by column chromatography (silica gel; DCM) to yield intermediate A51 as a white solid (78%). LCMS: 465 [M+NH$_4$]$^+$; R$_t$: 1.46 min (method 2).

Example A48

Preparation of Intermediate A52: rac-1-(5-bromo-2-fluoro-phenyl)-2,2-difluoro-1-(5-methyl-3-nitro-pyrazol-1-ylmethyl)-ethylamine

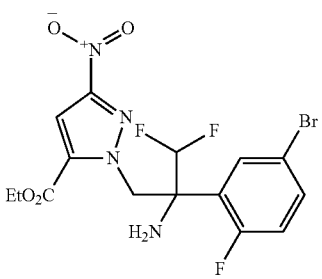

To intermediate A51 (6.8 g, 15.238 mmol) and ethyl 5-nitro-1H-pyrazole-3-carboxylate (3.4 g, 18.365 mmol) in MeCN (150 mL) was added DBU (5.1 mL, 34.103 mmol) at room temperature. The resulting mixture was stirred at 60° C. for 18 hours. The solvent was then evaporated in vacuo and to the residue was added HCl (4 M in dioxane, 40 mL) at room temperature. The resulting solution was stirred at room temperature for 2 hours, then the solvent was evaporated in vacuo. H$_2$O and sat. Na$_2$CO$_3$ were added to the residue, and the mixture extracted with DCM. The organic layer was dried (Na$_2$SO$_4$), filtered and the solvents evaporated in vacuo. The crude product was purified by flash column chromatography (silica gel; DCM in heptane 50/50). The desired fractions were collected and evaporated in vacuo to yield intermediate 52 as a sticky foam (4.6 g, 67%). LCMS: 453 [M+H]$^+$; R$_t$: 1.46 min (method 2).

Example A49

Preparation of Intermediate A53: rac-6-(5-bromo-2-fluoro-phenyl)-6-difluoromethyl-2-nitro-6,7-dihydro-5H-pyrazolo[1,5-a]pyrazin-4-one

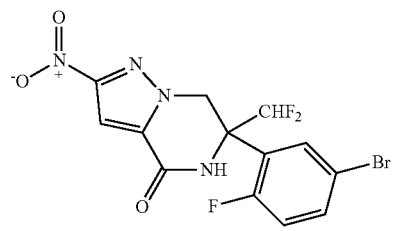

DBU (4.126 mL, 27.6 mmol) was added to a stirred mixture of intermediate A52 (4.15 g, 9.198 mmol) in MeCN (45 mL) in a sealed tube. The mixture was stirred at 150° C. for 30 min under microwave irradiation. The mixture was diluted with 10% NH$_4$Cl and extracted with DCM. The organic layer was dried (Na$_2$SO$_4$), filtered and the solvent evaporated in vacuo. The residue was purified by flash column chromatography (silica gel; AcOEt). The desired fractions were collected and evaporated in vacuo to yield intermediate A54 (2.48 g, 67%). LCMS: 405 [M−H]$^−$; R$_t$: 1.10 min (method 2).

Example A50

Preparation of Intermediate A54: rac-2-amino-6-(5-bromo-2-fluoro-phenyl)-6-difluoromethyl-6,7-dihydro-5H-pyrazolo[1,5-a]pyrazin-4-one

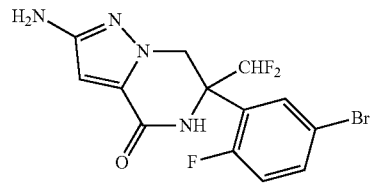 [SMILES: Nc1cc2n(n1)CC(c1cc(Br)ccc1F)(C(F)F)NC2=O]

Intermediate A53 (2.4 g, 5.924 mmol) was dissolved in MeOH (150 mL). The solution was hydrogenated with RuO$_2$ cartridge (50° C., full hydrogen, 1 ml/min). The solvent was evaporated in vacuo and the residue purified by flash column chromatography (silica gel; MeOH/DCM). The desired fractions were collected and concentrated in vacuo to yield intermediate A54 as an off-white solid (2.1 g, 94%). LCMS: 377 [M+H]$^+$; R$_t$: 0.74 min (method 2).

Example A51

Preparation of Intermediate A55: rac-6-(5-bromo-2-fluoro-phenyl)-6-difluoromethyl-6,7-dihydro-5H-pyrazolo[1,5-a]pyrazin-4-one

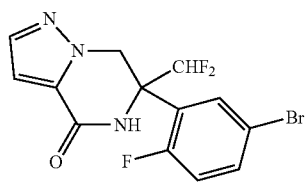 [SMILES: O=C1NC(c2cc(Br)ccc2F)(C(F)F)Cn2nccc21]

A mixture of intermediate A54 (1.8 g, 4.798 mmol), EtOH (36 mL) and H$_2$SO$_4$ (0.767 mL) was heated to 90° C. Sodium nitrite (828 mg, 11.995 mmol) was then added portionwise and the mixture was stirred at 90° C. for 20 min. Then, the mixture was cooled to room temperature, poured into sat. Na$_2$CO$_3$ and H$_2$O and extracted with DCM. The organic layer was separated, dried (Na$_2$SO$_4$), filtered and the solvents evaporated in vacuo. The crude product was purified by flash column chromatography (silica gel; MeOH/DCM). The desired fractions were collected and concentrated in vacuo to yield intermediate A55 as a white solid (1.25 g, 72%). LCMS: 403 [M+MeCN+H]$^+$; R$_t$: 0.92 min (method 2).

The following intermediate was prepared according to the synthetic procedure described in examples A18:

Example A52

Preparation of Intermediate A56: rac-6-(5-bromo-2-fluoro-phenyl)-6-difluoromethyl-6,7-dihydro-5H-pyrazolo[1,5-a]pyrazine-4-thione

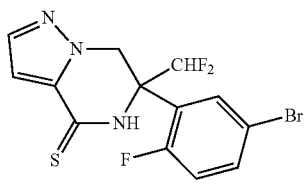 [SMILES: Fc1ccc(Br)cc1C1(C(F)F)Cn2nccc2C(=S)N1]

Prepared from intermediate A55. Flash column chromatography (silica gel; DCM) to yield intermediate 56 as a yellow solid (1.14 g, 88%). LCMS: 419 [M+MeCN+H]$^+$; R$_t$: 1.19 min (method 2).

Example A53

Preparation of Intermediate A57: rac-6-(5-bromo-2-fluoro-phenyl)-6-difluoromethyl-6,7-dihydro-pyrazolo[1,5-a]pyrazin-4-ylamine

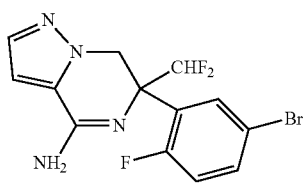 [SMILES: NC1=NC(c2cc(Br)ccc2F)(C(F)F)Cn2nccc21]

A solution of intermediate 56 (1.12 g, 2.977 mmol) in 7 M NH$_3$ in MeOH (30 mL) was stirred under microwave irradiation for 30 min at 120° C. The solvent was evaporated in vacuo and the residue treated with DCM and washed with diluted Na$_2$CO$_3$ solution. The organic layer was separated, dried (Na$_2$SO$_4$), filtered and the solvents evaporated in vacuo. The crude product was purified by flash column chromatography (silica gel; 7 M solution of NH$_3$ in MeOH/DCM). The desired fractions were collected and concentrated in vacuo to yield intermediate 57 as a yellow solid (1.03 g, 96%). LCMS: 361 [M+H]$^+$; R$_t$: 0.99 min (method 2).

The following intermediate was prepared according to the synthetic procedures described in examples A36-A37:

Example A54

Preparation of Intermediate A58: rac-6-(5-amino-2-fluoro-phenyl)-6-difluoromethyl-6,7-dihydro-pyrazolo[1,5-a]pyrazin-4-ylamine

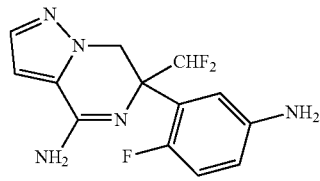 [SMILES: NC1=NC(c2cc(N)ccc2F)(C(F)F)Cn2nccc21]

Prepared from intermediate A54. Flash column chromatography (silica gel; 7 M NH$_3$ in MeOH/DCM) to yield intermediate 58 as an off-white foam (86%). LCMS: 296 [M+H]$^+$; R$_t$: 0.61 min (method 2).

Example A55

Preparation of Intermediate A59: 1H-pyrazole-3,5-dicarboxylic acid diamide

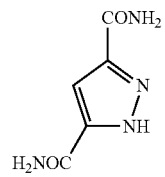

Diethylpyrazole-3,5-dicarboxylate (5.2 g, 24.5 mmol) was dissolved in a 7 M NH$_3$ in MeOH and the mixture was heated at 70° C. in a sealed tube for 48 hours. The solvent was then evaporated to give intermediate A59 (3.74 g, 99%) as a solid.

Example A56

Preparation of Intermediate A60: 1H-pyrazole-3,5-dicarbonitrile

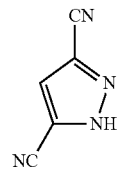

Phosphorus oxychloride (11.249 mL, 120.679 mmol) was added to a mixture of intermediate 59 (3.72 g, 24.136 mmol) in MeCN (90 mL) at 0° C. The mixture was stirred in a sealed tube at 120° C. for 5 hours (until the solid disappeared). The reaction was poured in a mixture of ice/H$_2$O and extracted with DCM. The organic layer was separated, dried (Na$_2$SO$_4$), filtered and the solvents evaporated in vacuo to give intermediate A60 as a solid, which was used in next step without further purification. LCMS: 117 [M–H]$^-$; R$_t$: 0.61 min (method 2).

Example A57

Preparation of Intermediate A61: (R)-[1-(5-bromo-2-fluoro-phenyl)-2-(3,5-dicyano-pyrazol-1-yl)-1-methyl-ethyl]-carbamic acid tert-butyl ester

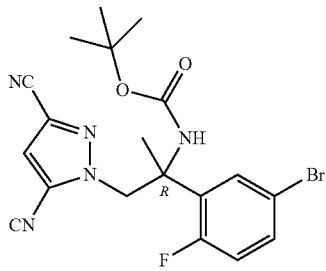

Prepared from intermediate A31. Flash column chromatography (silica gel; AcOEt/DCM) to yield intermediate A61 as a foam (60%). LCMS: 467 [M+NH$_4$]$^+$; R$_t$: 1.57 min (method 2).

Example A58

Preparation of Intermediate A62: (R)-4-amino-6-(5-bromo-2-fluorophenyl)-6-methyl-6,7-dihydro-pyrazolo[1,5-a]pyrazine-2-carbonitrile

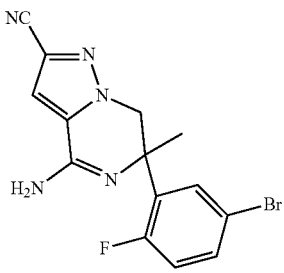 [SMILES: CC1(c2cc(Br)ccc2F)Cn2nc(C#N)cc2C(N)=N1]

To a stirred mixture of intermediate A61 (4.483 g, 8.4 mmol) in DCM (40 mL) at room temperature was added trifluoroacetic acid (4 mL). The mixture was stirred for 20 hours at room temperature, then basified with a sat. solution of Na$_2$CO$_3$ and extracted with DCM. The organic layer was separated, dried (MgSO$_4$), filtered and concentrated in vacuo. The residue was purified by flash column chromatography (silica gel; 7 N NH$_3$ in MeOH/DCM). The desired fractions were collected and concentrated in vacuo to give intermediate A62 (2.9 g, 99%). LCMS: 349 [M+H]$^+$; R$_t$: 1.13 min (method 2).

Example A59

Preparation of Intermediate A63: (R)-4-amino-6-(5-amino-2-fluorophenyl)-6-methyl-6,7-dihydro-pyrazolo[1,5-a]pyrazine-2-carbonitrile

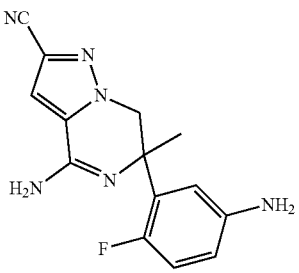 [SMILES: CC1(c2cc(N)ccc2F)Cn2nc(C#N)cc2C(N)=N1]

The reaction was set-up in two equal batches. The total amount of material used is reported. CuI (342 mg, 1.795 mmol) was added to a suspension of intermediate A62 (500 mg, 1.436 mmol), sodium azide (284 mg, 4.308 mmol), N,N'-dimethylethylenediamine (255 µL, 2.369 mmol) and Na$_2$CO$_3$ (457 mg, 4.308 mmol) in MeCN (10 mL) and the reaction was degassed. The mixture was heated at 110° C. for 4 hours, then at 120° C. for additional 2 hours. The mixture was then quenched with 1 M HCl and the water layer was basified with NH$_4$OH and extracted with AcOEt (3×). The combined organic layers were dried (MgSO$_4$), filtered and concentrated. The crude product was purified by flash column chromatography (silica gel; 7 N solution of NH$_3$ in MeOH/DCM). The desired fractions were collected and concentrated in vacuo to yield intermediate A63 (300 mg, 65%). LCMS: 285 [M+H]$^+$; R$_t$: 0.74 min (method 2).

The following intermediate was prepared according to the synthetic procedures described in examples A7-A9, A11, A13 and A15:

Example A60

Preparation of Intermediate A64: (R)-6-(5-bromo-2-fluoro-phenyl)-6-methyl-4-oxo-4,5,6,7-tetrahydro-pyrazolo[1,5-a]pyrazine-2-carboxylic acid ethyl ester

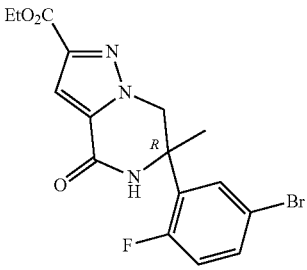

Prepared from diethylpyrazole-3,5-dicarboxylate. Intermediate A64 used as a crude white solid in the subsequent reaction.

Example A61

Preparation of Intermediate A65: (R)-6-(5-bromo-2-fluoro-phenyl)-2-hydroxymethyl-6-methyl-6,7-dihydro-5H-pyrazolo[1,5-a]pyrazin-4-one

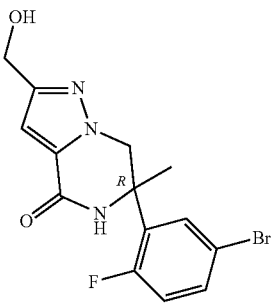

Sodium borohydride (3.094 g, 81.774 mmol) was added to a stirred solution of intermediate 64 (3.6 g, 9.086 mmol) in THF (10 mL) and MeOH (5 mL) at 0° C. The mixture was stirred at room temperature for 18 hours. The mixture was cooled to 0° C., treated with H$_2$O and extracted with DCM. The organic layer was dried (Na$_2$SO$_4$), filtered and the solvent evaporated in vacuo to yield intermediate A65 (3.2 g, 99%) as a white solid.

Example A62

Preparation of Intermediate A66: (R)-6-(5-bromo-2-fluoro-phenyl)-6-methyl-4-oxo-4,5,6,7-tetrahydro-pyrazolo[1,5-a]pyrazine-2-carbaldehyde

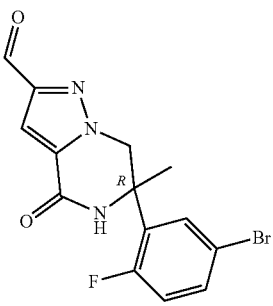

Manganese dioxide (7 g, 80.5 mmol) was added to a solution of intermediate A65 (3.2 g, 9.035 mmol) in chloroform (48 mL). The reaction mixture was stirred at 62° C. for 4 hours. The mixture was filtered through celite and washed with DCM. The organic layer was concentrated to yield intermediate A66 as a light orange fluffy solid (2.3 g, 72%).

Example A63

Preparation of Intermediate A67: (R)-6-(5-bromo-2-fluoro-phenyl)-2-difluoromethyl-6-methyl-6,7-dihydro-5H-pyrazolo[1,5-a]pyrazin-4-one

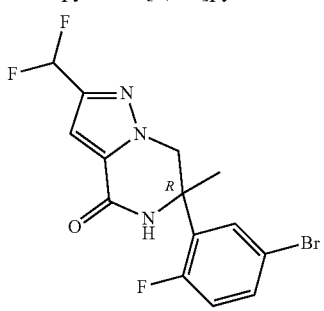

A solution of intermediate A66 (2.3 g, 6.531 mmol) in DCM (50 ml) and DAST (2.193 mL, 16.328 mmol) in DCM (50 ml) were pumped through a flow chemistry Vapourtec R2+R4 modular device, coil 10 mL at 80° C., R$_t$=15 min. The outlet solution was collected over CaCO$_3$. The solution was filtered through celite and washed with DCM, the organic layer was washed with a sat. solution of NaHCO$_3$ and extracted with DCM. The organic layer was dried over Na$_2$SO$_4$, filtered and concentrated in vacuo to yield intermediate A67 (2.2 g, 90%) as a brown oil.

Example A64

Preparation of Intermediate A68: (R)-6-(5-bromo-2-fluoro-phenyl)-2-difluoromethyl-6-methyl-6,7-dihydro-5H-pyrazolo[1,5-a]pyrazine-4-thione

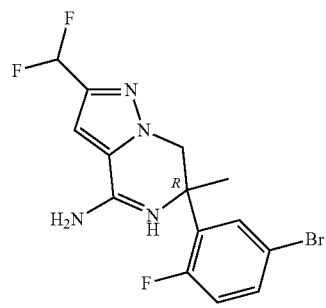

Phosphoruspentasulfide (1.871 g, 8.419 mmol) was added to a solution of intermediate A67 (2.1 g, 5.613 mmol) in dioxane (1 mL) and the mixture was heated at 100° C. for 18 hours. The mixture was concentrated in vacuo and purified by flash column chromatography (silica gel; DCM). The desired fractions were collected and concentrated in vacuo to yield intermediate A68 (2 g, 91%) as a yellow oil. LCMS: 392 [M+H]$^+$; R$_t$: 1.29 min (method 2).

Example A65

Preparation of Intermediate A69: (R)-6-(5-bromo-2-fluoro-phenyl)-2-difluoromethyl-6-methyl-6,7-dihydro-pyrazolo[1,5-a]pyrazin-4-ylamine

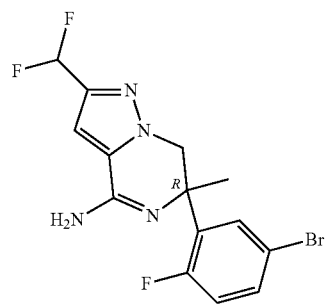

The reaction was set-up in two equal batches. The total amount of material used is reported. NH₃ (2 M in EtOH, 30 mL, 60 mmol) was added to intermediate A69 (2 g, 5.125 mmol) and NH₄Cl (2.173 g, 41 mmol). The mixture was heated under microwave irradiation at 170° C. for 45 min. The mixture was concentrated, and another 30 mL of NH₃ (2 M in EtOH) were added. The mixture was heated under microwave irradiation at 170° C. for 45 min. This procedure was repeated 4 times for a total amount of time of 180 min. The mixture was filtered and the filtrate was concentrated in vacuo. The crude was purified by flash column chromatography (silica gel; MeOH/DCM). The desired fractions were collected and concentrated in vacuo to yield intermediate A69 (1 g, 52%) as an oil. LCMS: 375 [M+H]⁺; $R_t$: 1.11 min (method 2).

The following intermediate was prepared according to a synthetic procedures similar to the one described in example A59:

Example A66

Preparation of Intermediate A70: (R)-6-(5-amino-2-fluoro-phenyl)-2-difluoromethyl-6-methyl-6,7-dihydro-pyrazolo[1,5-a]pyrazin-4-ylamine

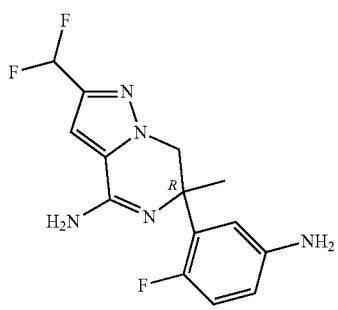

Prepared from intermediate A69. Flash column chromatography (silica gel; MeOH/DCM) to yield intermediate A70 as an oil (51%). LCMS: 310 [M+H]⁺; $R_t$: 0.69 min (method 2).

The following intermediate was prepared according to a synthetic procedures similar to the one described in examples A7-A11, A48, A15 and A18:

Example A67

Preparation of Intermediate A71: (R)-6-(5-bromo-2-fluoro-phenyl)-3-fluoro-2,6-dimethyl-6,7-dihydro-5H-pyrazolo[1,5-a]pyrazine-4-thione

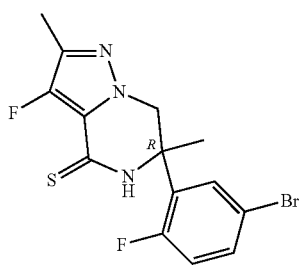

Prepared from 4-fluoro-5-methyl-1H-pyrazole-3-carboxylic acid ethyl ester. Flash column chromatography (silica gel; AcOEt/DCM) to yield intermediate A71 as a yellow solid (92%). LCMS: 374 [M+H]⁺; $R_t$: 1.27 min (method 2).

Example A68

Preparation of Intermediate A72: (R)-6-(5-bromo-2-fluoro-phenyl)-3-fluoro-2,6-dimethyl-6,7-dihydro-pyrazolo[1,5-a]pyrazin-4-ylamine

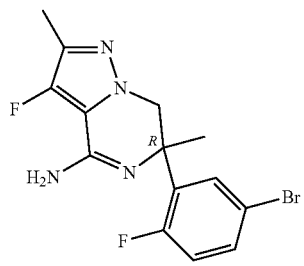

NH₃ (2 M in EtOH, 10 eq) was added to a solution of intermediate 71 (2.4 g, 6.448 mmol) and NH₄Cl (4 eq.) and the mixture was heated at 85° C. in a sealed tube for 24 hours. The solvent was evaporated in vacuo and the residue suspended in DCM and washed with H₂O. The organic layer was separated, dried (MgSO₄), filtered and the solvents evaporated in vacuo. To the residue more NH₄Cl (4 eq.) followed by NH₃ (2 M in EtOH, 10 eq), were added and the mixture was heated at 85° C. in a sealed tube for 24 hours. This process was repeated four more times for a total amount of NH₃ (2 M in EtOH) of 276 mL, and 8.277 g of NH₄Cl. The product was then purified by flash column chromatography (silica gel; MeOH/DCM). The desired fractions were collected and concentrated in vacuo to yield intermediate A72 (960 mg, 42%) as a pale yellow solid. LCMS: 357 [M+H]⁺; $R_t$: 1.11 min (method 2).

The following intermediate was prepared according to a synthetic procedures similar to the one described in examples A36-A37:

Example A69

Preparation of Intermediate A73: (R)-6-(5-amino-2-fluoro-phenyl)-3-fluoro-2,6-dimethyl-6,7-dihydro-pyrazolo[1,5-a]pyrazin-4-ylamine

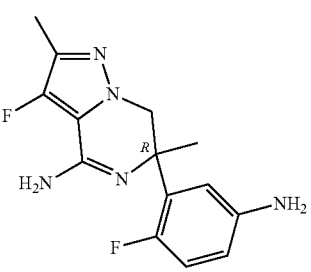

Prepared from intermediate A72. Flash column chromatography (silica gel; 7 N NH₃ in MeOH/DCM) to yield intermediate A73 as a pale yellow solid (42%).

The following intermediate was prepared according to a synthetic procedures similar to the one described in examples A7-A9, A48, A23, A16B, A18, A21, A36, A37:

Example A70

Preparation of Intermediate A74: (R)-6-(5-amino-2-fluoro-phenyl)-3-chloro-6-methyl-6,7-dihydro-pyrazolo[5-a]pyrazin-4-ylamine

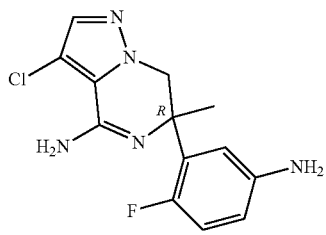

Prepared from intermediate A31. Flash column chromatography (silica gel; MeOH/DCM) followed by trituration in DIPE/Et$_2$O to yield intermediate A74 as a yellow solid (94%). LCMS: 294 [M+H]$^+$; R$_t$: 1.13 min (method 3).

Preparation of the Final Compounds

Example B1

Preparation of Compound 1: (R)-6-[3-(5-chloro-pyridin-3-yl)-phenyl]-6-methyl-6,7-dihydro-pyrazolo[1,5-a]pyrazin-4-ylamine trifluoroacetate salt

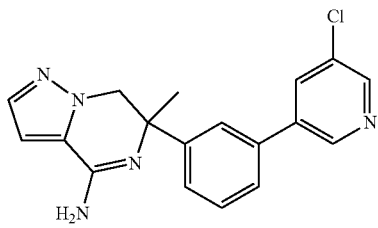 [SMILES: CC1(c2cccc(-c3cncc(Cl)c3)c2)Cn2nccc2C(N)=N1]

A 32% aq. NH$_3$ solution (0.5 mL) was added to a stirred mixture of intermediate A18 (60 mg, 0.17 mmol) in a 7 M solution of NH$_3$ in MeOH (1.5 mL) in a sealed tube. The mixture was stirred at 100° C. for 5 hours. After cooling to room temperature, the solvents were evaporated in vacuo. The crude product was purified by short column chromatography (silica gel; MeOH/DCM). The desired fractions were collected and concentrated in vacuo to give a fraction that was further purified by reverse phase HPLC (Gradient from 80% 0.1% TFA solution in H$_2$O, 20% CH$_3$CN to 0% 0.1% TFA solution in H$_2$O, 100% CH$_3$CN). and triturated with DIPE to yield compound 1 (36 mg, 46% yield) as a white solid. $^1$H NMR (500 MHz, DMSO-d$_6$) δ ppm 1.79 (s, 3H), 4.69 (d, J=13.6 Hz, 1H), 5.25 (d, J=13.9 Hz, 1H), 7.23 (d, J=2.3 Hz, 1H), 7.45 (br. d, J=8.7 Hz, 1H), 7.52 (t, J=7.8 Hz, 1H), 7.69 (d, J=2.0 Hz, 1H), 7.75 (br. d, J=7.8 Hz, 1H), 7.94-7.96 (m, 1H), 8.28 (t, J=2.2 Hz, 1H), 8.66 (d, J=2.3 Hz, 1H), 8.88 (d, J=2.0 Hz, 1H), 9.28 (br. s, 1H), 9.87 (br. s, 1H), 11.06 (br. s, 1H).

Example B2

Preparation of Compound 2: rac-5-chloro-pyridine-2-carboxylic acid [3-(4-amino-6-methyl-6,7-dihydro-pyrazolo[1,5-a]pyrazin-6-yl)-phenyl]-amide

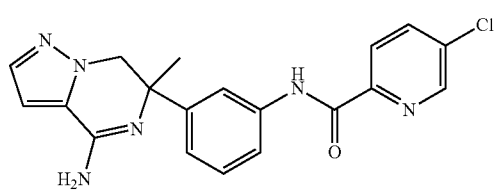 [SMILES: CC1(c2cccc(NC(=O)c3ccc(Cl)cn3)c2)Cn2nccc2C(N)=N1]

5-Chloro-pyridine-2-carboxylic acid (71.8 mg, 0.68 mmol) was added to a solution of 4-(4,6-dimethoxy-1,3,5-triazin-2-yl)-4-methylmorpholinium chloride (137 mg, 0.5 mmol) in MeOH (4 mL). The mixture was stirred at room temperature for 5 min. Then the mixture was cooled to 0° C. and a solution of intermediate A22 (100 mg, 0.41 mmol) in MeOH (3 mL) was added. The mixture was warmed to room temperature and stirred for 3 hours. The mixture was treated with a saturated solution of Na$_2$CO$_3$ and H$_2$O and extracted with DCM. The organic layer was separated, dried (Na$_2$SO$_4$), filtered and the solvents evaporated in vacuo. The crude product was triturated with Et$_2$O and then was purified by flash column chromatography (silica gel; MeOH/DCM). The desired fractions were collected and the solvents evaporated in vacuo and the resulting fraction was further purified by flash column chromatography (silica gel; MeOH/DCM). The desired fractions were collected and the solvents evaporated in vacuo to yield compound 2 (21 mg, 13% yield) as a white solid. $^1$H NMR (500 MHz, CDCl$_3$) δ ppm 1.67 (s, 3H), 4.38 (d, J=13.3 Hz, 1H), 4.53 (d, J=13.3 Hz, 1H), 4.79 (br. s, 2H), 6.72 (br. s, 1H), 7.24 (br. d, J=7.8 Hz, 1H), 7.34 (t, J=7.9 Hz, 1H), 7.51 (d, J=2.0 Hz, 1H), 7.73 (dd, J=8.1, 1.2 Hz, 1H), 7.85-7.90 (m, 2H), 8.23 (d, J=8.4 Hz, 1H), 8.55 (d, J=2.0 Hz, 1H), 9.86 (br. s, 1H).

Example B3

Preparation of Compound 3: rac-3,5-dichloro-pyridine-2-carboxylic acid [3-(4-amino-6-methyl-6,7-dihydro-pyrazolo[1,5-a]pyrazin-6-yl)-phenyl]-amide

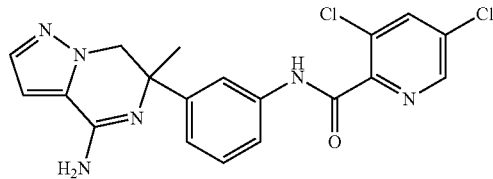 [SMILES: CC1(c2cccc(NC(=O)c3ncc(Cl)cc3Cl)c2)Cn2nccc2C(N)=N1]

3,5-Dichloro-pyridine-2-carboxylic acid (112 mg, 0.58 mmol) was added to a solution of 4-(4,6-dimethoxy-1,3,5-triazin-2-yl)-4-methylmorpholinium chloride (176.2 mg, 0.64 mmol) in MeOH (5 mL). The mixture was stirred at room temperature for 5 min. Then the mixture was cooled to 0° C. and a solution of intermediate A22 (128 mg, 0.53 mmol)

in MeOH (5 mL) was added. The mixture was warmed to room temperature and stirred for 3 hours. The mixture was treated with a saturated solution of Na$_2$CO$_3$ and H$_2$O and extracted with DCM. The organic layer was separated, dried (MgSO$_4$), filtered and the solvents evaporated in vacuo. The crude product was purified by flash column chromatography (silica gel; MeOH/DCM). The desired fractions were collected and the solvents evaporated in vacuo. The crude product was triturated with Et$_2$O and then was purified by flash column chromatography (silica gel; MeOH/DCM). The desired fractions were collected and the solvents evaporated in vacuo to yield compound 3 (180 mg, 82% yield) as a white solid. $^1$H NMR (500 MHz, DMSO-d$_6$) δ ppm 1.41 (s, 3H), 4.12-4.45 (m, 2H), 6.54 (br. s., 2H), 6.64 (d, J=2.0 Hz, 1H), 7.25-7.32 (m, 2H), 7.45 (d, J=2.0 Hz, 1H), 7.63 (m, J=6.3, 2.5, 2.5 Hz, 1H), 7.82 (br. s, 1H), 8.43 (d, J=2.0 Hz, 1H), 8.72 (d, J=2.0 Hz, 1H), 10.64 (br. s., 1H).

Example B4

Preparation of Compound 4: (R*)-3,5-dichloro-pyridine-2-carboxylic acid [3-(4-amino-6-methyl-6,7-dihydro-pyrazolo[1,5-a]pyrazin-6-yl)-phenyl]-amide and Compound 5: (S*)-3,5-dichloro-pyridine-2-carboxylic acid [3-(4-amino-6-methyl-6,7-dihydro-pyrazolo[1,5-a]pyrazin-6-yl)-phenyl]-amide

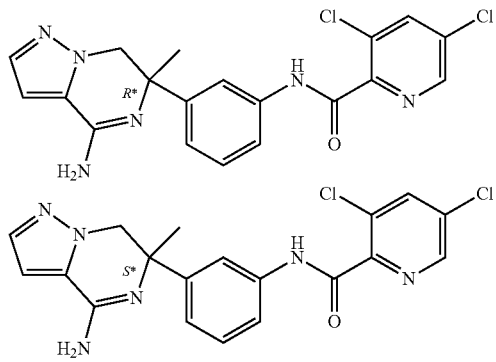

A sample of compound 3 (0.58 g) was washed with cold DCM and then with Et$_2$O. This racemic compound was then separated into the corresponding enantiomers by preparative SFC on Chiralpak AD-H 5 μm (250×20 mm), mobile phase (0.3% iPrNH$_2$, 60% CO$_2$, 40% EtOH). The desired fractions for each enantiomer were collected and concentrated in vacuo to yield compound 4 (152 mg, 26% yield). $^1$H NMR (500 MHz, DMSO-d$_6$) δ ppm 1.41 (s, 3H), 4.28 (br. s, 2H), 6.41 (br. s., 2H), 6.64 (d, J=1.4 Hz, 1H), 7.30 (s, 2H), 7.45 (d, J=2.0 Hz, 1H), 7.60-7.67 (m, 1H), 7.83 (s, 1H), 8.44 (d, J=2.0 Hz, 1H), 8.73 (d, J=2.3 Hz, 1H), 10.65 (br. s., 1H) and compound 5 (155 mg, 27% yield) $^1$H NMR (500 MHz, DMSO-d$_6$) δ ppm 1.41 (s, 3H), 4.28 (s, 2H), 6.41 (br. s., 2H), 6.64 (d, J=0.9 Hz, 1H), 7.26-7.33 (m, 2H), 7.45 (d, J=1.4 Hz, 1H), 7.59-7.69 (m, 1H), 7.84 (s, 1H), 8.44 (d, J=2.0 Hz, 1H), 8.73 (d, J=2.0 Hz, 1H), 10.65 (br. s., 1H) both as white solids.

Example B5

Preparation of Compound 6: rac-5-cyano-pyridine-2-carboxylic acid [3-(4-amino-6-methyl-6,7-dihydro-pyrazolo[1,5-a]pyrazin-6-yl)-phenyl]-amide and Compound 7: (R*)-5-cyano-pyridine-2-carboxylic acid [3-(4-amino-6-methyl-6,7-dihydro-pyrazolo[1,5-a]pyrazin-6-yl)-phenyl]-amide and Compound 8: (S*)-5-cyano-pyridine-2-carboxylic acid [3-(4-amino-6-methyl-6,7-dihydro-pyrazolo[1,5-a]pyrazin-6-yl)-phenyl]-amide

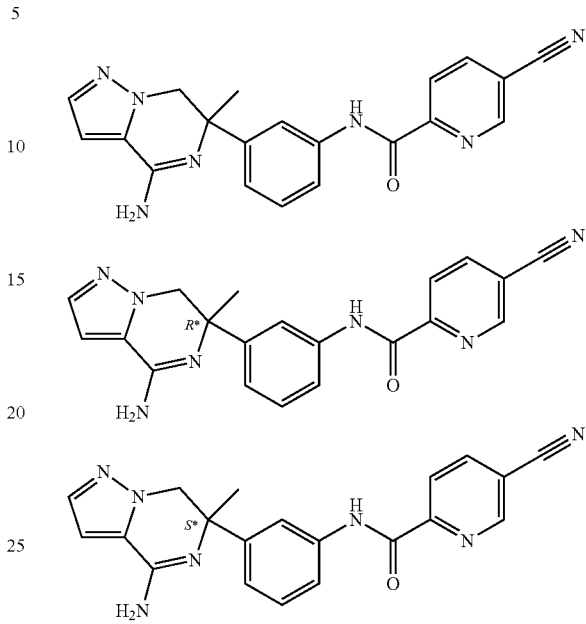

5-Cyano-pyridine-2-carboxylic acid (187.8 mg, 1.27 mmol) was added to a solution of 4-(4,6-dimethoxy-1,3,5-triazin-2-yl)-4-methylmorpholinium chloride (412.9 mg, 1.49 mmol) in MeOH (20 mL). The mixture was stirred at room temperature for 5 min. Then the mixture was cooled to 0° C. and a solution of intermediate A22 (300 mg, 1.24 mmol) in MeOH (10 mL) was added. The mixture was warmed to room temperature and stirred for 4 hours. The mixture was treated with a saturated solution of Na$_2$CO$_3$ and H$_2$O and extracted with DCM. The organic layer was separated, dried (MgSO$_4$), filtered and the solvents evaporated in vacuo. The crude product was purified by flash column chromatography (silica gel; MeOH/DCM). The desired fractions were collected and the solvents evaporated in vacuo. The crude product was triturated with Et$_2$O and then was purified by flash column chromatography (silica gel; 7 M solution of NH$_3$ in MeOH/DCM). The desired fractions were collected and the solvents evaporated in vacuo. The crude product was washed with EtOH and Et$_2$O and then purified by flash column chromatography (silica gel; MeOH/DCM). The desired fractions were collected and the solvents evaporated in vacuo to yield compound 6 (122 mg, 26% yield) as a cream solid. $^1$H NMR (500 MHz, DMSO-d$_6$) δ ppm 1.42 (s, 3H), 4.31 (m, J=3.5 Hz, 2H), 6.66 (br. s, 2H), 6.66 (d, J=1.7 Hz, 1H), 7.26-7.33 (m, 2H), 7.45 (d, J=2.0 Hz, 1H), 7.78 (dt, J=6.9, 1.9 Hz, 1H), 8.01-8.06 (m, 1H), 8.29 (dd, J=8.1, 0.6 Hz, 1H), 8.59 (dd, J=8.1, 2.0 Hz, 1H), 9.18-9.22 (m, 1H), 10.68 (s, 1H). This racemic compound was then further purified by preparative SFC on Chiralpak AD-H 5 μm (250×20 mm), mobile phase (0.3% iPrNH$_2$, 60% CO$_2$, 40% EtOH). The desired fractions for each enantiomer were collected and concentrated in vacuo to yield compound 7 (45.8 mg, 10% yield) $^1$H NMR (500 MHz, DMSO-d$_6$) δ ppm 1.41 (s, 3H), 4.21-4.35 (m, 2H), 6.39 (br. s., 2H), 6.64 (br. s, 1H), 7.26-7.35 (m, 2H), 7.45 (d, J=1.2 Hz, 1H), 7.78 (br. d, J=7.2 Hz, 1H), 8.05 (br. s, 1H), 8.30 (d, J=8.1 Hz, 1H), 8.60 (dd, J=8.1, 2.0 Hz, 1H), 9.20-9.22 (m, 1H), 10.68 (s, 1H) and compound 8 (46.5 mg, 10% yield) $^1$H NMR (500 MHz, DMSO-d$_6$) δ ppm 1.41 (s, 3H), 4.29 (br. s., 2H), 6.41 (br. s., 2H), 6.64 (d, J=1.7 Hz, 1H), 7.27-7.34 (m, 2H), 7.45 (d, J=1.7 Hz, 1H), 7.77-7.80 (m, 1H), 8.05 (br. s, 1H), 8.30 (dd, J=8.2, 0.7 Hz, 1H), 8.60 (dd, J=8.1, 2.0 Hz, 1H), 9.19-9.24 (m, 1H), 10.68 (s, 1H), both as white solids.

Example B6

Preparation of Compound 9: rac-5-cyano-pyridine-2-carboxylic acid [3-(4-amino-3-bromo-6-methyl-6,7-dihydro-pyrazolo[1,5-a]pyrazin-6-yl)-phenyl]-amide trifluorocetate salt

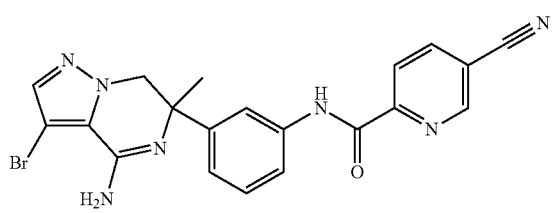 [SMILES: CC1(c2cccc(NC(=O)c3ccc(C#N)cn3)c2)Cn2ncc(Br)c2C(N)=N1]

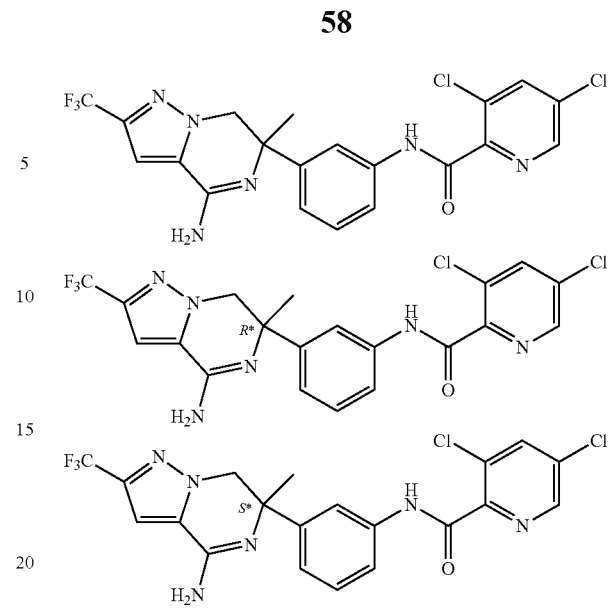

5-Cyano-pyridine-2-carboxylic acid (23.6 mg, 0.16 mmol) was added to a solution of 4-(4,6-dimethoxy-1,3,5-triazin-2-yl)-4-methylmorpholinium chloride (51.9 mg, 0.19 mmol) in MeOH (5 mL). The mixture was stirred at room temperature for 5 min. Then the mixture was cooled to 0° C. and a solution of intermediate A20 (50 mg, 0.16 mmol) in MeOH (5 mL) was added. The mixture was warmed to room temperature and stirred for 4 hours. The mixture was treated with a saturated solution of Na₂CO₃ and H₂O and extracted with DCM. The organic layer was separated, dried (MgSO₄), filtered and the solvents evaporated in vacuo. The crude product was purified by flash column chromatography (silica gel; MeOH/DCM). The desired fractions were collected and the solvents evaporated in vacuo. The crude product was triturated with Et₂O and then was purified by flash column chromatography (silica gel; MeOH/DCM). The desired fractions were collected and concentrated in vacuo and the residue was purified by preparative HPLC (RP C18 XSelect 19×100 5 um), mobile phase (gradient from 80% 0.1% TFA solution in H₂O, 20% CH₃CN to 0% 0.1% TFA solution in H₂O, 100% CH₃CN) to yield compound 9 (9.8 mg, 11% yield) as a white solid. ¹H NMR (500 MHz, DMSO-d₆) δ ppm 1.75 (s, 3H), 4.74 (d, J=13.9 Hz, 1H), 5.09 (d, J=13.6 Hz, 1H), 7.19-7.24 (m, 1H), 7.40 (t, J=8.1 Hz, 1H), 7.87 (dd, J=8.1, 1.2 Hz, 1H), 7.88 (s, 1H), 8.00 (br. s, 1H), 8.29 (dd, J=8.1, 0.6 Hz, 1H), 8.60 (dd, J=8.4, 2.0 Hz, 1H), 8.78 (br. s., 1H), 9.21 (dd, J=2.0, 0.9 Hz, 1H), 9.70 (br. s., 1H), 10.89 (s, 1H), 11.23 (br. s., 1H).

Example B7

Preparation of Compound 10: rac-3,5-dichloro-pyridine-2-carboxylic acid [3-(4-amino-6-methyl-2-trifluoromethyl-6,7-dihydro-pyrazolo[1,5-a]pyrazin-6-yl)-phenyl]-amide and Compound 11: (R*)-3,5-dichloro-pyridine-2-carboxylic acid [3-(4-amino-6-methyl-2-trifluoromethyl-6,7-dihydro-pyrazolo[1,5-a]pyrazin-6-yl)-phenyl]-amide and Compound 12: (S*)-3,5-dichloro-pyridine-2-carboxylic acid [3-(4-amino-6-methyl-2-trifluoromethyl-6,7-dihydro-pyrazolo[1,5-a]pyrazin-6-yl)-phenyl]-amide 3,5-Dichloro-2-pyridinecarboxylic acid (70 mg, 0.366 mmol) was added to a solution of 4-(4,6-dimethoxy-1,3,5-triazin-2-yl)-4-methylmorpholinium chloride (119 mg, 0.431 mmol) in MeOH (5 mL). The mixture was stirred at room temperature for 5 min. Then the mixture was cooled to 0° C. and a solution of intermediate A28 (111 mg, 0.359 mmol) in MeOH (5 mL) was added. The mixture was warmed to room temperature and stirred for 4 hours. The mixture was treated with a saturated solution of Na₂CO₃ and H₂O and extracted with DCM. The organic layer was separated, dried (MgSO₄), filtered and the solvents evaporated in vacuo. The crude product was purified by flash column chromatography (silica gel; MeOH/DCM). The desired fractions were collected and the solvents evaporated in vacuo. The crude product was triturated with Et₂O, sonicated, filtered and dried in vacuo at 50° C. to yield compound 10 (95 mg, 55% yield) as a white solid. This racemic compound was then further purified by preparative SFC on Chiralpak AD-H 5 μm (250×20 mm), mobile phase (0.3% iPrNH₂, 70% CO₂, 30% iPrOH). The desired fractions for each enantiomer were collected and concentrated in vacuo to yield compound 11 (40 mg, 23% yield). ¹H NMR (400 MHz, DMSO-d₆) δ ppm 1.42 (s, 3H), 4.35-4.47 (m, 2H), 6.61 (br. s., 2H), 7.09 (br. s, 1H), 7.26-7.35 (m, 2H), 7.59-7.67 (m, 1H), 7.83 (br. s, 1H), 8.43 (d, J=2.1 Hz, 1H), 8.72 (d, J=2.1 Hz, 1H), 10.67 (s, 1H) and compound 12 (38 mg, 22% yield), for which the ¹H NMR was in agreement with the one of compound 11.

Example B8

Preparation of Compound 13: (R)-5-methoxy-pyrazine-2-carboxylic acid [3-(4-amino-3-fluoro-6-methyl-6,7-dihydro-pyrazolo[1,5-a]pyrazin-6-yl)-4-fluoro-phenyl]-amide

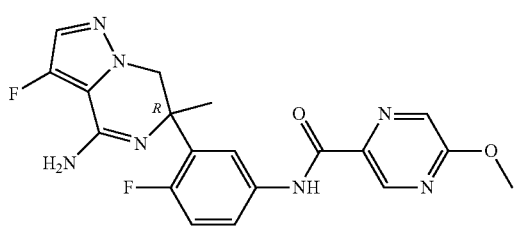

5-Methoxypyrazine-2-carboxylic acid (120 mg, 0.78 mmol) was added to a solution of 4-(4,6-dimethoxy-1,3,5-triazin-2-yl)-4-methylmorpholinium chloride (233 mg, 0.841 mmol) in MeOH (5 mL). The mixture was stirred at room temperature for 5 min. Then the mixture was cooled to 0° C. and a solution of intermediate A39 (212 mg, 0.764 mmol) in MeOH (5 mL) was added. The mixture was warmed to room temperature and stirred for 4 hours. The mixture was treated with a saturated solution of $Na_2CO_3$ and $H_2O$ and extracted with DCM. The organic layer was separated, dried ($MgSO_4$), filtered and the solvents evaporated in vacuo. The crude product was purified by flash column chromatography (silica gel; MeOH/DCM). The desired fractions were collected and the solvents evaporated in vacuo. The crude product was triturated with $Et_2O$ and then was purified by flash column chromatography (silica gel; MeOH/DCM). The desired fractions were collected and concentrated in vacuo to afford a white solid. The solid was treated with DIPE to afford compound 13 (155 mg, 49%) as a white solid. $^1$H NMR (500 MHz, $CDCl_3$) δ ppm 1.59 (s, 3H), 4.06 (s, 3H), 4.28 (br. d, J=13.0 Hz, 1H), 4.51 (br. d, J=13.0 Hz, 1H), 5.04 (br. s., 2H), 7.09 (dd, J=11.6, 9.0 Hz, 1H), 7.36 (d, J=4.0 Hz, 1H), 7.84-7.97 (m, 2H), 8.12 (d, J=1.2 Hz, 1H), 8.99 (d, J=1.2 Hz, 1H), 9.51 (br. s, 1H).

Example B9

Preparation of Compound 14: rac-3,5-dichloro-pyridine-2-carboxylic acid [3-(4-amino-6-methyl-6,7-dihydro-pyrazolo[1,5-a]pyrazin-6-yl)-4-fluoro-phenyl]-amide and Compound 15: (R*)-3,5-dichloro-pyridine-2-carboxylic acid [3-(4-amino-6-methyl-6,7-dihydro-pyrazolo[1,5-a]pyrazin-6-yl)-4-fluoro-phenyl]-amide and Compound 16: (S*)-3,5-dichloro-pyridine-2-carboxylic acid [3-(4-amino-6-methyl-6,7-dihydro-pyrazolo[1,5-a]pyrazin-6-yl)-4-fluoro-phenyl]-amide

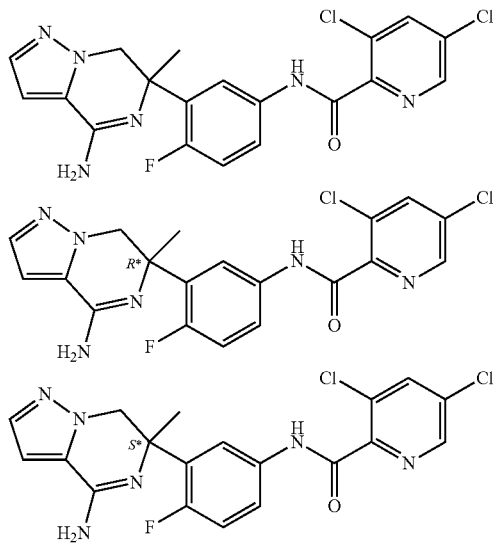

3,5-Dichloro-2-pyridinecarboxylic acid (75.5 mg, 0.393 mmol) was added to a solution of 4-(4,6-dimethoxy-1,3,5-triazin-2-yl)-4-methylmorpholinium chloride (128 mg, 0.463 mmol) in MeOH (5 mL). The mixture was stirred at room temperature for 5 min. Then the mixture was cooled to 0° C. and a solution of intermediate A49 (100 mg, 0.386 mmol) in MeOH (5 mL) was added. The mixture was warmed to room temperature and stirred for 4 hours. The mixture was treated with a saturated solution of $Na_2CO_3$ and $H_2O$ and extracted with DCM. The organic layer was separated, dried ($MgSO_4$), filtered and the solvents evaporated in vacuo. The crude product was purified by flash column chromatography (silica gel; MeOH/DCM). The desired fractions were collected and the solvents evaporated in vacuo. The crude product was triturated with $Et_2O$, sonicated, filtered and dried in vacuo at 50° C. The resulting compound was purified one addition time by flash column chromatography (silica gel; MeOH/DCM) to yield, after treatment with AcOEt and DIPE, compound 14 (95 mg, 57% yield) as a white solid. This racemic compound was then further purified by preparative SFC on Chiralcel OJ-H 5 μm (250×20 mm), mobile phase (0.3% iPrNH$_2$, 85% $CO_2$, 15% EtOH). The desired fractions for each enantiomer were collected and concentrated in vacuo to yield compound 15 (38 mg, 23% yield). $^1$H NMR (400 MHz, $CDCl_3$) δ ppm 1.58 (s, 3H), 2.52 (br. s., 2H), 4.41 (br. d, J=13.2 Hz, 1H), 4.62 (dd, J=13.2, 0.9 Hz, 1H), 6.43 (d, J=2.1 Hz, 1H), 7.08 (dd, J=11.7, 8.9 Hz, 1H), 7.52 (d, J=2.1 Hz, 1H), 7.81 (dd, J=6.9, 2.8 Hz, 1H), 7.89 (d, J=2.1 Hz, 1H), 7.94 (ddd, J=8.8, 4.1, 3.0 Hz, 1H), 8.42 (d, J=2.1 Hz, 1H), 9.71 (br. s., 1H) and compound 16 (40 mg, 24% yield), for which the $^1$H NMR was in agreement with the one of compound 15.

Example B10

Preparation of Compound 17: rac-5-methoxy-pyrazine-2-carboxylic acid [3-(4-amino-6-difluoromethyl-6,7-dihydro-pyrazolo[1,5-a]pyrazin-6-yl)-4-fluoro-phenyl]-amide and Compound 18: (R*)-5-methoxy-pyrazine-2-carboxylic acid [3-(4-amino-6-difluoromethyl-6,7-dihydro-pyrazolo[1,5-a]pyrazin-6-yl)-4-fluoro-phenyl]-amide and Compound 19: (S*)-5-methoxy-pyrazine-2-carboxylic acid [3-(4-amino-6-difluoromethyl-6,7-dihydro-pyrazolo[1,5-a]pyrazin-6-yl)-4-fluoro-phenyl]-amide

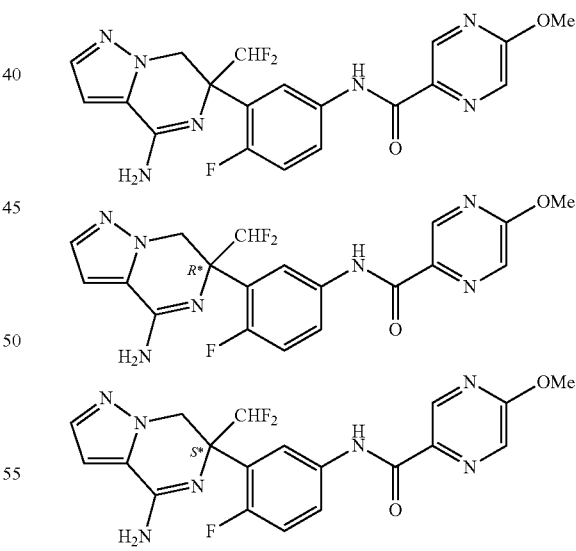

5-Methoxypyrazine-2-carboxylic acid (187.9 mg, 1.219 mmol) was added to a mixture of 4-(4,6-dimethoxy-1,3,5-triazin-2-yl)-4-methylmorpholinium chloride (337 mg, 1.219 mmol) in MeOH (6 mL). The mixture was stirred at room temperature for 5 min. Then the mixture was cooled to 0° C. and a solution of intermediate A58 (300 mg, 1.016 mmol) in MeOH (4 mL) was added. The mixture was warmed to room temperature and stirred for 1 hour, then treated with a saturated solution of Na$_2$CO$_3$ and H$_2$O and extracted with DCM. The organic layer was separated, dried (MgSO$_4$), filtered and the solvents evaporated in vacuo. Part of the product was precipitated with DCM and the remaining crude material purified by flash column chromatography (silica gel; 7 M NH$_3$ in MeOH/DCM). The desired fractions were collected and the solvents evaporated in vacuo. The resulting product was combined with the one obtained from precipitation and triturated with heptane, sonicated and filtered, to afford compound 17 (278 mg, 62% yield) as a white solid. This racemic compound was then further purified by preparative SFC on Chiralcel OD-H 5 μm (250×20 mm), mobile phase (0.3% iPrNH$_2$, 70% CO$_2$, 30% EtOH). The desired fractions for each enantiomer were collected and concentrated in vacuo to yield compound 18 (103 mg, 23% yield). $^1$H NMR (500 MHz, DMSO-d$_6$) δ ppm 4.03 (s, 3H) 4.58 (br. d, J=13.6 Hz, 1H) 4.75 (br. d, J=13.6 Hz, 1H) 6.27 (t, J=55.5 Hz, 1H) 6.68 (d, J=2.0 Hz, 1H) 6.93 (br. s, 2H) 7.20 (dd, J=11.8, 9.0 Hz, 1H) 7.48 (d, J=2.0 Hz, 1H) 7.78 (dt, J=8.4, 3.6 Hz, 1H) 8.17 (dd, J=7.1, 2.7 Hz, 1H) 8.42 (d, J=1.2 Hz, 1H) 8.88 (d, J=1.2 Hz, 1H) 10.51 (s, 1H) and compound 19 (102 mg, 23% yield), for which the $^1$H NMR was in agreement with the one of compound 18.

Example B11

Preparation of Compound 20: rac-5-fluoro-pyridine-2-carboxylic acid [3-(4-amino-6-difluoromethyl-6,7-dihydro-pyrazolo[1,5-a]pyrazin-6-yl)-4-fluoro-phenyl]-amide and Compound 21: (S*)-5-fluoro-pyridine-2-carboxylic acid [3-(4-amino-6-difluoromethyl-6,7-dihydro-pyrazolo[1,5-a]pyrazin-6-yl)-4-fluoro-phenyl]-amide and Compound 22: (R*)-5-fluoro-pyridine-2-carboxylic acid [3-(4-amino-6-difluoromethyl-6,7-dihydro-pyrazolo[1,5-a]pyrazin-6-yl)-4-fluoro-phenyl]-amide

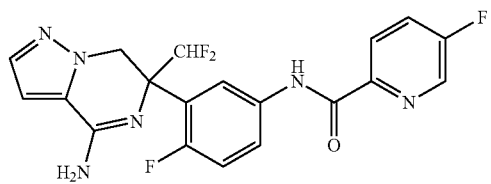

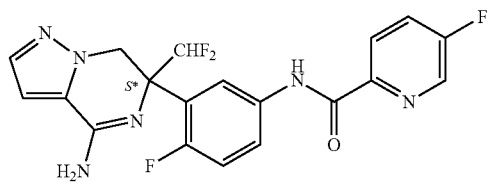

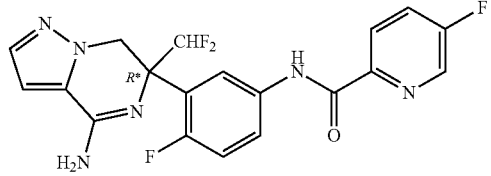

5-Fluoro-2-pyridinecarboxylic acid (74.5 mg, 0.528 mmol) was added to a mixture of 4-(4,6-dimethoxy-1,3,5-triazin-2-yl)-4-methylmorpholinium chloride (146 mg, 0.528 mmol) in MeOH (3 mL). The mixture was stirred at room temperature for 5 min. Then the mixture was cooled to 0° C. and a solution of intermediate A58 (130 mg, 0.44 mmol) in MeOH (2 mL) was added. The mixture was warmed to room temperature and stirred for 1 hour, then treated with a saturated solution of Na$_2$CO$_3$ and H$_2$O and extracted with DCM. The organic layer was separated, dried (MgSO$_4$), filtered and the solvents evaporated in vacuo. The crude product was purified by flash column chromatography (silica gel; 7 M NH$_3$ in MeOH/DCM). The desired fractions were collected and the solvents evaporated in vacuo. The resulting product was triturated with heptane, sonicated and filtered, to afford compound 17 (112 mg, 60% yield) as a white solid. This racemic compound was then further purified by preparative SFC on a Chiralpak AD-H column (5 μm, 250×20 mm), mobile phase [70% CO$_2$, 30% EtOH (+0.3% iPrNH$_2$)]. The desired fractions for each enantiomer were collected and concentrated in vacuo to yield compound 21 (41 mg, 22% yield), for which the $^1$H NMR was in agreement with the one of compound 22, and compound 22 (43 mg, 23% yield). $^1$H NMR (400 MHz, DMSO-d$_6$) δ ppm 4.53-4.61 (m, 1H), 4.74 (br. d, J=13.4 Hz, 1H), 6.26 (t, J=55.9 Hz, 1H), 6.67 (d, J=1.8 Hz, 1H), 6.93 (br. s, 2H), 7.20 (dd, J=12.0, 9.0 Hz, 1H), 7.47 (d, J=1.8 Hz, 1H), 7.79 (ddd, J=8.8, 3.9, 2.8 Hz, 1H), 7.98 (td, J=8.7, 2.9 Hz, 1H), 8.16 (dd, J=7.1, 2.7 Hz, 1H), 8.21 (dd, J=8.8, 4.6 Hz, 1H), 8.73 (d, J=2.8 Hz, 1H), 10.62 (br. s, 1H).

Example B12

Preparation of Compound 23: (R)-5-methoxy-pyrazine-2-carboxylic acid [3-(4-amino-2-cyano-6-methyl-6,7-dihydro-pyrazolo[1,5-a]pyrazin-6-yl)-4-fluoro-phenyl]-amide

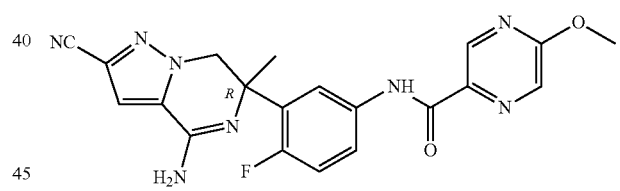

5-Methoxypyrazine-2-carboxylic acid (95.4 mg, 0.619 mmol) was added to a mixture of 4-(4,6-dimethoxy-1,3,5-triazin-2-yl)-4-methylmorpholinium chloride (171.3 mg, 0.619 mmol) in MeOH (3 mL). The mixture was stirred at room temperature for 30 min, then it was cooled to 0° C. and a solution of intermediate A63 (160 mg, 0.563 mmol) in MeOH (3 mL) was added. The mixture was warmed to room temperature and stirred for 20 hour, then treated with a saturated solution of Na$_2$CO$_3$ and stirred for few minutes. The mixture was then extracted with DCM. The organic layer was separated, dried (MgSO$_4$), filtered and the solvents evaporated in vacuo. The crude product was purified by flash column chromatography (silica gel; MeOH/DCM). The desired fractions were collected and the solvents evaporated in vacuo, to afford after drying compound 23 (115 mg, 49% yield) as a solid. $^1$H NMR (500 MHz, CDCl$_3$) δ ppm 1.58 (s, 3H), 1.66 (br. s., 2H), 4.07 (s, 3H), 4.47 (br. d, J=13.6 Hz, 1H), 4.66 (br. d, J=13.3 Hz, 1H), 6.81 (br. s, 1H), 7.09 (dd, J=11.6, 9.0 Hz, 1H), 7.75-7.81 (m, 1H), 7.97 (dd, J=7.1, 2.7 Hz, 1H), 8.14 (s, 1H), 9.00 (s, 1H), 9.49 (br. s., 1H).

Example B13

Preparation of Compound 24: (R)-5-fluoro-pyridine-2-carboxylic acid [3-(4-amino-2-cyano-6-methyl-6,7-dihydro-pyrazolo[1,5-a]pyrazin-6-yl)-4-fluoro-phenyl]-amide

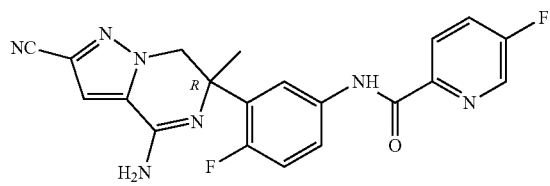

5-Fluoro-2-pyridinecarboxylic acid (87.4 mg, 0.619 mmol) was added to a mixture of 4-(4,6-dimethoxy-1,3,5-triazin-2-yl)-4-methylmorpholinium chloride (171.3 mg, 0.619 mmol) in MeOH (3 mL). The mixture was stirred at room temperature for 30 min, then it was cooled to 0° C. and a solution of intermediate A63 (160 mg, 0.563 mmol) in MeOH (3 mL) was added. The mixture was warmed to room temperature and stirred for 20 hour, then treated with a saturated solution of $Na_2CO_3$ and stirred for few min. The mixture was then extracted with DCM. The organic layer was separated, dried ($MgSO_4$), filtered and the solvents evaporated in vacuo. The crude product was purified by flash column chromatography (silica gel; MeOH/DCM). The desired fractions were collected and the solvents evaporated in vacuo, to afford an oil that was triturated with DIPE. The resulting solid was filtered and dried to give compound 24 (95 mg, 41% yield) as a solid. $^1$H NMR (400 MHz, $CDCl_3$) δ ppm 1.58 (br. s, 3H) 4.46 (br. d, J=13.4 Hz, 1H) 4.66 (d, J=13.4 Hz, 1H) 4.90 (br. s., 2H) 6.81 (s, 1H) 7.10 (dd, J=11.8, 8.8 Hz, 1H) 7.60 (td, J=8.3, 2.8 Hz, 1H) 7.78-7.86 (m, 1H) 7.96 (dd, J=7.1, 2.7 Hz, 1H) 8.32 (dd, J=8.7, 4.5 Hz, 1H) 8.45 (d, J=2.8 Hz, 1H) 9.80 (br. s, 1H).

Example B14

Preparation of Compound 25: (R)-1-difluoromethyl-1H-pyrazole-4-carboxylic acid [3-(4-amino-2-cyano-6-methyl-6,7-dihydro-pyrazolo[1,5-a]pyrazin-6-yl)-4-fluoro-phenyl]-amide

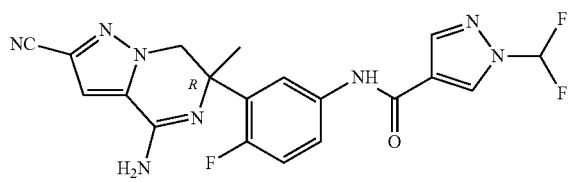

1-Difluoromethyl-1H-pyrazole-3-carboxylic acid (82.7 mg, 0.51 mmol) was added to a mixture of 4-(4,6-dimethoxy-1,3,5-triazin-2-yl)-4-methylmorpholinium chloride (155 mg, 0.561 mmol) in MeOH (3 mL). The mixture was stirred at room temperature for 30 min, then it was cooled to 0° C. and a solution of intermediate A63 (145 mg, 0.51 mmol) in MeOH (3 mL) was added. The mixture was warmed to room temperature and stirred for 3 hour, then treated with a saturated solution of $Na_2CO_3$ and stirred for few min. The mixture was then extracted with DCM. The organic layer was separated, dried ($MgSO_4$), filtered and the solvents evaporated in vacuo. The crude product was purified by flash column chromatography (silica gel; MeOH/DCM). The desired fractions were collected and the solvents evaporated in vacuo, to afford an oil that was triturated with heptane. The resulting solid was filtered and dried to give compound 25 (100 mg, 46% yield) as a solid. $^1$H NMR (500 MHz, $CDCl_3$) δ ppm 1.58 (s, 3H) 4.47 (br. d, J=13.3 Hz, 1H) 4.65 (d, J=13.3 Hz, 1H) 4.94 (br. s., 2H) 6.81 (s, 1H) 7.05 (d, J=2.6 Hz, 1H) 7.09 (dd, J=11.6, 9.0 Hz, 1H) 7.20 (t, J=60.4 Hz, 1H) 7.69-7.75 (m, 1H) 7.88 (d, J=2.6 Hz, 1H) 7.91 (dd, J=6.8, 2.2 Hz, 1H) 8.62 (br. s, 1H).

Example B15

Preparation of Compound 26: (R)-5-cyano-pyridine-2-carboxylic acid [3-(4-amino-2-cyano-6-methyl-6,7-dihydro-pyrazolo[1,5-a]pyrazin-6-yl)-4-fluoro-phenyl]-amide

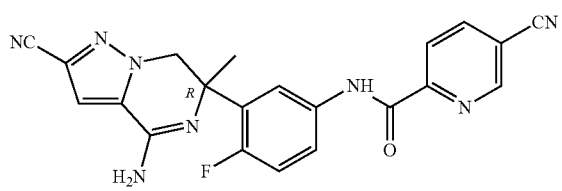

5-Cyano-2-pyridinecarboxylic acid (79.7 mg, 0.538 mmol) was added to a mixture of 4-(4,6-dimethoxy-1,3,5-triazin-2-yl)-4-methylmorpholinium chloride (163.8 mg, 0.592 mmol) in MeOH (3 mL). The mixture was stirred at room temperature for 30 min, then it was cooled to 0° C. and a solution of intermediate A63 (153 mg, 0.538 mmol) in MeOH (3 mL) was added. The mixture was warmed to room temperature and stirred for 3 hour, then treated with a saturated solution of $Na_2CO_3$ and stirred for few min. The mixture was then extracted with DCM. The organic layer was separated, dried ($MgSO_4$), filtered and the solvents evaporated in vacuo. The crude product was purified by flash column chromatography (silica gel; MeOH/DCM). The desired fractions were collected and the solvents evaporated in vacuo, to afford an oil that was triturated with heptane. The resulting solid was filtered and dried to give compound 26 (63 mg, 28% yield) as a solid. $^1$H NMR (500 MHz, DMSO-$d_6$) δ ppm 1.47 (br. s, 3H) 4.43-4.55 (m, 2H) 6.76 (br. s., 2H) 7.20 (dd, J=11.8, 9.0 Hz, 1H) 7.27 (br. s, 1H) 7.71-7.79 (m, 1H) 8.10 (br. d, J=5.2 Hz, 1H) 8.26 (d, J=8.1 Hz, 1H) 8.57 (dd, J=8.2, 1.6 Hz, 1H) 9.18 (br. s, 1H) 10.81 (br. s, 1H).

Example B16

Preparation of Compound 27: (R)-5-fluoro-pyridine-2-carboxylic acid [3-(4-amino-2-difluoromethyl-6-methyl-6,7-dihydro-pyrazolo[1,5-a]pyrazin-6-yl)-4-fluoro-phenyl]-amide

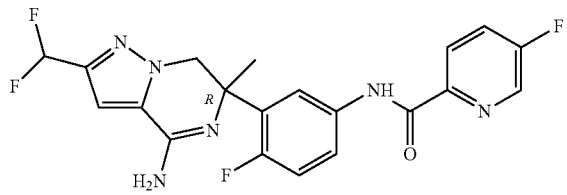

5-Fluoro-2-pyridinecarboxylic acid (68 mg, 0.485 mmol) was added to a mixture of 4-(4,6-dimethoxy-1,3,5-triazin-2-yl)-4-methylmorpholinium chloride (148 mg, 0.533 mmol) in MeOH (3 mL). The mixture was stirred at room temperature for 5 min, then it was cooled to 0° C. and a solution of intermediate A70 (150 mg, 0.485 mmol) in MeOH (2 mL) was added. The mixture was warmed to room temperature and stirred for 4 hours, then concentrated in vacuo in a cold bath. The crude product was purified by flash column chromatography (dry load, silica gel; MeOH/DCM). The desired fractions were collected and the solvents evaporated in vacuo, to afford an off-white solid, that was further purified by RP HPLC on C18 Sunfire (30×100 5 um). Mobile phase: gradient from 80% 0.1% TFA solution in H$_2$O, 20% CH$_3$CN to 0% 0.1% TFA solution in H$_2$O, 100% CH$_3$CN, yielding compound 27 (57 mg, 33%) as a white solid. $^1$H NMR (500 MHz, DMSO-d$_6$) δ ppm 1.84 (br. s, 3H), 4.79 (br. d, J=13.9 Hz, 1H), 5.02 (br. d, J=13.3 Hz, 1H), 7.10 (t, J=54.3 Hz, 1H), 7.30 (dd, J=12.0, 8.8 Hz, 1H), 7.46 (br. s., 1H), 7.86-7.91 (m, 1H), 7.93 (dd, J=7.5, 2.3 Hz, 1H), 7.98 (td, J=8.7, 2.9 Hz, 1H), 8.20 (dd, J=8.7, 4.6 Hz, 1H), 8.73 (d, J=2.9 Hz, 1H), 9.33 (br. s., 1H), 10.07 (br. s., 1H), 10.80 (br. s, 1H), 11.09 (br. s., 1H).

Example B17

Preparation of Compound 28: (R)-5-methoxy-pyrazine-2-carboxylic acid [3-(4-amino-2-difluoromethyl-6-methyl-6,7-dihydro-pyrazolo[1,5-a]pyrazin-6-yl)-4-fluoro-phenyl]-amide

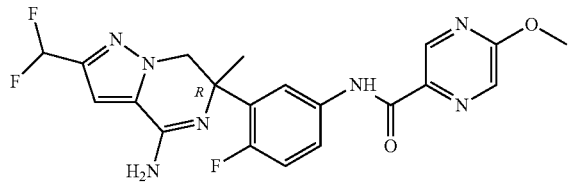

5-Methoxypyrazine-2-carboxylic acid (75 mg, 0.485 mmol) was added to a mixture of 4-(4,6-dimethoxy-1,3,5-triazin-2-yl)-4-methylmorpholinium chloride (148 mg, 0.533 mmol) in MeOH (3 mL). The mixture was stirred at room temperature for 5 min, then it was cooled to 0° C. and a solution of intermediate A70 (150 mg, 0.485 mmol) in MeOH (2 mL) was added. The mixture was warmed to room temperature and stirred for 4 hours, then concentrated in vacuo in a cold bath. The crude product was purified by flash column chromatography (dry load, silica gel; MeOH/DCM). The desired fractions were collected and the solvents evaporated in vacuo, to afford an off-white solid, that was further purified by RP HPLC on C18 Sunfire (30×100 5 um). Mobile phase: gradient from 80% 0.1% TFA solution in H$_2$O, 20% CH$_3$CN to 0% 0.1% TFA solution in H$_2$O, 100% CH$_3$CN, yielding compound 27 (32 mg, 12%) as a white solid. $^1$H NMR (500 MHz, DMSO-d$_6$) δ ppm 1.85 (br. s., 3H) 4.03 (s, 3H) 4.80 (br. d, J=13.9 Hz, 1H) 5.03 (br. d, J=12.7 Hz, 1H) 7.12 (t, J=54.3 Hz, 1H) 7.31 (dd, J=11.8, 9.0 Hz, 1H) 7.47 (br. s., 1H) 7.84-7.90 (m, 1H) 7.96 (dd, J=7.4, 2.2 Hz, 1H) 8.42 (d, J=1.4 Hz, 1H) 8.88 (d, J=1.4 Hz, 1H) 9.32 (br. s., 1H) 10.09 (br. s., 1H) 10.70 (s, 1H) 11.08 (br. s., 1H).

Example B18

Preparation of Compound 29: (R)-5-methoxy-pyrazine-2-carboxylic acid [3-(4-amino-3-fluoro-2,6-dimethyl-6,7-dihydro-pyrazolo[1,5-a]pyrazin-6-yl)-4-fluoro-phenyl]-amide

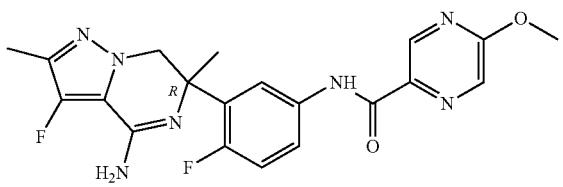

5-Methoxypyrazine-2-carboxylic acid (97 mg, 0.631 mmol) was added to a mixture of 4-(4,6-dimethoxy-1,3,5-triazin-2-yl)-4-methylmorpholinium chloride (175 mg, 0.631 mmol) in MeOH (2 mL). The mixture was stirred at room temperature for 5 min, then it was cooled to 0° C. and a solution of intermediate A73 (175 mg, 0.601 mmol) in MeOH (2 mL) was added. The mixture was warmed to room temperature and stirred for 24 hours, The solvent was removed in vacuo and the residue was suspended in DCM and treated with sat. Na$_2$CO$_3$. The organic layer was separated, dried (MgSO$_4$), filtered and concentrated in vacuo. The crude product was purified by flash column chromatography (silica gel; 7 M NH$_3$ in MeOH/DCM). The desired fractions were collected and the solvents evaporated in vacuo. The residue was suspended in Et$_2$O. The precipitate was filtered off and dried under vacuum at 50° C. to yield compound 29 (195 mg, 76%) as a white solid. $^1$H NMR (500 MHz, DMSO-d$_6$) δ ppm 1.45 (br. s, 3H), 2.12 (s, 3H), 4.02 (s, 3H), 4.18 (br. d, J=13.0 Hz, 1H), 4.24 (br. d, J=12.4 Hz, 1H), 6.26 (br. s., 2H), 7.17 (dd, J=12.0, 8.8 Hz, 1H), 7.68-7.77 (m, 1H), 8.04 (br. d, J=5.2 Hz, 1H), 8.40 (d, J=1.2 Hz, 1H), 8.87 (d, J=1.2 Hz, 1H), 10.46 (br. s, 1H).

TABLE 1

| Co. No. | Ex. No. | R$^1$ | R$^2$ | R$^3$ | X$^1$ | X$^3$ | —L—Ar | C$_4$ Stereochemistry/ salt |
|---|---|---|---|---|---|---|---|---|
| 1 | B1 | H | H | CH$_3$ | CH | CH | ![pyridine-Cl] | R/CF$_3$COOH |

TABLE 1-continued

| Co. No. | Ex. No. | R¹ | R² | R³ | X¹ | X³ | —L—Ar | C₄ Stereochemistry/ salt |
|---|---|---|---|---|---|---|---|---|
| 2 | B2 | H | H | CH₃ | CH | CH | N-H-C(=O)-pyridine-5-Cl | RS |
| 3 | B3 | H | H | CH₃ | CH | CH | N-H-C(=O)-pyridine-3,5-diCl | RS |
| 4 | B4 | H | H | CH₃ | CH | CH | N-H-C(=O)-pyridine-3,5-diCl | S* |
| 5 | B4 | H | H | CH₃ | CH | CH | N-H-C(=O)-pyridine-3,5-diCl | R* |
| 6 | B5 | H | H | CH₃ | CH | CH | N-H-C(=O)-pyridine-5-CN | RS |
| 7 | B5 | H | H | CH₃ | CH | CH | N-H-C(=O)-pyridine-5-CN | R* |
| 8 | B5 | H | H | CH₃ | CH | CH | N-H-C(=O)-pyridine-5-CN | S* |

TABLE 1-continued
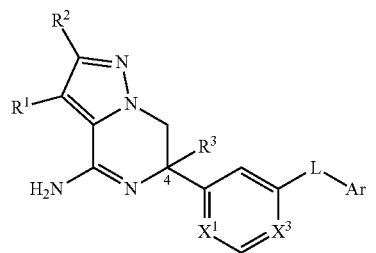
| Co. No. | Ex. No. | R¹ | R² | R³ | X¹ | X³ | —L—Ar | C₄Stereochemistry/salt |
|---|---|---|---|---|---|---|---|---|
| 9 | B6 | Br | H | CH₃ | CH | CH | 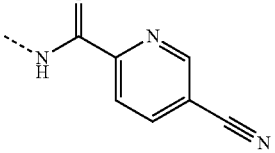 | RS/CF₃COOH |
| 10 | B7 | H | CF₃ | CH₃ | CH | CH | 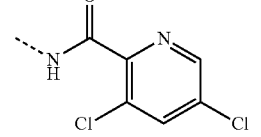 | RS |
| 11 | B7 | H | CF₃ | CH₃ | CH | CH | 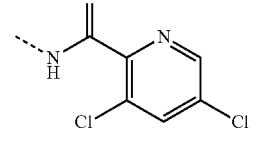 | R* |
| 12 | B7 | H | CF₃ | CH₃ | CH | CH | 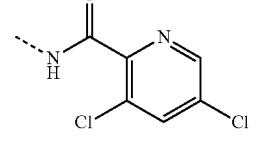 | S* |
| 13 | B8 | F | H | CH₃ | CH | CH | 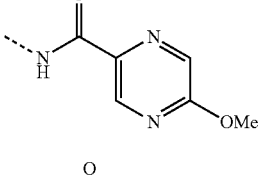 | R |
| 14 | B9 | H | H | CH₃ | CF | CH | 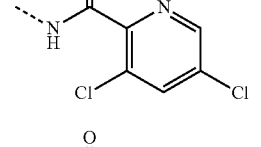 | RS |
| 15 | B9 | H | H | CH₃ | CF | CH | 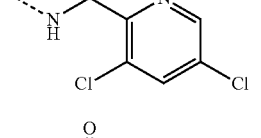 | R* |
| 16 | B9 | H | H | CH₃ | CF | CH | 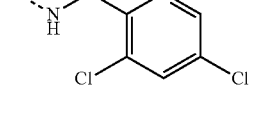 | S* |

TABLE 1-continued
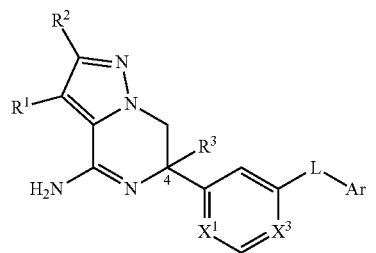
| Co. No. | Ex. No. | R¹ | R² | R³ | X¹ | X³ | —L—Ar | C₄Stereochemistry/salt |
|---|---|---|---|---|---|---|---|---|
| 17 | B10 | H | H | CHF₂ | CF | CH | 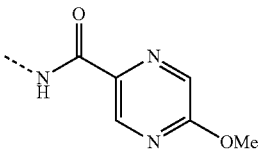 | RS |
| 18 | B10 | H | H | CHF₂ | CF | CH | 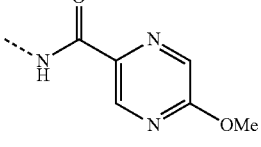 | R* |
| 19 | B10 | H | H | CHF₂ | CF | CH | 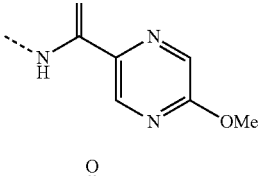 | S* |
| 20 | B11 | H | H | CHF₂ | CF | CH | 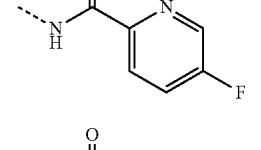 | RS |
| 21 | B11 | H | H | CHF₂ | CF | CH | 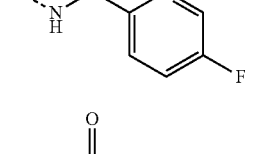 | R* |
| 22 | B11 | H | H | CHF₂ | CF | CH | 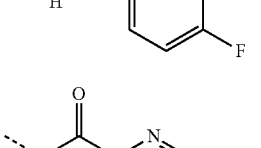 | S* |
| 23 | B12 | H | CN | CH₃ | CF | CH | 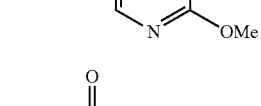 | R |
| 24 | B13 | H | CN | CH₃ | CF | CH | 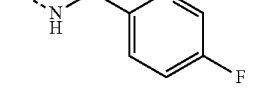 | R |

TABLE 1-continued

| Co. No. | Ex. No. | R¹ | R² | R³ | X¹ | X³ | —L—Ar | C₄Stereochemistry/salt |
|---|---|---|---|---|---|---|---|---|
| 25 | B14 | H | CN | CH₃ | CF | CH | N-H-C(=O)-pyrazole-N-CHF₂ | R |
| 26 | B15 | H | CN | CH₃ | CF | CH | N-H-C(=O)-pyridine-CN | R |
| 27 | B16 | H | CHF₂ | CH₃ | CF | CH | N-H-C(=O)-pyridine-F | R/CF₃COOH |
| 28 | B17 | H | CHF₂ | CH₃ | CF | CH | N-H-C(=O)-pyrazine-OMe | R/CF₃COOH |
| 29 | B18 | F | CH₃ | CH₃ | CF | CH | N-H-C(=O)-pyrazine-OMe | R |
| 30 | B11 | H | CF₃ | CH₃ | CH | CH | N-H-C(=O)-pyrazine-OMe | RS |
| 31 | B11 | H | CF₃ | CH₃ | CH | CH | N-H-C(=O)-pyrazine-OMe | S* |
| 32 | B11 | H | CF₃ | CH₃ | CH | CH | N-H-C(=O)-pyrazine-OMe | R* |

TABLE 1-continued

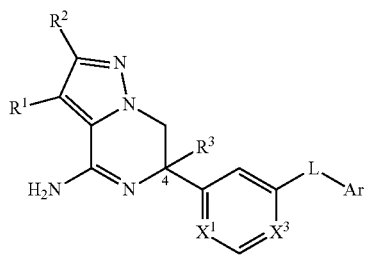

| Co. No. | Ex. No. | R¹ | R² | R³ | X¹ | X³ | —L—Ar | C₄Stereochemistry/ salt |
|---|---|---|---|---|---|---|---|---|
| 33 | B2 | F | H | CH₃ | CF | CH | N-(5-fluoropyridin-2-yl)carboxamide | R |
| 34 | B2 | F | H | CH₃ | CF | CH | N-(2-methyloxazol-4-yl)carboxamide | R |
| 35 | B2 | F | H | CH₃ | CF | CH | N-(2-methyl-5-trifluoromethyloxazol-4-yl)carboxamide | R |
| 36 | B2 | F | H | CH₃ | CF | CH | N-(2,5-dimethyloxazol-4-yl)carboxamide | R |
| 37 | B2 | Cl | H | CH₃ | CF | CH | N-(5-methoxypyrazin-2-yl)carboxamide | R |
| 38 | B2 | Cl | H | CH₃ | CF | CH | N-(5-fluoropyridin-2-yl)carboxamide | R |
| 39 | B16 | H | CHF₂ | CH₃ | CF | CH | N-(5-chloropyridin-2-yl)carboxamide | R |
| 40 | B16 | H | CHF₂ | CH₃ | CF | CH | N-(1-(difluoromethyl)-1H-pyrazol-3-yl)carboxamide | R |

TABLE 1-continued

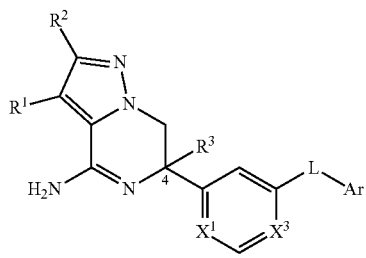

| Co. No. | Ex. No. | R¹ | R² | R³ | X¹ | X³ | —L—Ar | C₄Stereochemistry/salt |
|---|---|---|---|---|---|---|---|---|
| 41 | B2 | F | CH₃ | CH₃ | CF | CH | 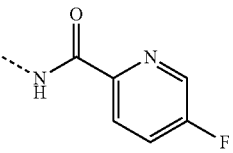 | RS |
| 42 | B2 | F | CH₃ | CH₃ | CF | CH | 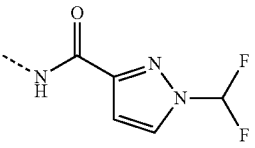 | R |
| 43 | B6 | H | CN | CH₃ | CF | CH | 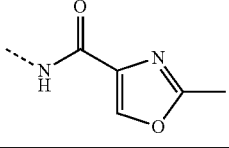 | R |

C. Analytical Part

Nuclear Magnetic Resonance (NMR)

¹H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard LCMS-Method For (LC)MS-characterization of the compounds of the present invention, the following methods were used.

General Procedure a for Acquity-SOD Instrument

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. The MS detector was configured with an electrosprayionization source. Mass spectra were acquired on a single quadrupole SQD detector by scanning from 100 to 1000 in 0.1 second using an inter-channel delay of 0.08 second. The capillary needle voltage was 3.0 kV. The cone voltage was 25 V for positive ionization mode and 30 V for negative ionization mode. Nitrogen was used as the nebulizer gas. The source temperature was maintained at 140° C. Data acquisition was performed with MassLynx-Openlynx software.

Method 1:

In addition to the general procedure A: Reversed phase UPLC was carried out on a BEH-C18 column (1.7 μm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept to 5.0 minutes. Injection volume 2.0 μl.

Method 2:

In addition to the general procedure A: Reversed phase UPLC was carried out on a RRHD Eclipse Plus-C18 (1.8 μm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 1.2 minutes, to 5% A, 95% B in 1.8 minutes, kept to 2.0 minutes. Injection volume 2.0 μl.

Method 3:

Same gradient as method 1; column used: RRHD Eclipse Plus-C18 (1.8 μm, 2.1×50 mm) from Agilent.

General Procedure B for HP 1100-MS Instruments (TOF, SOD or MSD)

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector (SQD, TOF or MSD) was configured with either an electrospray ionization source or an ESCI dual ionization source (electrospray combined with atmospheric pressure chemical ionization). Nitrogen was used as the nebulizer gas. The source temperature was maintained either at 140° C. or 100° C. Data acquisition was performed either with MassLynx-Openlynx software or Chemsation-Agilent Data Browser software.

B1: Mass spectra were acquired on a single quadrupole MSD detector in APCI mode by scanning from 100 to 1000 in 0.99 seconds, step size of 0.30 and peak width of 0.10 minutes. The capillary needle voltage was 3.0 Kv, the fragmentor voltage was 70V for positive and negative ionization modes and the Corona intensity was 4 PA.

B2: Mass spectra were acquired on a single quadrupole SQD detector by scanning from 100 to 1000 in 0.1 second using an inter-channel delay of 0.08 second. The capillary needle voltage was 3.0 kV. The cone voltage was 20 V for positive ionization mode and 30 V for negative ionization mode.

B3: Mass spectra were acquired on a Time of Flight (TOF) detector by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 4:

In addition to the general procedure B1: Reversed phase HPLC was carried out on an Eclipse Plus-C18 column (3.5 μm, 2.1×30 mm) from Agilent, with a flow rate of 1.0 ml/min, at 60° C. The gradient conditions used are: 95% A (6.5 mM $NH_4AcO$ in $H_2O$/ACN 95/5), 5% B (ACN), kept 0.2 minutes, to 100% B in 3.0 minutes, kept to 3.15 minutes and equilibrated to initial conditions at 3.3 minutes until 5.0 minutes. Injection volume 2 μl.

Method 5:

In addition to the general procedure B2: Reversed phase HPLC was carried out on an Eclipse Plus-C18 column (3.5 μm, 2.1×30 mm) from Agilent, with a flow rate of 1.0 ml/min, at 60° C. The gradient conditions used are: 95% A (6.5 mM $NH_4AcO$ in $H_2O$/ACN 95/5), 5% B (ACN/MeOH 1/1), to 100% B in 5.0 minutes, kept to 5.15 minutes and equilibrated to initial conditions at 5.30 minutes until 7.0 minutes. Injection volume 2 μl.

Method 6:

In addition to the general procedure B3: Reversed phase HPLC was carried out on a Eclipse Plus-C18 column (3.5 μm, 2.1×30 mm) from Agilent, with a flow rate of 1.0 ml/min, at 60° C. The gradient conditions used are: 95% A (6.5 mM $NH_4AcO$ in $H_2O$/ACN 95/5), 5% B (ACN), kept 0.2 minutes, to 100% B in 3.0 minutes, kept to 3.15 minutes and equilibrated to initial conditions at 3.3 minutes until 5.0 minutes. Injection volume 2 μl.

General Procedure C

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

Method 7:

In addition to general procedure C: Reversed phase HPLC was carried out on an YMC-Pack ODS-AQ, 50×2.0 mm 5 μm column with a flow rate of 0.8 ml/min. Two mobile phases (mobile phase A: $H_2O$ with 0.1% TFA; mobile phase B: ACN with 0.05% TFA) were used. First, 100% A was hold for 1 minute. Then a gradient was applied to 40% A and 60% B in 4 minutes and hold for 2.5 minutes. Typical injection volumes of 2 μl were used. Oven temperature was 50° C. (MS polarity: positive).

Method 8:

In addition to general procedure C: Reversed phase HPLC was carried out on an Ultimate XB-C18, 50×2.1 mm 5 μm column with a flow rate of 0.8 ml/min. Two mobile phases (mobile phase C: 10 mmol/L $NH_4HCO_3$; mobile phase D:ACN) were used. First, 100% C was hold for 1 minute. Then a gradient was applied to 40% C and 60% D in 4 minutes and hold for 2.5 minutes. Typical injection volumes of 2 μl were used. Oven temperature was 50° C. (MS polarity: positive).

General Procedure D

The UHPLC measurement was performed using a Shimadzu 2010 LCMS-system comprising a pump, photo diode array detector (PDA) (wavelength used 220 nm), a column oven and a column as specified in the respective methods below. Flow from the column was split to a Shimadzu 2010 MSD detector. MS detector was configured with API-ES (atmospheric pressure electrospray ionization). Mass spectra were acquired by scanning from 100 to 1000. The interface voltage was 4500 V for positive ionization mode. The nebulizing gas flow was 1.5 l/min. The CDL (Curved Desolvation Line with heated capillary) temperature was 250° C. and the CDL voltage was 30 V. The heat block temperature was 200° C. The detector voltage was 1500V.

Method 9

In addition to general procedure D: Reversed phase UHPLC was carried out on a Xtimate C18 (30×2.1 mm 3.0 μm) column with a flow rate of 1.2 mL/min. Two mobile phases (A: $H_2O$ with 0.15% TFA; B: ACN with 0.75% TFA) were used. First, 100% A was hold for 1 min. Then a gradient was applied to 40% A and 60% B in 0.9 min, kept to 1.5 min and equilibrated to initial conditions at 1.51 min until 2.0 min. Typical injection volumes of 1.0 μL were used. Oven temperature was 50° C. (MS polarity: positive).

General procedure E

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is held at a temperature of 40° C. Flow from the column was brought to a MS detector. The MS detector was configured with an electrospray ionization source. Mass spectra were acquired on a triple quadrupole mass spectrometer Quattro detector (Waters) by scanning from 100 to 1000 in 0.2 seconds using an inter-scan delay of 0.1 seconds. The capillary needle voltage was 3 kV and the source temperature was maintained at 130° C. Cone voltage was 20V for positive and negative ionization mode. Nitrogen was used as the nebulizer gas. Data acquisition was performed with MassLynx-Openlynx software (Waters).

Method 10:

In addition to the general procedure E: Reversed phase UPLC was carried out on a Waters Acquity BEH (bridged ethylsiloxane/silica hybrid) Phenyl-Hexyl column (1.7 μm, 2.1×100 mm) with a flow rate of 0.343 ml/min. Two mobile phases (mobile phase A: 95% 7 mM7 mM $NH_4AcO$/5% ACN; mobile phase B: 100% ACN) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 ml was used.

Melting Points

Values are either peak values or melt ranges, and are obtained with experimental uncertainties that are commonly associated with this analytical method.

Mettler FP 81HT/FP90—FP62 Apparatus (Indicated by FP90 and FP62 in Table 2)

For a number of compounds, melting points were determined in open capillary tubes either on a Mettler FP62 or a Mettler FP81HT/FP90 apparatus. Melting points were measured with a temperature gradient of 1, 3, 5 or 10° C./minute. Maximum temperature was 300° C. The melting point was read from a digital display.

TABLE 2

Analytical data - $R_t$ means retention time (in min), $[M + H]^+$ means the protonated mass of the compound, method refers to the method used for (LC)MS.

| Co. No. | $R_t$ | $[M + H]^+$ | Method | Melting Point |
|---|---|---|---|---|
| 1 | 1.55 | 338 | 3 | n.d. |
| 2 | 1.6 | 381 | 3 | n.d. |
| 3 | 1.58 | 415 | 3 | 94.4° C. (FP62) |
| 4 | 2.25 | 415 | 10 | 212.2° C. (FP62) |
| 5 | 2.25 | 415 | 10 | 186.3° C. (FP62) |
| 6 | 1.18 | 372 | 3 | 221.6° C. (FP62) |
| 7 | 1.98 | 372 | 10 | 281.8° C. (FP62) |
| 8 | 1.99 | 372 | 10 | 248.8° C. (FP62) |
| 9 | 1.98 | 450 | 3 | 147.4° C. (FP62) |
| 10 | 3.60 | 483 | 5 | >300° C. (FP90) |
| 11 | 2.90 | 483 | 10 | 147.8° C. (FP62) |
| 12 | 2.90 | 483 | 10 | 221.8° C. (FP62) |
| 13 | 0.97 | 414 | 2 | 99.4° C. (FP90) |
| 14 | 1.74 | 433 | 3 | n.d. |
| 15 | 2.37 | 433 | 10 | >300° C. (FP90) |
| 16 | 2.37 | 433 | 10 | >300° C. (FP90) |
| 17 | 1.90 | 432 | 3 | 263.4° C. (FP90) |
| 18 | 2.45 | 432 | 10 | 248° C. (FP90) |
| 19 | 2.45 | 432 | 10 | 279.9° C. (FP90) |
| 20 | 1.94 | 419 | 3 | 236.9° C. (FP90) |
| 21 | 2.48 | 419 | 10 | n.d. |
| 22 | 2.49 | 419 | 10 | 220.4° C. (FP90) |
| 23 | 2.26 | 421 | 3 | 276.3° C. (FP90) |
| 24 | 2.29 | 408 | 3 | 186.4° C. (FP90) |
| 25 | 2.23 | 433 | 3 | 180° C. (FP90) |
| 26 | 2.18 | 446 | 3 | n.d. |
| 27 | 2.14 | 428 | 3 | n.d. |
| 28 | 2.18 | 429 | 3 | n.d. |
| 29 | 2.25 | 415 | 3 | >300° C. (FP90) |
| 30 | 3.31 | 446 | 5 | n.d. |
| 31 | 2.72 | 446 | 10 | 220.9° C. (FP62) |
| 32 | 2.72 | 446 | 10 | 220° C. (FP62) |
| 33 | 0.99 | 401 | 2 | 186° C. (FP90) |
| 34 | 1.47 | 387 | 3 | 187° C. (FP62) |
| 35 | 3.24 | 455 | 5 | 87.2° C. (FP62) |
| 36 | 2.75 | 401 | 5 | 109.8° C. (FP62) |
| 37 | 2.24 | 430 | 3 | 108.8° C. (FP90) |
| 38 | 2.32 | 417 | 3 | >300° C. (FP90) |
| 39 | 2.53 | 449 | 3 | n.d. |
| 40 | 2.04 | 454 | 3 | n.d. |
| 41 | 2.18 | 415 | 3 | n.d. |
| 42 | 1.94 | 436 | 3 | n.d. |
| 43 | 1.86 | 394 | 3 | n.d. | n.d. means not determined

SFCMS-Methods

General Procedure a for SFC-MS Methods

The SFC measurement was performed using an Analytical SFC system from Berger Instruments (Newark, Del., USA) comprising a dual pump control module (FCM-1200) for delivery of carbon dioxide ($CO_2$) and modifier, a thermal control module for column heating (TCM2100) with temperature control in the range 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Method 1

In addition to the general procedure A: The chiral separation in SFC was carried out on a CHIRALPAK AD-H column (4.6 mm×500 mm) at 50° C. with a flow rate of 3.0 ml/min. The mobile phase is CO2, 20% MeOH (containing 0.2% iPrNH2) hold 15.00 min, isocratic mode.

General Procedure B

The SFC measurement was performed using an Analytical SFC system from Berger instruments (Newark, Del., USA) comprising a FCM-1200 dual pump fluid control module for delivering carbon dioxide (CO2) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 µa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

Method 2

In addition to the general procedure B: The chiral separation in SFC was carried out on a CHIRALPAK AD DAICEL column (10 µm, 4.6×250 mm) at 35° C. with a flow rate of 3.0 ml/min. The mobile phase is CO2, 60% Ethanol, 40% EtOH (containing 0.3% iPrNH2) hold 7 min.

TABLE 3

Analytical SFC data - $R_t$ means retention time (in min), $[M + H]^+$ means the protonated mass of the compound, method refers to the method used for SFC/MS analysis of enantiomerically pure compounds.

| Co. No. | $R_t$ | $[M + H]^+$ | UV Area % | Method | Isomer Elution Order* | ee (%) |
|---|---|---|---|---|---|---|
| Intermediate A6(S) | 5.35 | 230 | 100 | 1 | A | — |
| Intermediate A6(R) | 6.88 | 230 | 100 | 1 | B | — |
| 4 | 3.17 | 415 | 100 | 2 | A | — |
| 5 | 4.17 | 415 | 100 | 2 | B | — |
| 7 | 1.92 | 372 | 100 | 2 | A | — |
| 8 | 3.05 | 372 | 100 | 2 | B | — |
| 11 | 4.95 | 483 | 100 | 3 | B | — |
| 12 | 4.01 | 483 | 100 | 3 | A | — |
| 15 | 4.14 | 433 | 100 | 4 | A | — |
| 16 | 5.17 | 433 | 100 | 4 | B | — |
| 18 | 3.07 | 432 | 100 | 5 | A | — |
| 19 | 4.15 | 432 | 100 | 5 | B | — |
| 21 | 2.81 | 419 | 100 | 3 | A | — |
| 22 | 4.17 | 419 | 100 | 3 | B | — |
| 27 | 4.37 | 433 | 89.33 | 6 | A | 79 |
| 28 | 4.97 | 446 | 70.11 | 7 | A | 40 |
| 31 | 3.33 | 446 | 100 | 3 | A | — |

TABLE 3-continued

Analytical SFC data - $R_t$ means retention time (in min), $[M + H]^+$ means the protonated mass of the compound, method refers to the method used for SFC/MS analysis of enantiomerically pure compounds.

| Co. No. | $R_t$ | $[M + H]^+$ | UV Area % | Method | Isomer Elution Order* | ee (%) |
|---|---|---|---|---|---|---|
| 32 | 3.90 | 446 | 99.44 | 3 | B | — |
| 39 | 5.20 | 449 | 91.51 | 6 | A | 83 |
| 40 | 3.40 | 454 | 93.61 | 7 | A | 88 |

*A means the first isomer that elutes. B means the second isomer that elutes. The ee was evaluated in the case of enantiomerically not pure compounds.

Optical Rotations:

Optical rotations were measured on a Perkin-Elmer 341 polarimeter with a sodium lamp and reported as follows: $[\alpha]_\lambda^{t°\,C.}$ (c g/100 ml, solvent).

TABLE 4

Analytical data - Optical rotation values for enantiomerically pure compounds

| Co. No. | $\alpha_D$ (°) | Wavelength (nm) | Concentration w/v % | Solvent | Temp. (° C.) |
|---|---|---|---|---|---|
| 4 | +20.3 | 589 | 0.56 | DMF | 20 |
| 5 | −31.6 | 589 | 0.5 | DMF | 20 |
| 7 | −70.7 | 589 | 0.45 | DMF | 20 |
| 8 | +45.6 | 589 | 0.41 | DMF | 20 |
| 11 | 12.0 | 589 | 0.50 | MeOH | 20 |
| 12 | −18.8 | 589 | 0.50 | MeOH | 20 |
| 13 | 83.7 | 589 | 0.55 | DMF | 20 |
| 18 | 136.8 | 589 | 0.51 | DMF | 20 |
| 19 | −140.8 | 589 | 0.50 | DMF | 20 |
| 21 | −126.7 | 589 | 0.51 | DMF | 20 |
| 22 | 115.2 | 589 | 0.54 | DMF | 20 |
| 23 | 144.4 | 589 | 0.50 | DMF | 20 |
| 24 | 111.4 | 589 | 0.51 | DMF | 20 |
| 25 | 121.1 | 589 | 0.50 | DMF | 20 |
| 29 | 111.0 | 589 | 0.51 | DMF | 20 |
| 31 | 17.9 | 589 | 0.50 | MeOH | 20 |
| 32 | −26.4 | 589 | 0.50 | MeOH | 20 |
| 33 | 56.6 | 589 | 0.65 | DMF | 20 |
| 35 | 81.5 | 589 | 0.50 | DMF | 20 |
| 37 | 29.2 | 589 | 0.52 | DMF | 20 |
| 38 | 14.8 | 589 | 0.49 | DMF | 20 |
| 41 | 65.2 | 589 | 0.50 | DMF | 20 |
| 42 | 77.1 | 589 | 0.50 | DMF | 20 | n.d. means not determined

Pharmacological Examples

The compounds provided in the present invention are inhibitors of the β-site APP-cleaving enzyme 1 (BACE1). Inhibition of BACE1, an aspartic protease, is believed to be relevant for treatment of Alzheimer's Disease (AD). The production and accumulation of β-amyloid peptides (Aβ) from the β-amyloid precursor protein (APP) is believed to play a key role in the onset and progression of AD. Aβ is produced from the amyloid precursor protein (APP) by sequential cleavage at the N- and C-termini of the Aβ domain by β-secretase and γ-secretase, respectively.

Compounds of Formula (I) are expected to have their effect substantially at BACE1 by virtue of their ability to inhibit the enzymatic activity. The behaviour of such inhibitors tested using a biochemical Fluorescence Resonance Energy Transfer (FRET) based assay and a cellular αlisa assay in SKNBE2 cells described below and which are suitable for the identification of such compounds, and more particularly the compounds according to Formula (I), are shown in Table 3.

Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) β-secretase cleavage site. This substrate also contains two fluorophores: (7-methoxycoumarin-4-yl)acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis (Koike H et al. *J. Biochem.* 1999, 126, 235-242). Briefly in a 384-well format recombinant BACE1 protein in a final concentration of 1 μg/ml is incubated for 120 min at room temperature with 10 μm substrate in incubation buffer (40 mM Citrate buffer pH 5.0, 0.04% PEG, 4% DMSO) in the absence or presence of compound. Next the amount of proteolysis is directly measured by fluorescence measurement at T=0 and T=120 (excitation at 320 nm and emission at 405 nm). Results are expressed in RFU, as difference between T120 and T0 A best-fit curve is fitted by a minimum sum of squares method to the plot of % Controlmin versus compound concentration. From this an IC50 value (inhibitory concentration causing 50% inhibition of activity) can be obtained.

$LC$ = Median of the low control values

= Low control: Reaction without enzyme $HC$ = Median of the High control values

= High Control: Reaction with enzyme

% Effect = $100 - [(sample-LC)/(HC-LC)*100]$

% Control = $(sample/HC)*100$

% Controlmin = $(sample-LC)/(HC-LC)*100$

The following exemplified compounds were tested essentially as described above and exhibited the following the activity:

TABLE 5

| Co. No. | Biochemical FRET based assay pIC$_{50}$ |
|---|---|
| 1 | 6.28 |
| 2 | 7.08 |
| 3 | 7.33 |
| 4 | 4.67 |
| 5 | 7.43 |
| 6 | 7.25 |
| 7 | 7.75 |
| 8 | 4.86 |
| 9 | 5.1 |
| 10 | 7.2 |
| 11 | 7.55 |
| 12 | 5.06 |
| 13 | 7.14 |
| 14 | 7.45 |
| 15 | 7.73 |
| 16 | 5.98 |
| 17 | 7.24 |
| 18 | 7.65 |

TABLE 5-continued

| Co. No. | Biochemical FRET based assay pIC$_{50}$ |
|---|---|
| 19 | 5.01 |
| 20 | 7.18 |
| 21 | <4.52 |
| 22 | 7.59 |
| 23 | 7.4 |
| 24 | 7.49 |
| 25 | 7.56 |
| 26 | 7.31 |
| 27 | 7.22 |
| 28 | 7.16 |
| 29 | 7.09 |
| 30 | 6.77 |
| 31 | 4.97 |
| 32 | 7.20 |
| 33 | 7.19 |
| 34 | 7.23 |
| 35 | 6.91 |
| 36 | 7.04 |
| 37 | 5.86 |
| 38 | 6.03 |
| 39 | 7.39 |
| 40 | 7.28 |
| 41 | 6.93 |
| 42 | 7.12 |
| 43 | 7.53 |

Cellular αlisa Assay in SKNBE2 Cells

In two αlisa assays the levels of Aβtotal and Aβ42 produced and secreted into the medium of human neuroblastoma SKNBE2 cells are quantified. The assay is based on the human neuroblastoma SKNBE2 expressing the wild type Amyloid Precursor Protein (hAPP695). The compounds are diluted and added to these cells, incubated for 18 hours and then measurements of Aβ42 and Aβtotal are taken. Aβtotal and Aβ42 are measured by sandwich αlisa. αlisa is a sandwich assay using biotinylated antibody AbN/25 attached to streptavidin coated beads and antibody Ab4G8 or cAb42/26 conjugated acceptor beads for the detection of Aβtotal and Aβ42 respectively. In the presence of Aβtotal or Aβ42, the beads come into close proximity. The excitation of the Donor beads provokes the release of singlet oxygen molecules that triggers a cascade of energy transfer in the Acceptor beads, resulting in light emission. Light emission is measured after 1 hour incubation (excitation at 650 nm and emission at 615 nm).

A best-fit curve is fitted by a minimum sum of squares method to the plot of % Controlmin versus compound concentration. From this an IC50 value (inhibitory concentration causing 50% inhibition of activity) can be obtained.

LC = Median of the low control values
  = Low control: cells preincubated without compound, without biotinylated Ab in the αlisa HC = Median of the High control values
  = High Control: cells preincubated without compound % Effect = 100 − [(sample-LC)/(HC-LC) ∗ 100]

% Control = (sample/HC) ∗ 100

% Controlmin = (sample-LC)/(HC-LC) ∗ 100

The following exemplified compounds were tested essentially as described above and exhibited the following activity:

TABLE 6

| Co. No. | Cellular αlisa assay in SKNBE2 cells Aβ42 pIC$_{50}$ | Cellular αlisa assay in SKNBE2 cells Aβtotal pIC$_{50}$ |
|---|---|---|
| 1 | 7.03 | 7 |
| 2 | 8.49 | 8.61 |
| 3 | 8.49 | 8.47 |
| 4 | 5.84 | 5.84 |
| 5 | 8.59 | 8.55 |
| 6 | 8.24 | 8.29 |
| 7 | 8.66 | 8.69 |
| 8 | 6.13 | 6.13 |
| 9 | 6.00 | 6.06 |
| 10 | 7.78 | 7.81 |
| 11 | 7.94 | 8.01 |
| 12 | 5.64 | 5.75 |
| 13 | 8.17 | 8.26 |
| 14 | 8.87 | 8.93 |
| 15 | 9.33 | 9.37 |
| 16 | 7.66 | 7.74 |
| 17 | 7.40 | 7.48 |
| 18 | 7.52 | 7.54 |
| 19 | 5.28 | 5.13 |
| 20 | 7.07 | 7.18 |
| 21 | <5 | <5 |
| 22 | 7.17 | 7.21 |
| 23 | 8.75 | 8.71 |
| 24 | 8.48 | 8.41 |
| 25 | 8.88 | 8.87 |
| 26 | 8.83 | 8.84 |
| 27 | 8.15 | 8.17 |
| 28 | 8.28 | 8.20 |
| 29 | 7.79 | 7.77 |
| 30 | 7.43 | 7.45 |
| 31 | 5.58 | 5.61 |
| 32 | 7.76 | 7.84 |
| 33 | 8.09 | 8.14 |
| 34 | 7.83 | 7.78 |
| 35 | 7.33 | 7.30 |
| 36 | 7.56 | 7.53 |
| 37 | 6.03 | 6.07 |
| 38 | 6.16 | 6.22 |
| 39 | 8.61 | 8.59 |
| 40 | 8.42 | 8.37 |
| 41 | 7.69 | 7.67 |
| 42 | 8.02 | 7.99 |
| 43 | 8.72 | 8.70 | n.t. means not tested

Demonstration of In Vivo Efficacy

Aβ peptide lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ peptide lowering agents can be administered in any standard form using any standard method. For example, but not limited to, Aβ peptide lowering agents can be in the form of liquid, tablets or capsules that are taken orally or by injection. Aβ peptide lowering agents can be administered at any dose that is sufficient to significantly reduce levels of Aβ peptides in the blood, blood plasma, serum, cerebrospinal fluid (CSF), or brain.

To determine whether acute administration of an Aβ42 peptide lowering agent would reduce Aβ peptide levels in vivo, non-transgenic rodents, e.g. mice or rats were used. Animals treated with the Aβ peptide lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ peptide lowering compounds were formulated in 20% hydroxypropyl β cyclodextrin. The Aβ peptide lowering agents were administered as a single oral dose (p.o.) or a single subcutaneous dose (s.c.) to overnight fasted animals. After a certain time, usually 2 or 4 h (as indicated in Table 7), the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ31-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 µl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Il.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Il.). A reading was performed after 10 to 15 min (excitation 320 nm/emission 420 nm).

In this model at least 20% Aβ42 lowering compared to untreated animals would be advantageous.

The following exemplified compounds were tested essentially as described above and exhibited the following the activity:

TABLE 7

| Co. No. | Aβ42 (% Ctrl)_Mean | Aβtotal (% Ctrl)_Mean | Dose | Route of administration | Time after administration |
|---|---|---|---|---|---|
| 7 | 88 | 101 | 30 mg/kg | p.o. | 4 h. |
| 11 | 89 | 84 | 30 mg/kg | p.o. | 4 h. |
| 23 | 45 | 39 | 10 mg/kg | p.o. | 4 h. |
| 24 | 16 | 31 | 30 mg/kg | p.o. | 4 h. |
| 24 | 66 | 59 | 5 mg/kg | p.o. | 4 h. |
| 27 | 55 | 61 | 10 mg/kg | p.o. | 4 h. |
| 28 | 39 | 50 | 10 mg/kg | p.o. | 4 h. |
| 29 | 59 | 58 | 10 mg/kg | p.o. | 4 h. |
| 32 | 53 | 58 | 30 mg/kg | p.o. | 2 h |
| 33 | 49 | 20 | 100 mg/kg | s.c. | 4 h. | n.t. means not tested;
s.c. means subcutaneous;
p.o. means oral

The invention claimed is:

1. A compound of Formula (I)

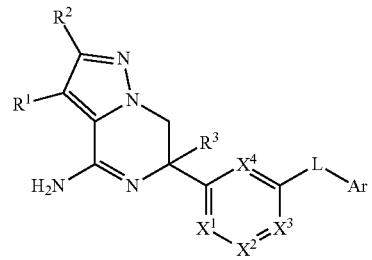

or a tautomer or a stereoisomeric form thereof, wherein
$R^1$ and $R^2$ are independently selected from the group consisting of hydrogen, halo, cyano, $C_{1-3}$alkyl, mono- and polyhalo-$C_{1-3}$alkyl or $C_{3-6}$cycloalkyl;
$R^3$ is selected from the group consisting of hydrogen, $C_{1-3}$alkyl, $C_{3-6}$cycloalkyl, mono- and polyhalo-$C_{1-3}$alkyl, homoaryl and heteroaryl;
$X^1, X^2, X^3, X^4$ are independently $C(R^4)$ or N, provided that no more than two thereof represent N; each $R^4$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^5$)CO—, wherein $R^5$ is hydrogen or $C_{1-3}$alkyl;
Ar is homoaryl or heteroaryl;

wherein homoaryl is phenyl or phenyl substituted with one, two or three substituents selected from the group consisting of halo, cyano, $C_{1-3}$alkyl, $C_{1-3}$ alkyloxy, mono- and polyhalo-$C_{1-3}$ alkyl, mono- and polyhalo-$C_{1-3}$ alkyloxy;

heteroaryl is selected from the group consisting of pyridyl, pyrimidyl, pyrazyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy; or an addition salt or a solvate thereof.

2. The compound of claim 1 wherein,
$R^1$ and $R^2$ are independently selected from hydrogen and $C_{1-3}$alkyl;
$X^1, X^2, X^3, X^4$ are independently $C(R^4)$ wherein each $R^4$ is selected from hydrogen and halo;
L is a bond or —N($R^5$)CO—, wherein $R^5$ is hydrogen;
Ar is homoaryl or heteroaryl;
wherein homoaryl is phenyl or phenyl substituted with one or two substituents selected from the group consisting of halo, cyano, $C_{1-3}$alkyl, $C_{1-3}$alkyloxy, and polyhalo-$C_{1-3}$ alkyloxy;
heteroaryl is selected from the group consisting of pyridyl, pyrimidyl, and pyrazyl, each optionally substituted with one or two substituents selected from the group consisting of halo, cyano, $C_{1-3}$alkyl, $C_{1-3}$alkyloxy, and polyhalo-$C_{1-3}$alkyloxy; or
an addition salt or a solvate thereof.

3. The compound of claim 1 wherein,
$R^1$ and $R^2$ are hydrogen;
$X^1, X^2, X^3, X^4$ are CH;
L is a bond or —N($R^5$)CO—, wherein $R^5$ is hydrogen;
Ar is homoaryl or heteroaryl;
wherein homoaryl is phenyl substituted with chloro;
heteroaryl is selected from the group consisting of pyridyl and pyrimidyl, each optionally substituted with one or two substituents selected from the group consisting of chloro, fluoro, cyano, methyl, and methoxy; or
an addition salt or a solvate thereof.

4. The compound of claim 1 wherein the carbon atom substituted with $R^3$ has the R-configuration.

5. A pharmaceutical composition comprising a therapeutically effective amount of a compound of claim 1 and a pharmaceutically acceptable carrier.

6. A process for preparing a pharmaceutical composition as defined in claim 5, characterized in that a pharmaceutically acceptable carrier is intimately mixed with a therapeutically effective amount of a compound of claim 1.

7. A method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, comprising administering to a subject in need thereof, a therapeutically effective amount of a compound of claim 1 wherein $X^1, X^2, X^3, X^4$ independently $C(R^4)$ or N, provided that no more than one thereof represent N.

8. A pharmaceutical composition comprising a therapeutically effective amount of a compound of claim 3 and a pharmaceutically acceptable carrier.

9. A process for preparing a pharmaceutical composition comprising a therapeutically effective amount of a compound of claim 3 and a pharmaceutically acceptable carrier, characterized in that the pharmaceutically acceptable carrier is intimately mixed with the therapeutically effective amount of said compound.

10. A method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, comprising administering to a subject in need thereof, a therapeutically effective amount of a compound of claim 3.

11. A method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, comprising administering to a subject in need thereof, a therapeutically effective amount of a pharmaceutical composition as defined in claim 5 wherein in said compound of claim 1, $X^1, X^2, X^3, X^4$ are independently $C(R^4)$ or N, provided that no more than one thereof represent N.

12. A method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, comprising administering to a subject in need thereof, a therapeutically effective amount of a pharmaceutical composition as defined in claim 8.

* * * * *